US008986252B2

(12) United States Patent
Cummings et al.

(10) Patent No.: US 8,986,252 B2
(45) Date of Patent: Mar. 24, 2015

(54) CASSETTES AND METHODS OF USING SAME

(75) Inventors: David Charles Cummings, Richardson, TX (US); Alan P. Halbert, Irving, TX (US); Seralaathan Hariharesan, Flower Mound, TX (US); James Allen Higgins, Plano, TX (US); Brian Highley, Keller, TX (US); Michael Rueben Jedwab, Lausanne (CH); Russell Paul Meyer, Plano, TX (US); Andrew Peter Nelson, Dallas, TX (US); David Woodruff West, McKinney, TX (US)

(73) Assignee: Nestec S.A., Vevey (CH)

( * ) Notice: Subject to any disclaimer, the term of this patent is extended or adjusted under 35 U.S.C. 154(b) by 543 days.

(21) Appl. No.: 13/384,126

(22) PCT Filed: Jul. 8, 2010

(86) PCT No.: PCT/US2010/041326
§ 371 (c)(1),
(2), (4) Date: Mar. 30, 2012

(87) PCT Pub. No.: WO2011/008624
PCT Pub. Date: Jan. 20, 2011

(65) Prior Publication Data
US 2012/0191059 A1     Jul. 26, 2012

Related U.S. Application Data

(60) Provisional application No. 61/225,161, filed on Jul. 13, 2009, provisional application No. 61/225,166, (Continued)

(51) Int. Cl.
*A61M 37/00* (2006.01)
*A61M 5/142* (2006.01)
(Continued)

(52) U.S. Cl.
CPC ....... *A61M 5/14232* (2013.01); *A61M 5/16854* (2013.01); *A61M 5/365* (2013.01); *A61M 39/281* (2013.01); *A61M 2205/12* (2013.01); *A61M 2205/14* (2013.01); *A61M 2205/6045* (2013.01)
USPC ........................................ 604/131; 417/477.2

(58) Field of Classification Search
CPC ..................... A61M 2205/12; A61M 2205/14; A61M 2205/6045; A61M 39/281; A61M 5/365
USPC ........................................ 604/131; 417/477.2
See application file for complete search history.

(56) References Cited

U.S. PATENT DOCUMENTS

| 4,537,561 A | 8/1985 | Xanthopoulos |
| 5,591,400 A | 1/1997 | Dektar et al. |

(Continued)

FOREIGN PATENT DOCUMENTS

| EP | 0319277 | 6/1989 |
| EP | 0718001 | 6/1996 |

(Continued)

OTHER PUBLICATIONS

PCT International Search Report for Application No. PCT/US2010/041326 with a Mailing Date of Jan. 20, 2011. 11 Pages.

*Primary Examiner* — Kevin C Sirmons
*Assistant Examiner* — Deanna K Hall
(74) *Attorney, Agent, or Firm* — K&L Gates LLP

(57) ABSTRACT

The present disclosure provides cassettes and methods of using same for the delivery of fluids to a patient using fluid delivery systems. In a general embodiment, the cassettes of the present disclosure include a flexible tube, a housing having a recessed area and first and second ends for holding the flexible tube, and at least two additional components including, for example, different sensors, false reading components for sensors, anti-flow valve means, insertion guides, directional indicators, latch mechanisms, kink-prevention notches, etc. Such additional components provide the cassettes of the present disclosure with several advantages including, for example, quality control, efficiency of use, cost effectiveness, and safety of use.

21 Claims, 56 Drawing Sheets

Related U.S. Application Data filed on Jul. 13, 2009, provisional application No. 61/236,899, filed on Aug. 26, 2009, provisional application No. 61/237,711, filed on Aug. 28, 2009, provisional application No. 61/238,386, filed on Aug. 31, 2009, provisional application No. 61/288,925, filed on Dec. 22, 2009, provisional application No. 61/313,341, filed on Mar. 12, 2010.

(51) Int. Cl.
*A61M 5/168* (2006.01)
*A61M 5/36* (2006.01)
*A61M 39/28* (2006.01)

(56) References Cited

U.S. PATENT DOCUMENTS

| | | | |
|---|---|---|---|
| 5,647,854 A * | 7/1997 | Olsen et al. | 604/174 |
| 5,672,887 A | 9/1997 | Shaw et al. | |
| 6,110,153 A * | 8/2000 | Davis et al. | 604/245 |
| D455,489 S | 4/2002 | Beck et al. | |
| 6,396,583 B1 | 5/2002 | Clare et al. | |
| 6,523,414 B1 | 2/2003 | Malmstrom et al. | |
| 6,659,976 B2 * | 12/2003 | Beck et al. | 604/67 |
| D501,924 S | 2/2005 | Cise et al. | |
| D504,506 S | 4/2005 | Beck et al. | |
| D505,199 S | 5/2005 | Beck et al. | |
| D507,647 S | 7/2005 | Beck et al. | |
| 2002/0151838 A1 | 10/2002 | Beck et al. | |
| 2003/0040700 A1 | 2/2003 | Hickle et al. | |
| 2008/0294094 A1 | 11/2008 | Mhatre et al. | |
| 2009/0118667 A1 | 5/2009 | Haueter et al. | |

FOREIGN PATENT DOCUMENTS

| | | |
|---|---|---|
| EP | 1941922 | 7/2008 |
| EP | 1941923 | 7/2008 |
| WO | 9804301 | 2/1998 |
| WO | 0123277 | 4/2001 |
| WO | 02084256 | 10/2002 |
| WO | 02084336 | 10/2002 |
| WO | 2007141786 | 12/2007 |

* cited by examiner

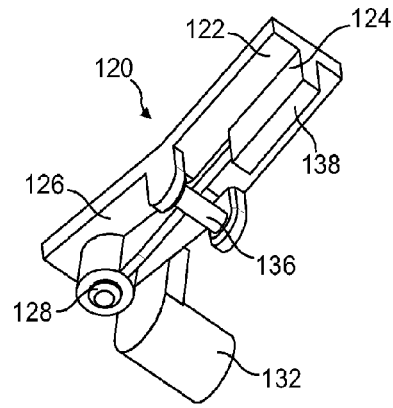
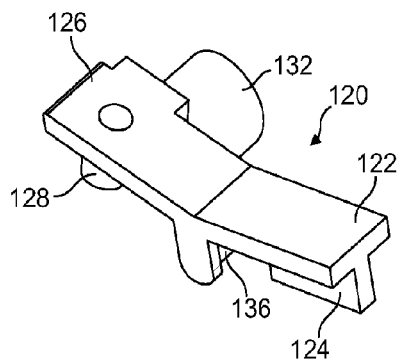
FIG. 23     FIG. 24
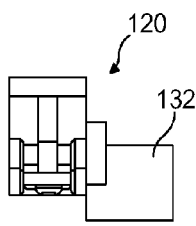
FIG. 25
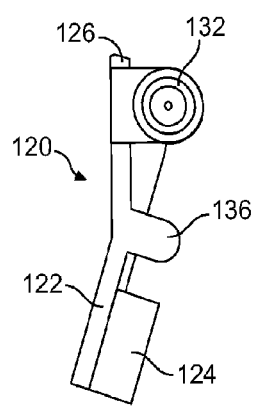
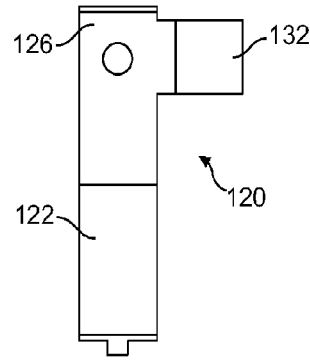
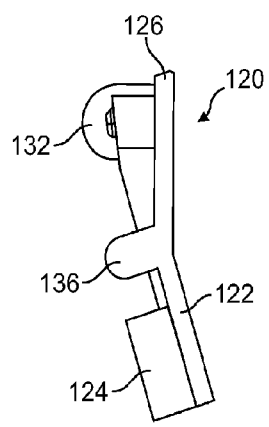
FIG. 26     FIG. 27     FIG. 28

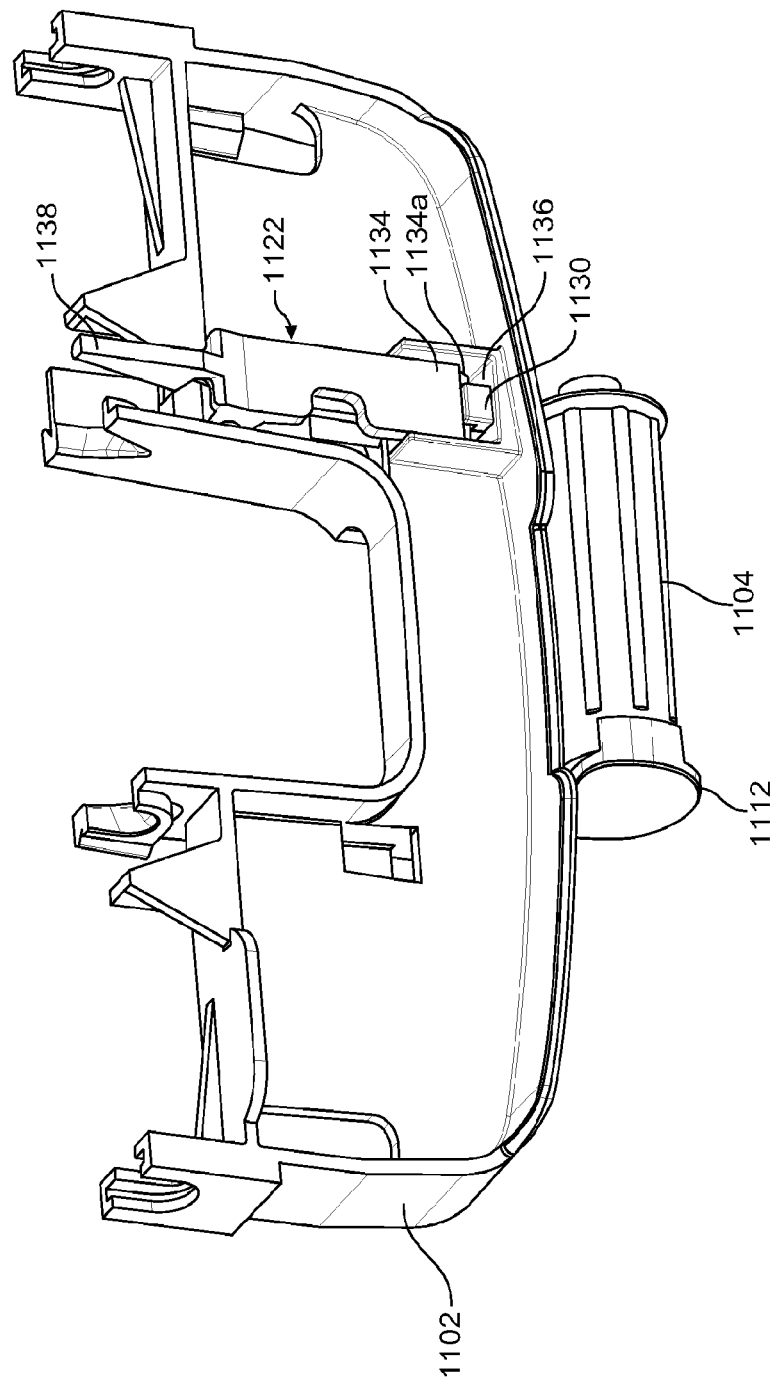

CASSETTES AND METHODS OF USING SAME

This application is a National Stage of International Application No. PCT/US2010/041326 filed Jul. 8, 2010, which claims priority to U.S. Provisional Application Ser. No. 61/225,161 filed Jul. 13, 2009, U.S. Provisional Application Ser. No. 61/225,166 filed Jul. 13, 2009, U.S. Provisional Application Ser. No. 61/236,899 filed Aug. 26, 2009, U.S. Provisional Application Ser. No. 61/237,711 filed Aug. 28, 2009, U.S. Provisional Application Ser. No. 61/238,386 filed Aug. 31, 2009, U.S. Provisional Application Ser. No. 61/288,925 filed Dec. 22, 2009, U.S. Provisional Application Ser. No. 61/313,341 filed Mar. 12, 2010, the contents of all which are expressly incorporated herein by reference in their entirety.

BACKGROUND

The present disclosure relates to apparatuses and methods for enteral or parenteral administration of solutions through the tubing of an infusion line. More particularly, the present disclosure relates to devices that can be associated with infusion pumps for delivery of a fluid to a subject wherein the devices include at least two components that provide improved use of the devices for delivery of such fluids.

Infusion sets are used for both enteral and parenteral applications. Enteral feeding pumps are used to provide patients with nutrition and medication when they are unable, for a variety of reasons, to eat normally. Parenteral (intravenous) solutions are provided to patients to ensure adequate hydration and to provide needed nutrients, minerals and medication.

In many medical applications, enteral and parenteral fluids must be administered to a subject in a well regulated manner. In such instances, a free-standing infusion arrangement, where fluids are delivered to the patient under the force of gravity, is not acceptable. Instead, the fluids may be administered through the use of an infusion pump. An infusion pump is used to regulate the amount and rate at which the fluid is delivered from a reservoir to the patient. Typically, a tube connected to the reservoir passes through the infusion pump and is inserted into the patient. The tubes usually form part of the pumping device such that the pump acts on the tubing to pump fluids. However, pumping devices may also be used that require separate cassettes having tubing to be inserted into the pumping device to pump fluids through the tubes. Such cassettes may provide additional components that are used, for example, for improving efficiency and safety of the infusion sets.

SUMMARY

Cassettes for use with medical pumping devices are provided. Methods of using cassettes are also provided. In a general embodiment, the present disclosure provides a cassette including a flexible tube, a housing, and at least two components selected from the group consisting of an air-in-line sensor device, a false reading component for an air-in-line sensor device, an occlusion sensor device, a false reading component for an occlusion sensor device, a latch sensor device, a false reading component for a latch sensor device, anti-flow valve means, a projection located on a top surface of the housing, at least one notch on an edge of the housing, at least one tab member located on an exterior of the housing, a directional indicator on a surface of the housing, or combinations thereof.

In an embodiment, the cassette housing includes a recessed area so constructed and arranged to receive a portion of a pumping device. The housing may also include first and second ends for holding the flexible tube.

In an embodiment the cassette is made of a non-reflective material. In an embodiment, the cassette has a dark pigment added to it. In an embodiment, the cassette has a dark pigment added to it to prevent ambient light from traveling along the cassette. In an embodiment, the cassette has carbon black pigment added to it. In an embodiment, the cassette has carbon black pigment added to it to prevent ambient light from traveling along the cassette.

In an embodiment, the cassette includes an air-in-line sensor device. The air-in-line sensor device may include a detection chamber, which may be so constructed and arranged for receiving a portion of the flexible tube. The detection chamber can include a window for allowing infra-red light transmission to pass therethrough. The detection chamber may have more than one window. In an embodiment, the detection chamber is made from a molded, plastic chamber that is so constructed and arranged to hold the flexible tube. In an embodiment, the detection chamber is made from a transparent polyvinyl chloride material. The detection chamber may also have a at least a portion that includes an infra-red transparent surface, or at least a portion that includes an infra-red blocking material. The detection chamber may be attached to the cassette and may have two ends, each end being configured to attach to the flexible tube.

In an embodiment, the cassette includes a false reading component for an air-in-line sensor device. The false reading component for the air-in-line sensor device may be made from a material selected from the group consisting of white paper, a metallic surface, infra-red reflective plastic, infra-red reflective glass, infra-red reflective paint, infra-red reflective tape, or combinations thereof. The false reading component for the air-in-line sensor device may be located between flexible tube and a side of the cassette facing an interior of a pump when the cassette is inserted into a pumping device. In an embodiment, the false reading component for the air-in-line sensor device is a piece of infra-red reflective plastic.

In an embodiment, the cassette includes an occlusion sensor device. The occlusion sensor device may include a tube made from a material selected from the group consisting of opaque, infra-red reflective, or combinations thereof, and a bias bump located adjacent to a portion of the tube. The tube may have opaque walls. Alternatively, the at least a portion of the tube may include an infra-red reflective surface.

In an embodiment, the tube is configured to expand or contract in response to a fluid pressure therein and may be contained within a tube housing that defines a window. The tube housing can be formed integrally with the cassette. The tube housing may be formed from opaque polyvinyl chloride, or may have at least a portion of the tube housing including an infra-red transparent surface. In an embodiment, at least a portion of the tube housing includes an infra-red absorbing material.

In an embodiment, the bias bump is substantially rigid to prevent the tube from expanding past bias bump.

In an embodiment, the tube is part of an enteral feeding tube set.

In an embodiment, the cassette includes a false reading component for an occlusion sensor device. The false reading component for the occlusion sensor device includes a material selected from the group consisting of white paper, a metallic surface, infra-red reflective plastic, infra-red reflective glass, infra-red reflective paint, infra-red reflective tape, or combinations thereof. The false reading component for the occlusion sensor device is located between the tube and a side of the cassette facing an interior of a pump when the cassette is inserted into a pumping device. In an embodiment, the false reading component for the occlusion sensor device is a piece of infra-red reflective plastic.

In an embodiment, the cassette includes a latch sensor device. The latch sensor device may include a cassette housing having at least a portion of an infra-red reflective material that is so constructed and arranged to communicate with an infra-red sensor of a pumping device when the cassette is inserted into the pumping device.

In an embodiment, the cassette includes a false reading component for a latch sensor device. The false reading component for the latch sensor device includes a material selected from the group consisting of white paper, a metallic surface, infra-red reflective plastic, infra-red reflective glass, infra-red reflective paint, infra-red reflective tape, or combinations thereof. The false reading component for the latch sensor device is located between an infra-red reflective material of a housing of the cassette and an interior of a pump when the cassette is inserted into a pumping device. In an embodiment, the false reading component for the latch sensor device is a piece of infra-red reflective plastic.

In an embodiment, the cassette includes anti-flow valve means.

In an embodiment, the anti-flow valve means includes an anti-flow valve mechanism that is biased against the flexible tube in a fluid non-delivery position to prevent flow therethrough, and a member operatively associated with the anti-flow valve mechanism to overcome the force-applying member bias to allow flow of fluid through the tube when the housing is engaged with a pump. The housing may be configured and dimensioned for engagement with an infusion pump, wherein during or after engagement the member assumes a fluid delivery position to allow flow of the fluid through the tube, while before or as the cassette is removed from the pump, the member assumes the fluid non-delivery position to prevent flow of fluid through the tubing.

In an embodiment, the anti-flow valve mechanism is associated with the tube, cassette or housing or is situated in or near the cassette or housing and includes a moveable member and a force-applying member. The member may be a tab member that is moveable between the fluid non-delivery position and the fluid delivery position, wherein prior to engagement of the housing with the pump, the tab member and moveable member are in the fluid non-delivery position whereas during or after engagement the tab member overcomes the force-applying member bias and moves the movable member to the fluid delivery position.

In an embodiment, the tab member moves the moveable member to the fluid delivery position as the cassette engages the infusion pump to allow flow of fluid through the tubing and as the cassette is removed from the pump the tab member is released so that the moveable member returns to the fluid non-delivery position to prevent flow of fluid through the tubing such that movement of the tab member between the fluid non-delivery position and the fluid delivery position changes the biasing of the force-applying member.

In an embodiment, the tab member moves the moveable member to the fluid delivery position after the cassette engages the infusion pump to allow flow of fluid through the tubing, and before the cassette is removed from the pump the tab member is released so that the moveable member returns to the fluid non-delivery position to prevent flow of fluid through the tubing such that movement of the tab member between the fluid non-delivery position and the fluid delivery position changes the biasing of the force-applying member.

In an embodiment, the housing has an essentially rectangular shape and is configured and dimensioned to fit within an opening in the infusion pump, and the length of tubing is initially held between the ends of the cassette in a straight line and in front of a rigid curved wall of the housing such that when engaged with the pumping mechanism of the pump, the length of tubing is accurately positioned in contact with and between the curved wall and the pumping mechanism.

In an embodiment, the force-applying member includes a compression spring and the moveable member of the anti-flow valve mechanism includes a pinch head that has a relatively larger cross-sectional surface that contacts the force-applying member and a relatively narrower cross-sectional surface contacting the tubing that concentrates the force of the force-applying member against the tubing.

In an embodiment, the housing includes registration grooves for alignment of the cassette during engagement with the infusion pump, and the housing includes at least one window adjacent the tubing to allow monitoring or detection of fluid flow therethrough.

In an embodiment, the housing is made of molded plastic, the tubing is made of an elastomeric or silicone material, and the tubing is held between inlet and outlet tubing supports in the housing, wherein each tubing support includes a male junction and a female junction, wherein in the inlet support the male junction is configured and dimensioned to fit inside the tubing and the female junction is configured and dimensioned to receive tubing extending to a fluid supply, and in the outlet support, the male junction is configured and dimensioned to fit inside the tubing and the female junction is configured and dimensioned to receive the length of tubing that extends to the subject.

In an embodiment, the anti-flow valve means includes a base including holding means for holding the tube in operative engagement with the base, a first clamping surface and supporting means for supporting a connector, a clamping element having a second clamping surface engageable with the tube and moveable between an open position allowing flow of fluid through the tube and a closed position wherein the tube is occluded by the clamping element, a connector for connecting the tube with a-port on a patient, the connector being removable from the pinch clamp assembly, and a spring. The connector may be adapted to engage with the clamping element so as to hold the clamping element in the open position, and the clamping element is forced from the open to the closed position by the force of the spring as soon as the connector is removed from the assembly, and the clamping element is adapted to be moved from the closed to the open position when the pinch clamp assembly is mounted to the enteral feeding or infusion pump and the connector is removed. The clamping element may be hinged at the base.

In an embodiment, the connector is selected from the group consisting of an enteral spike, an IV spike, an enteral feeding adapter, an IV luer lock adapter, another enteral or IV component, or combinations thereof. The connector may be threadedly coupled to the clamping element and/or the supporting means.

In an embodiment, the base is formed as a cassette such that the pinch clamp assembly may be integrally mounted to the enteral feeding or infusion pump. The base, the clamping element and the connector may be made of recyclable plastic material such as thermoplastics, and the spring may be made of metal. The tube may be made of silicone.

In an embodiment, the base includes a cylindrically-shaped holding element to accommodate a spring.

In an embodiment, the clamping element includes a first leg with a tube blocking portion, a second leg having means for engagement with the spring and a retainer for engagement with the connector, and a swivel pin adapted to engage with a suitable seating on the base. The retainer may be constructed as a cap which is adapted to accommodate the tip of the connector.

In an embodiment, the first and/or second clamping surfaces are uneven, corrugated or finned.

In an embodiment, the base includes a first and a second inner wall between which the clamping element is arranged.

In an embodiment, the anti-flow valve means includes a housing having a constrictor, a tube attached to the housing and positioned through the constrictor, and a ball located inside the tube. The constrictor may be so constructed and arranged to prevent the ball from moving through the tube at a location proximate the constrictor. The tube may include a first end attached to an inlet port and a second end attached to an outlet port. The inlet port is sized to prevent the ball from entering the inlet port.

In an embodiment, the anti-flow valve means includes a housing having a flow restrictor with a locking member and a spring, and a tube attached to the housing and positioned adjacent the flow restrictor. The locking member may be so constructed and arranged to rotate when inserted into a pumping device.

In an embodiment, the housing further includes a stopper positioned adjacent the tube and on an opposite side of the tube from the flow restrictor. The flow restrictor and the stopper may occlude the tube when the flow restrictor is in a resting position. The flow restrictor and the stopper allow a fluid to flow through the tube when the flow restrictor is in an actuated position.

In an embodiment, at least a portion of the tube is flexible.

In an embodiment, the cassette includes a projection on a top surface of the housing. The projection may be substantially cylindrically shaped and may be located in the middle of a length of the housing. The projection may be located on an outer portion of the top surface of the housing. The projection is so constructed and arranged to cooperate with a latch mechanism of a pumping device to lock the cassette into place in the pumping device.

In an embodiment, the cassette includes a notch on at least one edge of a housing. The edge is contiguous to a recessed area of a cassette housing. The notch may have a shape selected from the group consisting of semi-circular, "V"-shaped, oblong, square, rectangular, or combinations thereof. In an embodiment, the notch is substantially "V"-shaped. The "V"-shape is defined by a cut-away portion and a beveled portion of the edge. The notch may be so constructed and arranged to partially receive a tube when the cassette is inserted into a pumping device.

In an embodiment, the cassette includes at least one tab member on a side wall of a cassette housing. The cassette may also include at least one tab member on at least two sides of the cassette. The tab members may be so constructed and arranged to communicate with ledges on an interior wall of a pumping device to guide the cassette during insertion into the pumping device. The tab members have a shape selected from the group consisting of semi-circular, square, rectangular, oblong, triangular, wing-shaped, or combinations thereof. In an embodiment, the tab members are substantially wing-shaped. The tab members may be formed integrally with the cassette, or may be adhered to a side of the cassette.

In an embodiment, the cassette includes at least one directional indicator. The directional indicator is located on a surface of a cassette housing. The directional indicator is an indicator selected from the group consisting of letters, written indicators, logos, symbols, numbers, or combinations thereof. In an embodiment, the cassette includes at least two directional indicators. The directional indicator may be a sticker that is adhered to a wall of a cassette housing. The directional indicator may be applied to a wall of a housing of the cassette using a technique selected from the group consisting of etching, lasering, molding, forming, or combinations thereof. The directional indicator is indicative of a proper orientation of the cassette when the cassette is inserted into a pumping device.

In an embodiment, a cassette for engagement with an infusion pump for delivery of a fluid to a subject is provided. The cassette includes flexible tubing through which the fluid is directed and a housing having first and second ends for holding the flexible tubing and which at least partially defines a flow path along which the tubing is tensioned for fluid flow therein, wherein the tubing is configured for engaging a pumping mechanism of an infusion pump that provides movement of fluid through the tubing, wherein the length of tubing is initially held between the ends of the cassette in a straight line, but, when engaged with the pumping mechanism of the pump, the length of tubing is accurately and repeatably tensioned and positioned in the flow path with the pumping mechanism stretching the flexible tubing to repeatably tension the tubing to allow correct fluid flow therethrough.

In an embodiment, the flow path is at least partially defined by a rigid curved wall that forms a concave shape opposite the pumping mechanism and the tubing is in contact with the curved wall and is positioned along the flow path between the curved wall and the pumping mechanism upon each engagement of the pumping mechanism and tubing.

In an embodiment, the cassette includes an anti-flow valve mechanism that is initially biased against the tubing in a fluid non-delivery position to prevent flow therethrough, and a member operatively associated with the cassette and anti-flow valve mechanism to overcome the force-applying member bias to allow flow of fluid through the tubing when the housing is engaged with the pump. The housing is configured and dimensioned for engagement with the infusion pump, wherein during or after engagement the member assumes a fluid delivery position to allow flow of the fluid through the tubing, while before or as the cassette is removed from the pump, the member assumes the fluid non-delivery position to prevent flow of fluid through the tubing.

In an embodiment, the anti-flow valve mechanism is associated with the tubing, cassette or housing or is situated in or near the cassette or housing and includes a moveable member and a force-applying member, wherein the force applying member in the fluid non-delivery position biases the moveable member against the tubing to prevent flow therethrough, and wherein the moveable member is moveable between the fluid non-delivery position and the fluid delivery position where the force-applying member bias is removed so as to allow fluid flow through the tubing.

In an embodiment, the housing includes registration grooves for alignment of the cassette during engagement with the infusion pump, wherein the housing includes at least one window adjacent the tubing to allow monitoring or detection of fluid flow therethrough.

In an embodiment, the housing is made of molded plastic and the tubing is made of an elastomeric or silicone material, and the tubing is held between inlet and outlet tubing supports in the housing, wherein each tubing support includes a male junction and a female junction, wherein in the inlet support the male junction is configured and dimensioned to fit inside the tubing and the female junction is configured and dimensioned to receive tubing extending to a fluid supply, and in the outlet support, the male junction is configured and dimensioned to fit inside tubing and the female junction is configured and dimensioned to receive the length of tubing that extends to the subject.

In an embodiment, a system for administering a medical fluid to an individual is provided. The system includes a cassette according to any one of the previous embodiments, a pump, and a source of medical fluid. The source of medical fluid may be fluidly coupled to the cassette.

In an embodiment, a method of using a cassette for administration of a medical fluid is provided. The method includes providing a cassette according to any one of the previous embodiments, inserting the cassette into a pumping device, and pumping medical fluid through the cassette.

In an embodiment, a method of providing fluid to a patient is provided. The method includes pumping fluid into the patient using a cassette including a flexible tube, a housing, and at least two components selected from the group consisting of an air-in-line sensor device, a false reading component for an air-in-line sensor device, an occlusion sensor device, a false reading component for an occlusion sensor device, a latch sensor device, a false reading component for a latch sensor device, anti-flow valve means, a projection located on a top surface of the housing, at least one notch on an edge of the housing, at least one tab member located on an exterior of the housing, a directional indicator on a surface of the housing, or combinations thereof.

In an embodiment, the cassette housing includes a recessed area so constructed and arranged to receive a portion of a pumping device. The housing may also include first and second ends for holding the flexible tube.

In an embodiment, the cassette includes an air-in-line sensor device. The air-in-line sensor device may include a detection chamber, which may be so constructed and arranged for receiving a portion of the flexible tube. The detection chamber can include a window for allowing infra-red light transmission to pass therethrough. The detection chamber may have more than one window. In an embodiment, the detection chamber is made from a molded, plastic chamber that is so constructed and arranged to hold the flexible tube. In an embodiment, the detection chamber is made from a transparent polyvinyl chloride material. The detection chamber may also have a at least a portion that includes an infra-red transparent surface, or at least a portion that includes an infra-red blocking material. The detection chamber may be attached to the cassette and may have two ends, each end being configured to attach to the flexible tube.

In an embodiment, the cassette includes a false reading component for an air-in-line sensor device. The false reading component for the air-in-line sensor device may be made from a material selected from the group consisting of white paper, a metallic surface, infra-red reflective plastic, infra-red reflective glass, infra-red reflective paint, infra-red reflective tape, or combinations thereof. The false reading component for the air-in-line sensor device may be located between flexible tube and a side of the cassette facing an interior of a pump when the cassette is inserted into a pumping device. In an embodiment, the false reading component for the air-in-line sensor device is a piece of infra-red reflective plastic.

In an embodiment, the cassette includes an occlusion sensor device. The occlusion sensor device may include a tube made from a material selected from the group consisting of opaque, infra-red reflective, or combinations thereof, and a bias bump located adjacent to a portion of the tube. The tube may have opaque walls. Alternatively, the at least a portion of the tube may include an infra-red reflective surface.

In an embodiment, the tube is configured to expand or contract in response to a fluid pressure therein and may be contained within a tube housing that defines a window. The tube housing can be formed integrally with the cassette. The tube housing may be formed from opaque polyvinyl chloride, or may have at least a portion of the tube housing including an infra-red transparent surface. In an embodiment, at least a portion of the tube housing includes an infra-red absorbing material.

In an embodiment, the bias bump is substantially rigid to prevent the tube from expanding past bias bump.

In an embodiment, the tube is part of an enteral feeding tube set.

In an embodiment, the cassette includes a false reading component for an occlusion sensor device. The false reading component for the occlusion sensor device includes a material selected from the group consisting of white paper, a metallic surface, infra-red reflective plastic, infra-red reflective glass, infra-red reflective paint, infra-red reflective tape, or combinations thereof. The false reading component for the occlusion sensor device is located between the tube and a side of the cassette facing an interior of a pump when the cassette is inserted into a pumping device. In an embodiment, the false reading component for the occlusion sensor device is a piece of infra-red reflective plastic.

In an embodiment, the cassette includes a latch sensor device. The latch sensor device may include a cassette housing having at least a portion of an infra-red reflective material that is so constructed and arranged to communicate with an infra-red sensor of a pumping device when the cassette is inserted into the pumping device.

In an embodiment, the cassette includes a false reading component for a latch sensor device. The false reading component for the latch sensor device includes a material selected from the group consisting of white paper, a metallic surface, infra-red reflective plastic, infra-red reflective glass, infra-red reflective paint, infra-red reflective tape, or combinations thereof. The false reading component for the latch sensor device is located between an infra-red reflective material of a housing of the cassette and an interior of a pump when the cassette is inserted into a pumping device. In an embodiment, the false reading component for the latch sensor device is a piece of infra-red reflective plastic.

In an embodiment, the cassette includes anti-flow valve means.

In an embodiment, the anti-flow valve means includes an anti-flow valve mechanism that is biased against the flexible tube in a fluid non-delivery position to prevent flow therethough, and a member operatively associated with the anti-flow valve mechanism to overcome the force-applying member bias to allow flow of fluid through the tube when the housing is engaged with a pump. The housing may be configured and dimensioned for engagement with an infusion pump, wherein during or after engagement the member assumes a fluid delivery position to allow flow of the fluid through the tube, while before or as the cassette is removed from the pump, the member assumes the fluid non-delivery position to prevent flow of fluid through the tubing.

In an embodiment, the anti-flow valve mechanism is associated with the tube, cassette or housing or is situated in or near the cassette or housing and includes a moveable member and a force-applying member. The member may be a tab member that is moveable between the fluid non-delivery position and the fluid delivery position, wherein prior to engagement of the housing with the pump, the tab member and moveable member are in the fluid non-delivery position whereas during or after engagement the tab member overcomes the force-applying member bias and moves the moveable member to the fluid delivery position.

In an embodiment, the tab member moves the moveable member to the fluid delivery position as the cassette engages the infusion pump to allow flow of fluid through the tubing and as the cassette is removed from the pump the tab member is released so that the moveable member returns to the fluid non-delivery position to prevent flow of fluid through the tubing such that movement of the tab member between the fluid non-delivery position and the fluid delivery position changes the biasing of the force-applying member.

In an embodiment, the tab member moves the moveable member to the fluid delivery position after the cassette engages the infusion pump to allow flow of fluid through the tubing, and before the cassette is removed from the pump the tab member is released so that the moveable member returns to the fluid non-delivery position to prevent flow of fluid through the tubing such that movement of the tab member between the fluid non-delivery position and the fluid delivery position changes the biasing of the force-applying member.

In an embodiment, the housing has an essentially rectangular shape and is configured and dimensioned to fit within an opening in the infusion pump, and the length of tubing is initially held between the ends of the cassette in a straight line and in front of a rigid curved wall of the housing such that when engaged with the pumping mechanism of the pump, the length of tubing is accurately positioned in contact with and between the curved wall and the pumping mechanism.

In an embodiment, the force-applying member includes a compression spring and the moveable member of the anti-flow valve mechanism includes a pinch head that has a relatively larger cross-sectional surface that contacts the force-applying member and a relatively narrower cross-sectional surface contacting the tubing that concentrates the force of the force-applying member against the tubing.

In an embodiment, the housing includes registration grooves for alignment of the cassette during engagement with the infusion pump, and the housing includes at least one window adjacent the tubing to allow monitoring or detection of fluid flow therethrough.

In an embodiment, the housing is made of molded plastic, the tubing is made of an elastomeric or silicone material, and the tubing is held between inlet and outlet tubing supports in the housing, wherein each tubing support includes a male junction and a female junction, wherein in the inlet support the male junction is configured and dimensioned to fit inside the tubing and the female junction is configured and dimensioned to receive tubing extending to a fluid supply, and in the outlet support, the male junction is configured and dimensioned to fit inside the tubing and the female junction is configured and dimensioned to receive the length of tubing that extends to the subject.

In an embodiment, the anti-flow valve means includes a base including holding means for holding the tube in operative engagement with the base, a first clamping surface and supporting means for supporting a connector, a clamping element having a second clamping surface engageable with the tube and moveable between an open position allowing flow of fluid through the tube and a closed position wherein the tube is occluded by the clamping element, a connector for connecting the tube with a-port on a patient, the connector being removable from the pinch clamp assembly, and a spring. The connector may be adapted to engage with the clamping element so as to hold the clamping element in the open position, and the clamping element is forced from the open to the closed position by the force of the spring as soon as the connector is removed from the assembly, and the clamping element is adapted to be moved from the closed to the open position when the pinch clamp assembly is mounted to the enteral feeding or infusion pump and the connector is removed. The clamping element may be hinged at the base.

In an embodiment, the connector is selected from the group consisting of an enteral spike, an IV spike, an enteral feeding adapter, an IV luer lock adapter, another enteral or IV component, or combinations thereof. The connector may be threadedly coupled to the clamping element and/or the supporting means.

In an embodiment, the base is formed as a cassette such that the pinch clamp assembly may be integrally mounted to the enteral feeding or infusion pump. The base, the clamping element and the connector may be made of recyclable plastic material such as thermoplastics, and the spring may be made of metal. The tube may be made of silicone.

In an embodiment, the base includes a cylindrically-shaped holding element to accommodate a spring.

In an embodiment, the clamping element includes a first leg with a tube blocking portion, a second leg having means for engagement with the spring and a retainer for engagement with the connector, and a swivel pin adapted to engage with a suitable seating on the base. The retainer may be constructed as a cap which is adapted to accommodate the tip of the connector.

In an embodiment, the first and/or second clamping surfaces are uneven, corrugated or finned.

In an embodiment, the base includes a first and a second inner wall between which the clamping element is arranged.

In an embodiment, the anti-flow valve means includes a housing having a constrictor, a tube attached to the housing and positioned through the constrictor, and a ball located inside the tube. The constrictor may be so constructed and arranged to prevent the ball from moving through the tube at a location proximate the constrictor. The tube may include a first end attached to an inlet port and a second end attached to an outlet port. The inlet port is sized to prevent the ball from entering the inlet port.

In an embodiment, the anti-flow valve means includes a housing having a flow restrictor with a locking member and a spring, and a tube attached to the housing and positioned adjacent the flow restrictor. The locking member may be so constructed and arranged to rotate when inserted into a pumping device.

In an embodiment, the housing further includes a stopper positioned adjacent the tube and on an opposite side of the tube from the flow restrictor. The flow restrictor and the stopper may occlude the tube when the flow restrictor is in a resting position. The flow restrictor and the stopper allow a fluid to flow through the tube when the flow restrictor is in an actuated position.

In an embodiment, at least a portion of the tube is flexible.

In an embodiment, the cassette includes a projection on a top surface of the housing. The projection may be substantially cylindrically shaped and may be located in the middle of a length of the housing. The projection may be located on an outer portion of the top surface of the housing. The projection is so constructed and arranged to cooperate with a latch mechanism of a pumping device to lock the cassette into place in the pumping device.

In an embodiment, the cassette includes a notch on at least one edge of a housing. The edge is contiguous to a recessed area of a cassette housing. The notch may have a shape selected from the group consisting of semi-circular, "V"-shaped, oblong, square, rectangular, or combinations thereof. In an embodiment, the notch is substantially "V"-shaped. The "V"-shape is defined by a cut-away portion and a beveled portion of the edge. The notch may be so constructed and arranged to partially receive a tube when the cassette is inserted into a pumping device.

In an embodiment, the cassette includes at least one tab member on a side wall of a cassette housing. The cassette may also include at least one tab member on at least two sides of the cassette. The tab members may be so constructed and arranged to communicate with ledges on an interior wall of a pumping device to guide the cassette during insertion into the pumping device. The tab members have a shape selected from the group consisting of semi-circular, square, rectangular, oblong, triangular, wing-shaped, or combinations thereof. In an embodiment, the tab members are substantially wing-shaped. The tab members may be formed integrally with the cassette, or may be adhered to a side of the cassette.

In an embodiment, the cassette includes at least one directional indicator. The directional indicator is located on a surface of a cassette housing. The directional indicator is an indicator selected from the group consisting of letters, written indicators, logos, symbols, numbers, or combinations thereof. In an embodiment, the cassette includes at least two directional indicators. The directional indicator may be a sticker that is adhered to a wall of a cassette housing. The directional indicator may be applied to a wall of a housing of the cassette using a technique selected from the group consisting of etching, lasering, molding, forming, or combinations thereof. The directional indicator is indicative of a proper orientation of the cassette when the cassette is inserted into a pumping device.

In an embodiment, a method of improving the safe use of an infusion pump for pumping fluid into a patient is provided. The method includes providing a cassette configured for use with the infusion pump, the cassette including a flexible tube, a housing, and at least two components selected from the group consisting of an air-in-line sensor device, a false reading component for an air-in-line sensor device, an occlusion sensor device, a false reading component for an occlusion sensor device, a latch sensor device, a false reading component for a latch sensor device, anti-flow valve means, a projection located on a top surface of the housing, at least one notch on an edge of the housing, at least one tab member located on an exterior of the housing, a directional indicator on a surface of the housing, or combinations thereof.

In an embodiment, the cassette housing includes a recessed area so constructed and arranged to receive a portion of a pumping device. The housing may also include first and second ends for holding the flexible tube.

In an embodiment, the cassette includes an air-in-line sensor device. The air-in-line sensor device may include a detection chamber, which may be so constructed and arranged for receiving a portion of the flexible tube. The detection chamber can include a window for allowing infra-red light transmission to pass therethrough. The detection chamber may have more than one window. In an embodiment, the detection chamber is made from a molded, plastic chamber that is so constructed and arranged to hold the flexible tube. In an embodiment, the detection chamber is made from a transparent polyvinyl chloride material. The detection chamber may also have a at least a portion that includes an infra-red transparent surface, or at least a portion that includes an infra-red blocking material. The detection chamber may be attached to the cassette and may have two ends, each end being configured to attach to the flexible tube.

In an embodiment, the cassette includes a false reading component for an air-in-line sensor device. The false reading component for the air-in-line sensor device may be made from a material selected from the group consisting of white paper, a metallic surface, infra-red reflective plastic, infra-red reflective glass, infra-red reflective paint, infra-red reflective tape, or combinations thereof. The false reading component for the air-in-line sensor device may be located between flexible tube and a side of the cassette facing an interior of a pump when the cassette is inserted into a pumping device. In an embodiment, the false reading component for the air-in-line sensor device is a piece of infra-red reflective plastic.

In an embodiment, the cassette includes an occlusion sensor device. The occlusion sensor device may include a tube made from a material selected from the group consisting of opaque, infra-red reflective, or combinations thereof, and a bias bump located adjacent to a portion of the tube. The tube may have opaque walls. Alternatively, the at least a portion of the tube may include an infra-red reflective surface.

In an embodiment, the tube is configured to expand or contract in response to a fluid pressure therein and may be contained within a tube housing that defines a window. The tube housing can be formed integrally with the cassette. The tube housing may be formed from opaque polyvinyl chloride, or may have at least a portion of the tube housing including an infra-red transparent surface. In an embodiment, at least a portion of the tube housing includes an infra-red absorbing material.

In an embodiment, the bias bump is substantially rigid to prevent the tube from expanding past bias bump.

In an embodiment, the tube is part of an enteral feeding tube set.

In an embodiment, the cassette includes a false reading component for an occlusion sensor device. The false reading component for the occlusion sensor device includes a material selected from the group consisting of white paper, a metallic surface, infra-red reflective plastic, infra-red reflective glass, infra-red reflective paint, infra-red reflective tape, or combinations thereof. The false reading component for the occlusion sensor device is located between the tube and a side of the cassette facing an interior of a pump when the cassette is inserted into a pumping device. In an embodiment, the false reading component for the occlusion sensor device is a piece of infra-red reflective plastic.

In an embodiment, the cassette includes a latch sensor device. The latch sensor device may include a cassette housing having at least a portion of an infra-red reflective material that is so constructed and arranged to communicate with an infra-red sensor of a pumping device when the cassette is inserted into the pumping device.

In an embodiment, the cassette includes a false reading component for a latch sensor device. The false reading component for the latch sensor device includes a material selected from the group consisting of white paper, a metallic surface, infra-red reflective plastic, infra-red reflective glass, infra-red reflective paint, infra-red reflective tape, or combinations thereof. The false reading component for the latch sensor device is located between an infra-red reflective material of a housing of the cassette and an interior of a pump when the cassette is inserted into a pumping device. In an embodiment, the false reading component for the latch sensor device is a piece of infra-red reflective plastic.

In an embodiment, the cassette includes anti-flow valve means.

In an embodiment, the anti-flow valve means includes an anti-flow valve mechanism that is biased against the flexible tube in a fluid non-delivery position to prevent flow therethough, and a member operatively associated with the anti-flow valve mechanism to overcome the force-applying member bias to allow flow of fluid through the tube when the housing is engaged with a pump. The housing may be configured and dimensioned for engagement with an infusion pump, wherein during or after engagement the member assumes a fluid delivery position to allow flow of the fluid through the tube, while before or as the cassette is removed from the pump, the member assumes the fluid non-delivery position to prevent flow of fluid through the tubing.

In an embodiment, the anti-flow valve mechanism is associated with the tube, cassette or housing or is situated in or near the cassette or housing and includes a moveable member and a force-applying member. The member may be a tab member that is moveable between the fluid non-delivery position and the fluid delivery position, wherein prior to engagement of the housing with the pump, the tab member and moveable member are in the fluid non-delivery position whereas during or after engagement the tab member overcomes the force-applying member bias and moves the movable member to the fluid delivery position.

In an embodiment, the tab member moves the moveable member to the fluid delivery position as the cassette engages the infusion pump to allow flow of fluid through the tubing and as the cassette is removed from the pump the tab member is released so that the moveable member returns to the fluid non-delivery position to prevent flow of fluid through the tubing such that movement of the tab member between the fluid non-delivery position and the fluid delivery position changes the biasing of the force-applying member.

In an embodiment, the tab member moves the moveable member to the fluid delivery position after the cassette engages the infusion pump to allow flow of fluid through the tubing, and before the cassette is removed from the pump the tab member is released so that the moveable member returns to the fluid non-delivery position to prevent flow of fluid through the tubing such that movement of the tab member between the fluid non-delivery position and the fluid delivery position changes the biasing of the force-applying member.

In an embodiment, the housing has an essentially rectangular shape and is configured and dimensioned to fit within an opening in the infusion pump, and the length of tubing is initially held between the ends of the cassette in a straight line and in front of a rigid curved wall of the housing such that when engaged with the pumping mechanism of the pump, the length of tubing is accurately positioned in contact with and between the curved wall and the pumping mechanism.

In an embodiment, the force-applying member includes a compression spring and the moveable member of the anti-flow valve mechanism includes a pinch head that has a relatively larger cross-sectional surface that contacts the force-applying member and a relatively narrower cross-sectional surface contacting the tubing that concentrates the force of the force-applying member against the tubing.

In an embodiment, the housing includes registration grooves for alignment of the cassette during engagement with the infusion pump, and the housing includes at least one window adjacent the tubing to allow monitoring or detection of fluid flow therethrough.

In an embodiment, the housing is made of molded plastic, the tubing is made of an elastomeric or silicone material, and the tubing is held between inlet and outlet tubing supports in the housing, wherein each tubing support includes a male junction and a female junction, wherein in the inlet support the male junction is configured and dimensioned to fit inside the tubing and the female junction is configured and dimensioned to receive tubing extending to a fluid supply, and in the outlet support, the male junction is configured and dimensioned to fit inside the tubing and the female junction is configured and dimensioned to receive the length of tubing that extends to the subject.

In an embodiment, the anti-flow valve means includes a base including holding means for holding the tube in operative engagement with the base, a first clamping surface and supporting means for supporting a connector, a clamping element having a second clamping surface engageable with the tube and moveable between an open position allowing flow of fluid through the tube and a closed position wherein the tube is occluded by the clamping element, a connector for connecting the tube with a-port on a patient, the connector being removable from the pinch clamp assembly, and a spring. The connector may be adapted to engage with the clamping element so as to hold the clamping element in the open position, and the clamping element is forced from the open to the closed position by the force of the spring as soon as the connector is removed from the assembly, and the clamping element is adapted to be moved from the closed to the open position when the pinch clamp assembly is mounted to the enteral feeding or infusion pump and the connector is removed. The clamping element may be hinged at the base.

In an embodiment, the connector is selected from the group consisting of an enteral spike, an IV spike, an enteral feeding adapter, an IV luer lock adapter, another enteral or IV component, or combinations thereof. The connector may be threadedly coupled to the clamping element and/or the supporting means.

In an embodiment, the base is formed as a cassette such that the pinch clamp assembly may be integrally mounted to the enteral feeding or infusion pump. The base, the clamping element and the connector may be made of recyclable plastic material such as thermoplastics, and the spring may be made of metal. The tube may be made of silicone.

In an embodiment, the base includes a cylindrically-shaped holding element to accommodate a spring.

In an embodiment, the clamping element includes a first leg with a tube blocking portion, a second leg having means for engagement with the spring and a retainer for engagement with the connector, and a swivel pin adapted to engage with a suitable seating on the base. The retainer may be constructed as a cap which is adapted to accommodate the tip of the connector.

In an embodiment, the first and/or second clamping surfaces are uneven, corrugated or finned.

In an embodiment, the base includes a first and a second inner wall between which the clamping element is arranged.

In an embodiment, the anti-flow valve means includes a housing having a constrictor, a tube attached to the housing and positioned through the constrictor, and a ball located inside the tube. The constrictor may be so constructed and arranged to prevent the ball from moving through the tube at a location proximate the constrictor. The tube may include a first end attached to an inlet port and a second end attached to an outlet port. The inlet port is sized to prevent the ball from entering the inlet port.

In an embodiment, the anti-flow valve means includes a housing having a flow restrictor with a locking member and a spring, and a tube attached to the housing and positioned adjacent the flow restrictor. The locking member may be so constructed and arranged to rotate when inserted into a pumping device.

In an embodiment, the housing further includes a stopper positioned adjacent the tube and on an opposite side of the tube from the flow restrictor. The flow restrictor and the stopper may occlude the tube when the flow restrictor is in a resting position. The flow restrictor and the stopper allow a fluid to flow through the tube when the flow restrictor is in an actuated position.

In an embodiment, at least a portion of the tube is flexible.

In an embodiment, the cassette includes a projection on a top surface of the housing. The projection may be substantially cylindrically shaped and may be located in the middle of a length of the housing. The projection may be located on an outer portion of the top surface of the housing. The projection is so constructed and arranged to cooperate with a latch mechanism of a pumping device to lock the cassette into place in the pumping device.

In an embodiment, the cassette includes a notch on at least one edge of a housing. The edge is contiguous to a recessed area of a cassette housing. The notch may have a shape selected from the group consisting of semi-circular, "V"-shaped, oblong, square, rectangular, or combinations thereof. In an embodiment, the notch is substantially "V"-shaped. The "V"-shape is defined by a cut-away portion and a beveled portion of the edge. The notch may be so constructed and arranged to partially receive a tube when the cassette is inserted into a pumping device.

In an embodiment, the cassette includes at least one tab member on a side wall of a cassette housing. The cassette may also include at least one tab member on at least two sides of the cassette. The tab members may be so constructed and arranged to communicate with ledges on an interior wall of a pumping device to guide the cassette during insertion into the pumping device. The tab members have a shape selected from the group consisting of semi-circular, square, rectangular, oblong, triangular, wing-shaped, or combinations thereof. In an embodiment, the tab members are substantially wing-shaped. The tab members may be formed integrally with the cassette, or may be adhered to a side of the cassette.

In an embodiment, the cassette includes at least one directional indicator. The directional indicator is located on a surface of a cassette housing. The directional indicator is an indicator selected from the group consisting of letters, written indicators, logos, symbols, numbers, or combinations thereof. In an embodiment, the cassette includes at least two directional indicators. The directional indicator may be a sticker that is adhered to a wall of a cassette housing. The directional indicator may be applied to a wall of a housing of the cassette using a technique selected from the group consisting of etching, lasering, molding, forming, or combinations thereof. The directional indicator is indicative of a proper orientation of the cassette when the cassette is inserted into a pumping device.

In yet another embodiment, a cassette is provided and includes a flexible tube, a housing, and an anti-free flow valve mechanism. The anti-free flow mechanism includes a cap having an actuating portion and a valve arm having a tube blocking portion.

In an embodiment, the cap has a shape selected from the group consisting of substantially cylindrical, rectangular, spherical, or combinations thereof. The cap may be located on an outside, distal end of the cassette or may be located on an inside, bottom of the cassette.

In an embodiment, the actuating portion of the cap extends from the cap in a direction that is substantially perpendicular to a length of the cap. The actuating portion of the cap may have a shape selected from the group consisting of substantially cylindrical, rectangular, triangular, spherical, or combinations thereof. The actuating portion of the cap may also have a notched portion at an end of the actuating portion away from the cap. The notched portion of the actuating portion is configured to engage at least a portion of the valve arm. The actuating portion of the cap may be configured for insertion into a hole in the cassette.

In an embodiment, the cassette further includes a stopper configured to abut against the cap when the actuating portion of the cassette is inserted into the hole. The stopper has a shape selected from the group consisting of substantially circular, triangular, rectangular, or combinations thereof. The stopper extends from the cassette in a direction that is substantially perpendicular to a length of the cassette.

In an embodiment, the cap is substantially hollow and is configured to receive a portion of the flexible tube.

In an embodiment, the valve arm includes a tube-retaining portion. The tube-retaining portion may extend from a front end of the valve arm. The tube-retaining portion may also extend in a direction that is substantially perpendicular to a length of the valve arm.

In an embodiment, the valve arm includes a connector portion that is so constructed and arranged to engage a connecting element of the cassette. The connector portion has a shape selected from the group consisting of substantially "C"-shaped, circular, rectangular, hemi-spherical, or combinations thereof. The connector portion of the valve arm may be configured to rotate about the connecting element of the cassette.

In an embodiment, the connecting element of the cassette may include a bar that resides in and connects two opposing sides of a hole in the cassette. The bar may have a shape selected from the group consisting of substantially cylindrical, rectangular, or combinations thereof.

In an embodiment, the valve arm includes a projection on a top side of the valve arm. The projection may be configured to interact with a tab member of a pumping device when the cassette is inserted into the pumping device. The tab member cooperates with the projection of the valve arm to overcome a blocked position bias of the valve arm and to move the valve arm to a free-flow position.

In still yet another embodiment, a cassette is provided and includes a flexible tube, a housing, and an anti-free flow valve mechanism. The anti-free flow mechanism includes a cap having an actuating portion, a luer having a hook portion, and a valve arm having a tube blocking portion.

In an embodiment, the cap has a shape selected from the group consisting of substantially cylindrical, rectangular, spherical, or combinations thereof. The cap may be located on an outside, distal end of the cassette. The cap may also be located on an inside, bottom of the cassette.

In an embodiment, the actuating portion of the cap extends from the cap in a direction that is substantially perpendicular to a length of the cap. The actuating portion of the cap has a shape selected from the group consisting of substantially cylindrical, rectangular, triangular, spherical, or combinations thereof.

In an embodiment, the actuating portion of the cap includes a notched portion at an end of the actuating portion away from the cap. The notched portion of the actuating portion is configured to engage at least a portion of the valve arm.

In an embodiment, the actuating portion of the cap is configured for insertion into a first hole in a distal end of the cassette.

In an embodiment, the cap is substantially hollow and is configured to receive an end of the luer. The luer includes a threaded portion that is configured to engage a corresponding threaded portion of a patient line for use with a therapy. The luer also includes a fin portion for gripping and rotating the luer. The hook portion of the luer is configured to be inserted into a second hole in a distal end of the cassette. Generally, the luer is configured to be inserted into a hollow portion of the cap prior use of the cassette for a therapy.

In an embodiment, the valve arm includes a tube-retaining portion. The tube-retaining portion may extend from a front end of the valve arm. The tube-retaining portion may also extend in a direction that is substantially perpendicular to a length of the valve arm.

In an embodiment, the valve arm includes a connector portion that is so constructed and arranged to engage a connecting element of the cassette. The connector portion has a shape selected from the group consisting of substantially "C"-shaped, circular, rectangular, hemi-spherical, or combinations thereof. The connector portion of the valve arm is configured to rotate about the connecting element of the cassette.

In an embodiment, the connecting element of the cassette includes a bar that resides in and connects two opposing sides of a hole in the cassette. The bar may have a shape selected from the group consisting of substantially cylindrical, rectangular, or combinations thereof.

In an embodiment, the valve arm includes a projection on a top side of the valve arm. The projection is configured to interact with a tab member of a pumping device when the cassette is inserted into the pumping device. The tab member cooperates with the projection of the valve arm to overcome a blocked position bias of the valve arm and move the valve arm to a free-flow position.

In another embodiment, a cassette is provided and includes a flexible tubing, a housing, and an anti-free flow mechanism. The anti-free flow mechanism includes a luer having an actuating portion, a cap, and a valve arm having a tube blocking portion.

In an embodiment, the cap has a shape selected from the group consisting of substantially cylindrical, rectangular, spherical, or combinations thereof. The cap may be located on an outside, distal end of the cassette. The cap may also be located on an inside, bottom of the cassette.

In an embodiment, the cap is substantially hollow and is configured to receive an end of the luer. The luer may have a tapered shape that is configured to engage a patient line for use with a therapy. The actuating portion of the luer extends from the luer in a direction that is substantially parallel to a length of the luer. The actuating portion of the luer has a shape selected from the group consisting of substantially cylindrical, rectangular, triangular, spherical, or combinations thereof. The actuating portion of the luer is configured for insertion into at least one bracket of the cassette. The luer is configured to be inserted into a hollow portion of the cap prior use of the cassette for a therapy.

In an embodiment, the valve arm includes a tube-retaining portion. The tube-retaining portion may extend from a front end of the valve arm. The tube-retaining portion may also extend in a direction that is substantially perpendicular to a length of the valve arm.

In an embodiment, the valve arm includes a connector portion that is so constructed and arranged to engage a connecting element of the cassette. The connector portion has a shape selected from the group consisting of substantially "C"-shaped, circular, rectangular, hemi-spherical, or combinations thereof. The connector portion may include two coaxial, spherical portions on opposing sides of the valve arm.

In an embodiment, the connecting element of the cassette may include a bar that resides in and connects two opposing sides of a hole in the cassette. The bar has a shape selected from the group consisting of substantially cylindrical, rectangular, or combinations thereof.

In an embodiment, the connecting element of the cassette includes first and second pegs located on opposing sides of a hole in the cassette.

In an embodiment, the connector portion of the valve arm is configured to rotate about the connecting element of the cassette.

In an embodiment, the valve arm includes a projection on a top side of the valve arm. The projection is configured to interact with a tab member of a pumping device when the cassette is inserted into the pumping device. The tab member cooperates with the projection of the valve arm to overcome a blocked position bias of the valve arm and move the valve arm to a free-flow position.

In yet another embodiment, a method of providing fluid to a patient is provided. The method includes the steps of removing an actuating portion of a cap from a cassette, disconnecting an end portion of the flexible tube from the cap, connecting the end portion of the flexible tube to a patient line, and pumping fluid into the patient using the cassette. The cassette includes a flexible tube, a housing, and a valve arm having a tube blocking portion.

In an embodiment, the method includes allowing the valve arm to return to a biased tube blocking position when the actuating portion of the cap is removed from the cassette.

In an embodiment, the actuating portion of the cap is so constructed and arranged to engage a portion of the valve arm.

In an embodiment, the cap has a shape selected from the group consisting of substantially cylindrical, rectangular, spherical, or combinations thereof. The cap may be located on an outside, distal end of the cassette. The cap may also be located on an inside, bottom of the cassette. The actuating portion of the cap extends from the cap in a direction that is substantially perpendicular to a length of the cap. The actuating portion of the cap has a shape selected from the group consisting of substantially cylindrical, rectangular, triangular, spherical, or combinations thereof.

In an embodiment, the actuating portion of the cap includes a notched portion at an end of the actuating portion away from the cap. The notched portion of the actuating portion is configured to engage at least a portion of the valve arm.

In an embodiment, the actuating portion of the cap is configured for insertion into a hole in the cassette.

In an embodiment, the cassette further includes a stopper configured to abut against the cap when the actuating portion of the cassette is inserted into the hole. The stopper has a shape selected from the group consisting of substantially circular, triangular, rectangular, or combinations thereof. The stopper extends from the cassette in a direction that is substantially perpendicular to a length of the cassette.

In an embodiment, the cap is substantially hollow and is configured to receive an end of a patient tubing line.

In an embodiment, the valve arm includes a tube-retaining portion. The tube-retaining portion may extend from a front end of the valve arm. The tube-retaining portion may also extend in a direction that is substantially perpendicular to a length of the valve arm.

In an embodiment, the valve arm includes a connector portion that is so constructed and arranged to engage a connecting element of the cassette. The connector portion has a shape selected from the group consisting of substantially "C"-shaped, circular, rectangular, hemi-spherical, or combinations thereof.

In an embodiment, the connecting element of the cassette includes a bar that resides in and connects two opposing sides of a hole in the cassette. The bar includes a shape selected from the group consisting of substantially cylindrical, rectangular, or combinations thereof.

In an embodiment, the connector portion of the valve arm is configured to rotate about the connecting element of the cassette.

In an embodiment, the valve arm includes a projection on a top side of the valve arm. The projection is configured to interact with a tab member of a pumping device when the cassette is inserted into the pumping device. The tab member cooperates with the projection of the valve arm to overcome a blocked position bias of the valve arm and move the valve arm to a free-flow position.

In still yet another embodiment, a method of improving the safe use of an infusion pump for pumping fluid into a patient is provided. The method includes providing a cassette configured for use with the infusion pump, the cassette including a flexible tube, a housing, a valve arm having a tube blocking portion, and a cap having an actuating portion so constructed and arranged to engage a portion of the valve arm.

In an embodiment, the cap has a shape selected from the group consisting of substantially cylindrical, rectangular, spherical, or combinations thereof.

In an embodiment, the cap may be located on an outside, distal end of the cassette. The cap may also be located on an inside, bottom of the cassette.

In an embodiment, the actuating portion of the cap extends from the cap in a direction that is substantially perpendicular to a length of the cap. The actuating portion of the cap has a shape selected from the group consisting of substantially cylindrical, rectangular, triangular, spherical, or combinations thereof.

In an embodiment, the actuating portion of the cap includes a notched portion at an end of the actuating portion away from the cap. The notched portion of the actuating portion is configured to engage at least a portion of the valve arm.

In an embodiment, the actuating portion of the cap is configured for insertion into a hole in the cassette.

In an embodiment, the cassette further includes a stopper configured to abut against the cap when the actuating portion of the cassette is inserted into the hole. The stopper has a shape selected from the group consisting of substantially circular, triangular, rectangular, or combinations thereof. The stopper extends from the cassette in a direction that is substantially perpendicular to a length of the cassette.

In an embodiment, the cap is substantially hollow and is configured to receive an end of a patient tubing line.

In an embodiment, the valve arm includes a tube-retaining portion. The tube-retaining portion may extend from a front end of the valve arm. The tube-retaining portion may also extend in a direction that is substantially perpendicular to a length of the valve arm.

In an embodiment, the valve arm includes a connector portion that is so constructed and arranged to engage a connecting element of the cassette. The connector portion has a shape selected from the group consisting of substantially "C"-shaped, circular, rectangular, hemi-spherical, or combinations thereof.

In an embodiment, the connecting element of the cassette includes a bar that resides in and connects two opposing sides of a hole in the cassette. The bar has a shape selected from the group consisting of substantially cylindrical, rectangular, or combinations thereof.

In an embodiment of the method, the connector portion of the valve arm is configured to rotate about the connecting element of the cassette.

In an embodiment, the valve arm includes a projection on a top side of the valve arm. The projection is configured to interact with a tab member of a pumping device when the cassette is inserted into the pumping device. The tab member cooperates with the projection of the valve arm to overcome a blocked position bias of the valve arm and move the valve arm to a free-flow position.

In yet another embodiment, a method of providing fluid to a patient is provided. The method includes the steps of removing an actuating portion of a cap and a hook portion of a luer from a cassette, disconnecting the luer from the cap, connecting the luer to a patient line, and pumping fluid into the patient using the cassette. The cassette includes a flexible tube, a housing, and a valve arm having a tube blocking portion.

In an embodiment, the cap has a shape selected from the group consisting of substantially cylindrical, rectangular, spherical, or combinations thereof. The cap may be located on an outside, distal end of the cassette. The cap may also be located on an inside, bottom of the cassette.

In an embodiment, the actuating portion of the cap extends from the cap in a direction that is substantially perpendicular to a length of the cap. The actuating portion of the cap has a shape selected from the group consisting of substantially cylindrical, rectangular, triangular, spherical, and combinations thereof.

In an embodiment, the actuating portion of the cap includes a notched portion at an end of the actuating portion away from the cap. The notched portion of the actuating portion is configured to engage at least a portion of the valve arm.

In an embodiment, the actuating portion of the cap is configured for insertion into a first hole in a distal end of the cassette.

In an embodiment, the cap is substantially hollow and is configured to receive an end of the luer. The luer includes a threaded portion that is configured to engage a corresponding threaded portion of a patient line for use with a therapy. The luer includes a fin portion for gripping and rotating the luer. The hook portion is configured to be inserted into a second hole in a distal end of the cassette.

In an embodiment, the luer is configured to be inserted into a hollow portion of the cap prior use of the cassette for a therapy.

In an embodiment, the valve arm includes a tube-retaining portion. The tube-retaining portion may extend from a front end of the valve arm. The tube-retaining portion may extend in a direction that is substantially perpendicular to a length of the valve arm.

In an embodiment, the valve arm includes a connector portion that is so constructed and arranged to engage a connecting element of the cassette. The connector portion has a shape selected from the group consisting of substantially "C"-shaped, circular, rectangular, hemi-spherical, or combinations thereof. The connector portion of the valve arm is configured to rotate about the connecting element of the cassette.

In an embodiment, the connecting element of the cassette includes a bar that resides in and connects two opposing sides of a hole in the cassette. The bar has a shape selected from the group consisting of substantially cylindrical, rectangular, or combinations thereof.

In an embodiment, the valve arm includes a projection on a top side of the valve arm. The projection is configured to interact with a tab member of a pumping device when the cassette is inserted into the pumping device. The tab member cooperates with the projection of the valve arm to overcome a blocked position bias of the valve arm and move the valve arm to a free-flow position.

In another embodiment, a method of improving the safe use of an infusion pump for pumping fluid into a patient is provided. The method includes the steps of providing a cassette configured for use with the infusion pump, the cassette including a flexible tube, a housing, a valve arm having a tube blocking portion, a cap having an actuating portion so constructed and arranged to engage a portion of the valve arm, and a luer having a hook portion.

In an embodiment, the cap has a shape selected from the group consisting of substantially cylindrical, rectangular, spherical, or combinations thereof. The cap may be located on an outside, distal end of the cassette. The cap may also be located on an inside, bottom of the cassette.

In an embodiment, the actuating portion of the cap extends from the cap in a direction that is substantially perpendicular to a length of the cap. The actuating portion of the cap has a shape selected from the group consisting of substantially cylindrical, rectangular, triangular, spherical, or combinations thereof.

In an embodiment, the actuating portion of the cap includes a notched portion at an end of the actuating portion away from the cap. The notched portion of the actuating portion is configured to engage at least a portion of the valve arm.

In an embodiment, the actuating portion of the cap is configured for insertion into a first hole in a distal end of the cassette.

In an embodiment, the cap is substantially hollow and is configured to receive an end of the luer. The luer includes a threaded portion that is configured to engage a corresponding threaded portion of a patient line for use with a therapy. The luer includes a fin portion for gripping and rotating the luer. The hook portion is configured to be inserted into a second hole in a distal end of the cassette.

In an embodiment, the luer is configured to be inserted into a hollow portion of the cap prior use of the cassette for a therapy.

In an embodiment, the valve arm includes a tube-retaining portion. The tube-retaining portion may extend from a front end of the valve arm. The tube-retaining portion may also extend in a direction that is substantially perpendicular to a length of the valve arm.

In an embodiment, the valve arm includes a connector portion that is so constructed and arranged to engage a connecting element of the cassette. The connector portion has a shape selected from the group consisting of substantially "C"-shaped, circular, rectangular, hemi-spherical, or combinations thereof.

In an embodiment, the connecting element of the cassette includes a bar that resides in and connects two opposing sides of a hole in the cassette. The bar has a shape selected from the group consisting of substantially cylindrical, rectangular, or combinations thereof.

In an embodiment, the connector portion of the valve arm is configured to rotate about the connecting element of the cassette.

In an embodiment, the valve arm includes a projection on a top side of the valve arm. The projection is configured to interact with a tab member of a pumping device when the cassette is inserted into the pumping device. The tab member cooperates with the projection of the valve arm to overcome a blocked position bias of the valve arm and move the valve arm to a free-flow position.

In still yet another embodiment, a method of providing fluid to a patient is provided. The method includes the steps of removing an actuating portion of a luer from a cassette, disconnecting the luer from a cap, connecting the luer to a patient line, and pumping fluid into the patient using the cassette. The cassette includes a flexible tube, a housing, and a valve arm having a tube blocking portion.

In an embodiment, the cap has a shape selected from the group consisting of substantially cylindrical, rectangular, spherical, or combinations thereof. The cap may be located on an outside, distal end of the cassette. The cap may also be located on an inside, bottom of the cassette.

In an embodiment, the cap is substantially hollow and is configured to receive an end of the luer.

In an embodiment, the luer has a tapered shape that is configured to engage a patient line for use with a therapy.

In an embodiment, the actuating portion of the luer extends from the luer in a direction that is substantially parallel to a length of the luer. The actuating portion of the luer has a shape selected from the group consisting of substantially cylindrical, rectangular, triangular, spherical, or combinations thereof. The actuating portion of the luer is configured for insertion into at least one bracket located on the cassette.

In an embodiment, the luer is configured to be inserted into a hollow portion of the cap prior use of the cassette for a therapy.

In an embodiment, the valve arm includes a tube-retaining portion. The tube-retaining portion extends from a front end of the valve arm. The tube-retaining portion extends in a direction that is substantially perpendicular to a length of the valve arm.

In an embodiment, the valve arm includes a connector portion that is so constructed and arranged to engage a connecting element of the cassette. The connector portion has a shape selected from the group consisting of substantially "C"-shaped, circular, rectangular, hemi-spherical, or combinations thereof.

In an embodiment, the connector portion includes two coaxial, spherical portions on opposing sides of the valve arm.

In an embodiment, the connecting element of the cassette includes a bar that resides in and connects two opposing sides of a hole in the cassette. The bar includes a shape selected from the group consisting of substantially cylindrical, rectangular, or combinations thereof.

In an embodiment, the connecting element of the cassette includes first and second pegs located on opposite sides of a hole in the cassette.

In an embodiment, the connector portion of the valve arm is configured to rotate about the connecting element of the cassette.

In an embodiment, the valve arm includes a projection on a top side of the valve arm. The projection is configured to interact with a tab member of a pumping device when the cassette is inserted into the pumping device. The tab member cooperates with the projection of the valve arm to overcome a blocked position bias of the valve arm and move the valve arm to a free-flow position.

In yet another embodiment, a method of improving the safe use of an infusion pump for pumping fluid into a patient is provided. The method includes the steps of providing a cassette configured for use with the infusion pump, the cassette including a flexible tube, a housing, a valve arm having a tube blocking portion, a cap, and a luer having an actuating portion so constructed and arranged to engage a portion of the valve arm.

In an embodiment, the cap has a shape selected from the group consisting of substantially cylindrical, rectangular, spherical, or combinations thereof. The cap may be located on an outside, distal end of the cassette. The cap may also be located on an inside, bottom of the cassette.

In an embodiment, the cap is substantially hollow and is configured to receive an end of the luer. The luer has a tapered shape that is configured to engage a patient line for use with a therapy. The actuating portion of the luer extends from the luer in a direction that is substantially parallel to a length of the luer.

In an embodiment, the actuating portion of the luer has a shape selected from the group consisting of substantially cylindrical, rectangular, triangular, spherical, or combinations thereof. The actuating portion of the luer is configured for insertion into at least one bracket located on the cassette.

In an embodiment, the luer is configured to be inserted into a hollow portion of the cap prior use of the cassette for a therapy.

In an embodiment, the valve arm includes a tube-retaining portion. The tube-retaining portion extends from a front end of the valve arm. The tube-retaining portion extends in a direction that is substantially perpendicular to a length of the valve arm.

In an embodiment, the valve arm includes a connector portion that is so constructed and arranged to engage a connecting element of the cassette. The connector portion includes a shape selected from the group consisting of substantially "C"-shaped, circular, rectangular, hemi-spherical, or combinations thereof.

In an embodiment, the connector portion includes two coaxial, spherical portions on opposing sides of the valve arm.

In an embodiment, the connecting element of the cassette includes a bar that resides in and connects two opposing sides of a hole in the cassette. The bar has a shape selected from the group consisting of substantially cylindrical, rectangular, or combinations thereof.

In an embodiment, the connecting element of the cassette includes first and second pegs located on opposite sides of a hole in the cassette.

In an embodiment, the connector portion of the valve arm is configured to rotate about the connecting element of the cassette.

In an embodiment, the valve arm includes a projection on a top side of the valve arm. The projection is configured to interact with a tab member of a pumping device when the cassette is inserted into the pumping device. The tab member cooperates with the projection of the valve arm to overcome a blocked position bias of the valve arm and move the valve arm to a free-flow position.

It is an advantage of the present disclosure to provide improved cassettes.

It is also an advantage of the present disclosure to provide improved fluid delivery systems.

Yet another advantage of the present disclosure is to provide methods of using improved cassettes.

Still yet another advantage of the present disclosure is to provide cassettes that are able to detect air in a tubing line.

Another advantage of the present disclosure is to provide cassettes that are able to detect occlusions in a tubing line.

An advantage of the present disclosure is to provide cassettes that prevent kinking or crimping of a tubing line.

Yet another advantage of the present disclosure is to provide an improved flow control device.

Still yet another advantage of the present disclosure is to provide an improved locking mechanism for a fluid delivery system.

Another advantage of the present disclosure is to provide an improved guide system for insertion of a cassette into a fluid delivery pump.

Additional features and advantages are described herein, and will be apparent from the following Detailed Description and the figures.

BRIEF DESCRIPTION OF THE FIGURES

FIGS. 23-24 show perspective views of a clamping element of a pinch clamp assembly according to an embodiment of the present disclosure.

FIGS. 25-28 show a front view, left side view, plan view, and right side view, respectively of a clamping element of a pinch clamp assembly according to an embodiment of the present disclosure.

FIG. 80 shows a perspective view of a cassette having an anti-free flow mechanism according to an embodiment of the present disclosure.

DETAILED DESCRIPTION

Figure 1:
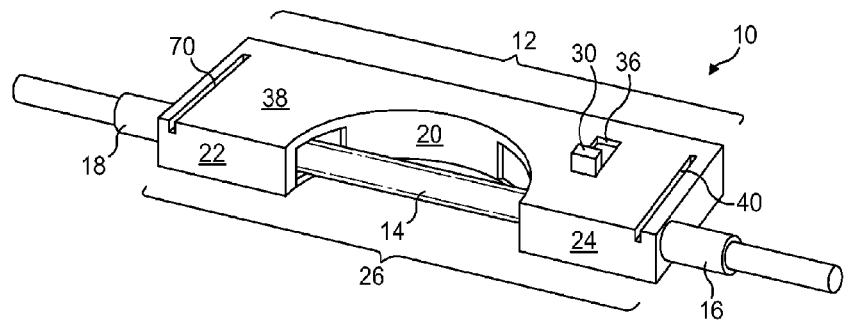
FIG. 1 is a perspective view of a first face, and first and second outside walls of a cassette according to an embodiment of the present disclosure.

The present disclosure generally relates to a fluid delivery system including an infusion pump and a cassette that can be associated with the infusion pump for delivery of a fluid to a subject.

In an embodiment, the cassette includes a housing having first and second ends for holding flexible tubing through which fluid may be directed. The tubing is configured for engaging a pumping mechanism of an infusion pump that provides movement of the fluid through the tubing. The housing has a section with a rigid curved wall adjacent to where the length of tubing engages a pumping mechanism when associated with the infusion pump to provide movement of fluid through the tubing. The cassette may include an anti-flow valve mechanism to prevent free-flow through the tubing when not engaged with the pump.

In an embodiment the cassette is made of a non-reflective material. In an embodiment, the cassette has a dark pigment added to it. In an embodiment, the cassette has a dark pigment added to it to prevent ambient light from traveling along the cassette. In an embodiment, the cassette has carbon black pigment added to it. In an embodiment, the cassette has carbon black pigment added to it to prevent ambient light from traveling along the cassette.

In embodiments wherein the cassette includes an anti-flow valve mechanism, the interaction between the anti-flow valve and the pumping mechanism is important to ensure the safety of a patient. For example, when the cassette is not engaged with a pumping mechanism, the anti-flow valve mechanism ensures that fluid cannot flow through the tube. Alternatively, when the cassette is fully inserted into a pumping device, a pumping mechanism deforms the tubing so as to prevent fluid from flowing through the tube. Generally, it is important to ensure that an anti-flow configuration is maintained at all times prior to and after fluid delivery to a patient.

During the insertion of the cassette into a pumping device and removal of the cassette from a pumping device, an anti-flow valve mechanism should be configured to ensure that flow through the tubing is prohibited. For example, when the cassette is being inserted into a pumping device, it is important that the pumping mechanism engages and blocks flow through the tubing before the anti-flow valve mechanism releases. Therefore, prior to insertion into a pumping device, an anti-flow valve mechanism will be closed to block fluid flow through the tubing. As the cassette is fully inserted into the pumping device, both an anti-flow valve mechanism and a pumping mechanism may simultaneously block flow through the tubing. Once the cassette is fully inserted into the pumping device, the anti-flow valve mechanism disengages and a pumping mechanism may block free flow through the tubing.

Similarly, during removal of the cassette from a pumping device, it is important that the anti-flow valve mechanism engages the tubing to block flow through the tubing before the pumping mechanism disengages from the tubing. For example, when the cassette is being removed from a pumping device, it is important that the anti-flow valve mechanism engages and blocks flow through the tubing before the pumping mechanism releases. Therefore, prior to removal from a pumping device, an anti-flow valve mechanism will be open to allow fluid flow through the tubing. As the cassette is removed, the anti-flow valve mechanism may then be activated such that both an anti-flow valve mechanism and a pumping mechanism may simultaneously block flow through the tubing. Once the cassette is removed from a pumping device and the pumping mechanism loses contact with tubing, the anti-flow valve mechanism will still be activated to prevent flow through the tubing. These general principles may apply to each of the embodiments discussed in the present disclosure that include the use of an anti-flow valve mechanism.

The cassette can be associated with a dedicated infusion pump that controls the free flow of fluid from a reservoir to a patient, and the cassette/pump fluid delivery system provides controlled delivery of such fluids. The cassette becomes operative through association with the infusion pump, without the interaction of additional independent mechanisms, and restricts fluid flow either prior to or immediately upon removal from the pump. The infusion pump engages the cassette mechanisms to allow a controlled flow of fluid to a patient.

In an embodiment the present disclosure is directed to a cassette that is connected between a fluid reservoir such as an IV bag and the intravenous line to the patient. The embodiment has a housing with an essentially rectangular shape and a width configured and dimensioned to fit within an opening in an infusion pump, where the housing has four outside walls, and two faces.

The first and third outside walls, situated opposite each other, define the first and second ends for holding the tubing through which the fluid is directed. The outside walls forming the first and second ends each have a flat wall with an opening configured and dimensioned to fit either an inlet or outlet tubing support which passes through the opening. In another embodiment, the tubing supports are formed as a single integral part of the housing. The tubing supports thereby being molded features of the housing rather than separate components requiring assembly into the cassette housing.

The flexible tubing is fitted over male junctions of the tubing supports and held between the ends of the cassette in a straight line. The position of the tubing crosses a section of the housing that can be either exposed or covered.

A second outside wall between and perpendicular to the first and third outside walls has two straight wall sections and a rigid curved wall section located between the two straight wall sections, defining a section with a rigid curved wall adjacent to where the length of tubing engages a pumping mechanism when associated with the infusion pump to provide movement of fluid through the tubing. The rigid curved wall is configured and dimensioned to allow the pumping mechanism of the infusion pump to freely rotate, and has an opening on either side through which the flexible tubing can pass. When associated with the pump, the length of tubing is positioned in contact with and between the curved wall and the pumping mechanism. The curved wall must be suitably strong and rigid to sustain the repeated action of the pumping mechanism.

The housing has a first face in a perpendicular relationship with the outside walls. The first face can be rectangularly configured and dimension to match the outside dimensions of the four walls of the housing, or have a cut-away portion that is configured and dimensioned to coincide with the curved wall section of the third outside wall. The first face has registration groves configured and dimensioned to receive a matching raised portion of the infusion pump, and an opening through which a tab member can protrude.

The housing has a second face in a perpendicular relationship with the outside walls on the side opposite the first face, that can be rectangularly configured and dimension to match the outside dimensions of the four walls of the housing, or have a cut-away portion that is configured and dimensioned to coincide with the curved wall section of the third outside wall. The first and second faces with cut-away portions thereby forming an open area that exposes the tubing, whereas the rectangular faces cover and protect the tubing. The second face has at least one opening, but preferably two openings placed at opposite ends of the housing. The openings are aligned with the position of the tubing and act as windows to allow observation of the fluid and the presence of any bubbles or foreign material. This is particularly important when the tubing in the curved section is covered by both faces thereby preventing viewing of that segment of tubing.

In an embodiment, the cassette has an anti-flow valve mechanism associated with the housing, which includes a moveable member and a force-applying member. The moveable member includes a pinch head and a tab member that extends perpendicular to the orientation of the moveable member and a force-applying member through the opening in the first face of the housing. The force-applying member biases the moveable member against the tubing to prevent fluid flow when the cassette is not associated with the infusion pump. The force-applying member used to bias the moveable member can be a compression spring, a leaf spring, or an elastic component. The moveable member has a larger surface on the side contacting the force-applying member, and a narrower surface on the side contacting the tubing. The narrower surface acts to concentrate the force of the force-applying member, and improves the closing action of the moveable member on the tubing. The overall configuration of the moveable member and pinch head can have several shapes, the most preferred being either "T-shaped" or "wedge-shaped." The moveable member can also have a seating opposite the end pressing against the tubing, which holds the force-applying member in position.

The tab member is operatively associated with the housing and anti-flow valve mechanism, and is movable between the fluid non-delivery position and a fluid delivery position. When the cassette is associated with the pump, the tab is pushed back, thereby retracting the associated moveable member from contact with the flexible tubing, and increasing the stored force in the force-applying member. When the cassette is disassociated from the infusion pump, the stored force in the force-applying member is released and returns the moveable member and associated tab member to the biased fluid non-delivery position.

The tab member can also be designed to be fixed in the open fluid delivery position for an extended period of time when the cassette is not associated with the infusion pump to prevent the tubing from becoming permanently compressed or deformed. Such depression, crimping or deformation can effect the flow of fluids through the tubing resulting in an incorrect amount flowing even when the cassette and infusion pump are both otherwise working properly. The tab member can be held in the open position through the use of a plug that is fitted into the opening between the tab member and the edges of the housing face. The plug can then be pulled out to activate the cassette and return the anti-flow valve mechanism to the biased fluid non-delivery position. Latches, catches and hooks associated with the cassette can also be used to hold the tab in the open fluid delivery position for storage and then removed when the cassette is to be used.

In another embodiment, the present disclosure is directed to a reusable cassette that is slipped over the tubing between the fluid reservoir and the patient. The embodiment has a housing with an essentially rectangular shape and a width configured and dimensioned to fit within an opening in an infusion pump, where the housing has four outside walls, and two faces.

Two of the outside walls define a first and second ends for holding the tubing through which the fluid is directed. The outside walls forming the first and second ends each have a flat wall with an opening configured and dimensioned to fit either the inlet or outlet tubing support which passes through the opening.

The inlet and outlet tubing supports are bushings having openings suitably dimensioned and configured to allow the flexible tubing to be pushed through the bushings, but remain held snugly in position. The bushings prevent the cassette from sliding down the tubing when the cassette is not associated with an infusion pump, and prevents the tubing from slipping when the cassette is associated with a pump.

The infusion pump is configured and dimensioned to be associated with a related cassette. The pump has either an opening into which the cassette can be inserted, or a depression or recess into which the cassette can be seated.

Another embodiment of the present disclosure relates to a cassette for engagement with an infusion pump for delivery of a fluid to a subject. The cassette includes a housing having first and second ends for holding flexible tubing through which the fluid is directed, wherein the tubing is configured for engaging a pumping mechanism of an infusion pump that provides movement of fluid through the tubing; and an anti-flow valve mechanism associated with the tubing, housing or the cassette and present either in or near the housing or cassette. The anti-flow valve mechanism is biased against the tubing in a fluid non-delivery position to prevent flow therethrough and includes a member operatively associated with the cassette and anti-flow valve mechanism to overcome the force-applying member bias to allow flow of fluid through the tubing when the housing is engaged with the pump. The anti-flow valve mechanism is associated with the tubing, cassette or housing or is situated in or near the cassette or housing. The anti-flow valve mechanism preferably may have a moveable member and a force-applying member, wherein the force-applying member in a fluid non-delivery position biases the moveable member against the tubing to prevent flow therethough. The cassette also includes a tab member operatively associated with the cassette housing and anti-flow valve mechanism and movable between the fluid non-delivery position and a fluid delivery position where the force-applying member bias is removed so as to allow flow of fluid through the tubing. The tab member is operatively associated with the cassette and anti-flow valve mechanism so as to overcome the force-applying member bias. The housing is configured and dimensioned for engagement with a dedicated infusion pump, wherein during or after engagement the tab member is moved to the fluid delivery position by the pump to allow flow of the fluid through the tubing, while before or as the cassette is removed from the pump, the tab member is released so that the force-applying member returns to the fluid non-delivery position to prevent flow of fluid through the tubing.

The tab member can move the moveable member to the fluid delivery position as the cassette engages the infusion pump to allow flow of fluid through the tubing and as the cassette is removed from the pump the tab member is released so that the moveable member returns to the fluid non-delivery position to prevent flow of fluid through the tubing such that movement of the tab member between the fluid non-delivery position and the fluid delivery position changes the biasing of the force-applying member. Alternatively, the tab member can move the moveable member to the fluid delivery position after the cassette engages the infusion pump to allow flow of fluid through the tubing, and before the cassette is removed from the pump the tab member is released.

The housing of the cassette may have an essentially rectangular shape and is configured and dimensioned to fit within an opening in the infusion pump, and the length of tubing is initially held between the ends of the cassette in a straight line and in front of a rigid curved wall of the housing such that when engaged with the pumping mechanism of the pump, the length of tubing is accurately positioned in contact with and between the curved wall and the pumping mechanism.

The force-applying member of the anti-flow valve mechanism includes a compression spring and the moveable member of the anti-flow valve mechanism includes a pinch head that has a relatively larger cross-sectional surface that contacts the force-applying member and a relatively narrower cross-sectional surface contacting the tubing that concentrates the force of the force-applying member against the tubing. Also, the housing may include registration grooves for alignment of the cassette during engagement with the infusion pump.

The housing of the cassette generally includes at least one window adjacent the tubing to allow monitoring or detection of fluid flow therethrough. In an embodiment, the housing is made of molded plastic, the tubing is made of an elastomeric or silicone material, and the tubing is held between inlet and outlet tubing supports in the housing. Each tubing support can include a male junction and a female junction, wherein in the inlet support the male junction is configured and dimensioned to fit inside the tubing and the female junction is configured and dimensioned to receive tubing extending to a fluid supply, and in the outlet support, the male junction is configured and dimensioned to fit inside the tubing and the female junction is configured and dimensioned to receive the length of tubing that extends to the subject.

Another embodiment of the present disclosure relates to a fluid delivery system including one of the cassettes described herein and an infusion pump, wherein the pump includes a pump housing having an opening configured and dimensioned to receive or engage with the cassette; and an activation mechanism for engaging the member and thereby causing the member to move between the fluid non-delivery position and the fluid delivery position to allow fluid flow through the tubing, and wherein the pumping mechanism that engages the flexible tubing to provide movement of fluid through the tubing only when the cassette is engaged with the pump, the pump detects the cassette is engaged, and the tab member is in the fluid delivery position.

The pump can have a detector for determining whether the cassette is properly engaged with the pump and pump mechanism. The pumping mechanism typically stretches the flexible tubing by an amount necessary to tension the tubing by a sufficient amount to allow the correct fluid flow through the tubing each time the pumping mechanism and cassette are engaged. Also, the activation mechanism causes the tab member to move between the fluid non-delivery position and a fluid delivery position either as the cassette engages the pump or after the cassette engages the pump. Thus, the pumping mechanism is in a fixed position and the flexible tubing becomes engaged therewith by moving the cassette into contact with the pumping mechanism, or the cassette is in a fixed position when associated with the infusion pump and the pumping mechanism engages the flexible tubing by moving into contact therewith. In an embodiment, the infusion pump further includes at least one registration component that engages the registration grooves of the cassette, and at least one sensor in optical alignment with the window of the cassette for monitoring or detection of fluid flow through the tubing.

Yet another embodiment of the present disclosure relates to a method of preventing free flow of fluid through the tubing of an infusion set which includes providing the tubing in a cassette that engages an infusion pump for delivery of a fluid to a subject, and providing the tubing or cassette with an anti-flow valve mechanism having a moveable member and force-applying member wherein, when not engaged with the pump, the moveable member and force-applying member are maintained in a fluid non-delivery position with the force-applying member biasing the moveable member against the tubing to prevent flow therethrough, and further wherein when or after the cassette engages the pump, the force-applying member is moved by the pump to a flow delivery position where the moveable member is not biased against the tubing to allow fluid to flow therethrough.

Also, the present disclosure relates to the use of one of the anti-flow valve mechanisms or fluid delivery systems described herein to prevent free-flow of fluid through the tubing of an infusion set. The anti-flow valve mechanism is provided on or in association with the tubing or a cassette having a housing and can be used for preventing free-flow of fluid through the tubing of an infusion set.

Another embodiment of the present disclosure relates to a fluid delivery system having an infusion pump and a cassette with tubing that is configured for engaging the pump mechanism of the infusion pump to accurately and repeatably deliver a fluid to a subject.

The cassette may include a housing having first and second ends for holding flexible tubing through which the fluid is directed, wherein the tubing is configured for engaging a pumping mechanism of an infusion pump that provides movement of the fluid through the tubing. The length of tubing is initially held between first and second ends of the cassette prior to engaging the pumping mechanism and in a straight line. The position of the first and second ends of the housing and which at least partially defines a flow path along which the tubing is tensioned for fluid flow therein, and the length of tubing is accurately and repeatably positioned in the flow path with the pumping mechanism stretching the flexible tubing to repeatably tension the tubing to allow correct fluid flow therethrough. The flow path is advantageously and at least partially defined in front of a rigid curved wall of the housing, wherein the fixed, rigid curved wall forms a concave shape opposite the pumping mechanism. When engaged with the pumping mechanism of the pump, this length of tubing is in contact with and positioned between the curved wall and the pumping mechanism upon each engagement of the pumping mechanism and tubing. Upon each engagement of the pumping mechanism and tubing, the pumping mechanism accurately and repeatably stretches the flexible tubing and urges it into contact with the curved wall to tension the tubing to allow correct fluid flow therethrough.

The tubing may be moved into position either when the engagement of the cassette with the pump causes the tubing to move between its initial position and a fluid delivery position, where the tubing is in contact with the curved wall, or alternatively, after engagement of the cassette with the pump, the pumping mechanism moves to urge the tubing to a fluid delivery position in contact with the curved wall.

Either the pumping mechanism or the cassette can be the moveable component, while the other remains in a fixed position. If the pumping mechanism is in a fixed position, the flexible tubing becomes engaged by moving the cassette into contact with the pumping mechanism, whereas if the cassette is in a fixed position when engaged with the infusion pump, the pumping mechanism engages the flexible tubing by moving into contact therewith.

The cassette may include an anti-flow valve mechanism that is initially biased against the tubing in a fluid non-delivery position to prevent flow therethrough, and a member operatively associated with the cassette and anti-flow valve mechanism to overcome the force-applying member bias to allow flow of fluid through the tubing when the housing is engaged with the pump. The housing is configured and dimensioned for engagement with the infusion pump, wherein during or after engagement the member assumes a fluid delivery position to allow flow of the fluid through the tubing, while before or as the cassette is removed from the pump, the member assumes the fluid non-delivery position to prevent flow of fluid through the tubing.

The anti-flow valve mechanism may be associated with the tubing, cassette or housing or is situated in or near the cassette or housing and has a moveable member and a force-applying member, wherein the force applying member in the fluid non-delivery position biases the moveable member against the tubing to prevent flow therethrough; and wherein the moveable member is moveable between the fluid non-delivery position and the fluid delivery position where the force-applying member bias is removed so as to allow fluid flow through the tubing.

The cassette housing is generally configured and dimensioned for engagement with the infusion pump, where the housing has an essentially rectangular shape and is configured and dimensioned to fit within an opening in the infusion pump, or a shape and size configured and dimensioned to be capable of being attached or adjoined to the exterior of the infusion pump, and the housing includes registration grooves for alignment of the cassette during engagement with the infusion pump. Additionally, the housing includes at least one window adjacent the tubing to allow monitoring or detection of fluid flow therethrough. The housing is made of molded plastic, and the tubing is made of an elastomeric or silicone material.

The tubing may be held between inlet and outlet tubing supports in the housing, wherein each tubing support includes a male junction and a female junction, wherein in the inlet support the male junction is configured and dimensioned to fit inside the tubing and the female junction is configured and dimensioned to receive tubing extending to a fluid supply, and in the outlet support, the male junction is configured and dimensioned to fit inside tubing and the female junction is configured and dimensioned to receive the length of tubing that extends to the subject.

Another embodiment of the present disclosure relates to a fluid delivery system including a cassette as described above and an infusion pump. The infusion pump includes a housing having an opening configured and dimensioned to receive the cassette, and a pumping mechanism that engages the flexible tubing and stretches it to position the stretched tubing along the curved wall to provide sufficient tension to allow accurate and repeatable amounts of fluid to flow through the tubing. The combination of the infusion pump and cassette represents yet another embodiment of the present disclosure.

The infusion pump is suitably designed and configured to be associated with the companion cassette having in a first embodiment an opening into which a cassette with suitable dimensions could be inserted, and having in a second embodiment features for attaching and securing the cassette to an exterior surface of the infusion pump. The opening in the pump could be either a slot into which the cassette could be slid edge-wise, or a depression or recess in a face of the pump into which the cassette could be seated. The feature for attaching a cassette to an exterior surface of the infusion pump includes tabs, clips, latches, catches, fasteners, or any combination thereof. The cassette can become engaged with the infusion pump either by insertion into the opening, depression or recess in the pump, or by attaching or adjoining to the infusion pump exterior using the features mentioned above.

The infusion pump typically includes a pumping mechanism that engages the flexible tubing, and stretches the tubing to conform to the flow path by an amount necessary to tension the tubing by a sufficient amount to allow the correct fluid flow through the tubing when the pumping mechanism is engaged. The pumping mechanism stretches the flexible tubing to the same extent each time the cassette becomes associated with the infusion pump.

The infusion pump may also have at least one registration component that engages the registration grooves of the cassette, and at least one sensor in optical alignment with the window of the cassette for monitoring or detection of fluid flow through the tubing.

Another embodiment of the present disclosure relates to a method of accurately and repeatedly dispensing fluid through the tubing of an infusion set which includes providing the tubing in a cassette that engages an infusion pump for delivery of a fluid to a subject, and providing the cassette with a housing having first and second ends for holding flexible tubing through which the fluid is directed, and with a flow path at least partially defined by a rigid curved wall, with the housing having a length of the tubing which length of tubing engages a pumping mechanism of the infusion pump when associated therewith to be stretched and positioned between the pumping mechanism and the curved wall to provide movement of fluid through the tubing.

In this method, the cassette is used for accurately delivering fluid to a subject via an infusion pump, characterized in that the cassette includes a curved wall such that upon engagement with the pumping mechanism of the infusion pump, the tubing is stretched to be positioned at least partially along the flow path between the pumping mechanism and the curved wall to accurately and repeatably deliver fluid to the subject. The cassette is used to accurately and repeatably deliver a fluid to a subject via an infusion pump.

Yet another embodiment of the present disclosure relates to the use of one of the cassettes, fluid delivery systems and/or pumps disclosed herein for accurately delivering fluid to a subject via tubing of an infusion set. As explained herein, the cassette includes a structure that at least partially defines a flow path, e.g., a curved wall, such that upon engagement with the pumping mechanism of the infusion pump, the tubing is stretched to be positioned along the flow path between the pumping mechanism and the curved wall to accurately and repeatably deliver fluid to the subject.

Referring to FIG. 1, the various components of a cassette 10 according to the present disclosure can be seen. The cassette 10 includes a housing 12, flexible tubing 14 and tubing supports 16 and 18. The flexible tube 14 spans the section formed by the rigid curved wall 20 between the first straight wall section 22 and the second straight wall section 24 of the second outside wall 26. The flexible tubing passes through the openings 28 on either side of the curved wall 20 to meet the inlet tubing support 16 and outlet tubing support 18. The tab member 30 extends from the moveable member 32 of the anti-flow valve mechanism 34 through the opening 36 in the first face 38 sufficiently to engage an activation mechanism associated with the infusion pump. The registration grooves 40 are positioned in the first face 38 to accept raised features of the infusion pump that are configured and dimensioned to fit into the registration grooves in the cassette. The registration grooves can have a variety of lengths, cross-sectional sizes and shapes including but not limited to triangular, square, rectangular, "T," and circular.

Figure 2:
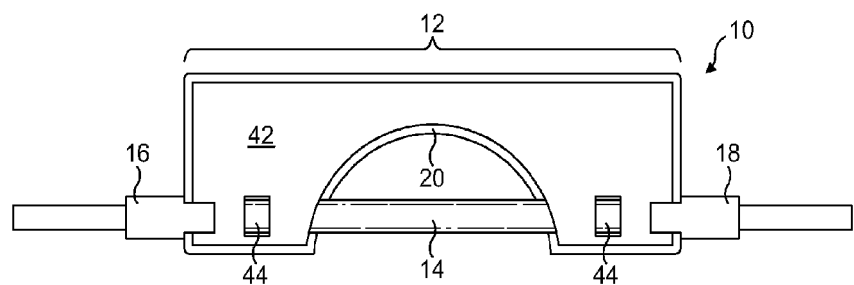
FIG. 2 is a view of a second face of a cassette showing windows for observing fluid flow according to an embodiment of the present disclosure.

Referring to FIG. 2, the flexible tubing 14 is situated between the inlet tubing support 16 and outlet tubing support 18. Fluid flow through the flexible tube can be observed through the openings 44 in the second face 42 of the housing 12, when the flexible tubing 14 is pressed against the rigid curved wall 20 by the pump mechanism. This also allows the use of bubble detection or other monitoring devices to assure that the fluid is properly flowing through the tubing 14.

Figure 3:
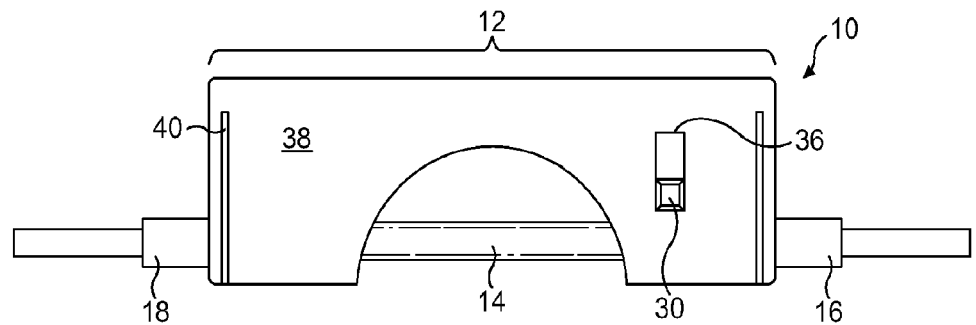
FIG. 3 is a view of a first face of a cassette in an embodiment of the present disclosure showing a tab member attached to an anti-flow valve mechanism in a default biased non-delivery position when not inserted in an infusion pump according to an embodiment of the present disclosure.
Figure 4:
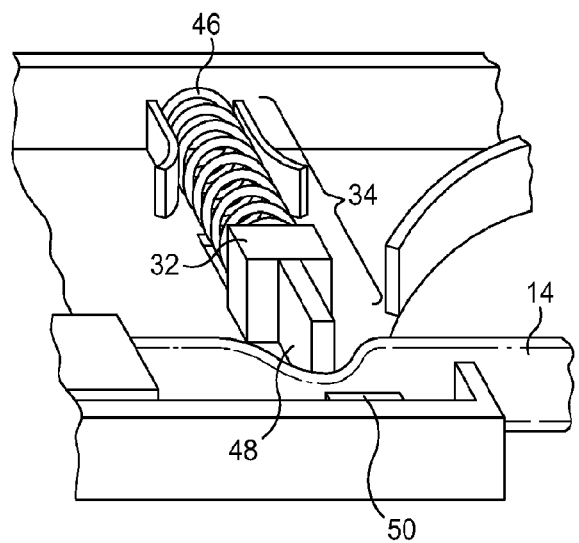
FIG. 4 is an enlarged internal perspective view showing the details of an anti-flow valve mechanism when in the non-delivery position according to an embodiment of the present disclosure.

Referring to FIG. 3, the tab member 30 extending through the opening 36 in the first face 38 of the housing 12 is in the default fluid non-delivery position, where, as shown in FIG. 4, the force-applying member 46 presses against the moveable member 32 causing the pinch head 48 to compress the flexible tubing 14 against the reinforcement 50, thereby preventing fluid flow.

Figure 5:
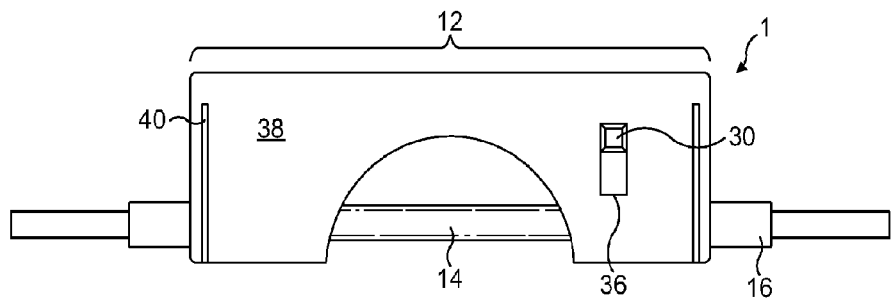
FIG. 5 is a view of a first face of the cassette showing a tab member attached to an anti-flow valve mechanism in an unbiased delivery position when inserted in an infusion pump according to an embodiment of the present disclosure.
Figure 6:
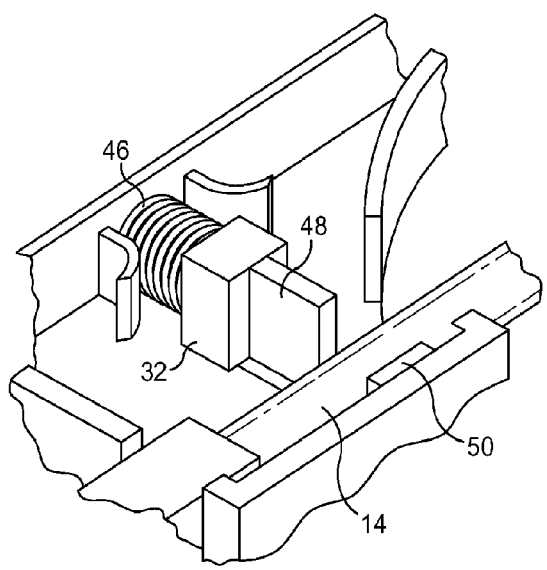
FIG. 6 is an enlarged internal perspective view showing a detail of an anti-flow valve mechanism in a delivery position according to an embodiment of the present disclosure.

Referring to FIG. 5, the tab member 30 extending through the opening 36 in the first face 38 of the housing 12 can be moved to the activated fluid delivery position, where, as shown in FIG. 6, the force-applying member 46 has a reduced dimension and a concomitant increase in stored force by the retraction of the moveable member 32 away from the flexible tubing 14, which releases the force of the pinch head 48 against the flexible tubing and thereby allows free fluid flow. This movement is achieved either automatically when or as the cassette is inserted into a companion infusion pump designed to receive it or by a mechanism in the pump housing itself to move the tab and open the valve only when the pump is activated. The pump includes conventional roller or finger members that, when activated for operation, compress the tube to urge the fluid to flow therethrough. As noted, by the time the pump is activated, the anti-flow valve mechanism is moved to a position where the tubing is not occluded to allow the fluid to flow. When the cassette is disassociated from the pump, or when the pump is deactivated, the anti-flow valve mechanism returns to the non-fluid delivery position to prevent any flow through the tubing, thus avoiding any unintended free-flow conditions.

Figure 7:
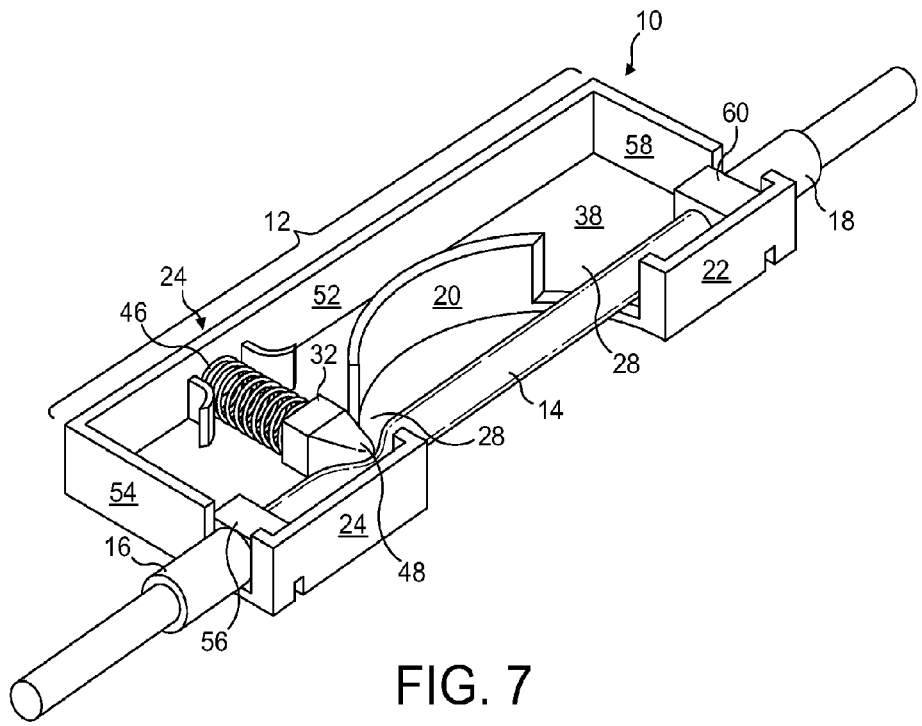
FIG. 7 is a perspective view of an interior assembly of a cassette according to an embodiment of the present disclosure.

Referring to FIG. 7, the internal arrangement of the anti-flow valve mechanism 34, flexible tubing 14, inlet tubing support 16 and outlet tubing support 18 within the housing 12 can be clearly seen with reference to the rigid curved wall section 20 with openings 28 on either side located between the first straight wall section 22 and the second straight wall section 24 of the second outside wall 26. The force-applying member 46 is positioned between the fourth straight wall section 52 and the moveable member 32, thereby pressing the pinch head 48 against the flexible tubing 14, so the tubing is pressed closed against a reinforcement 50 adjacent to the first straight wall section 22 of the second outside wall 26.

The anti-flow valve mechanism may be located on the inlet side of the cassette as depicted in the FIGS. However, the skilled artisan will also appreciate that it could also be located on the outlet side.

The housing 12 may be rectangular with dimensions and a width suitable to fit into an infusion pump, although the housing could also have other shapes if necessary to fit within the pump. The housing 12 is made of a material suitable for use in a medical environment without breaking or causing contamination, and can be either disposable or capable of being cleaned, autoclaved or sanitized for subsequent reuse. Generally, an engineering plastic is used for this purpose. The housing 12 allows easy and secure placement of the force-applying member, moveable member and tubing supports inside the closed housing. The housing 12 may be formed of two or more molded pieces that are later assembled and sealed with the other components inside. The housing 12 may be permanently sealed, or be held together by tabs, clips, latches, catches, fasteners, or any combination thereof to allow for later access to the internal components for cleaning or replacement.

The fourth outside wall 52 may be a solid flat face that can be easily pushed against when inserting the cassette 10 into or securing it to the exterior of an infusion pump, although the skilled artisan will appreciate that it could have other contours, textures, openings, or features.

The second outside wall 26 has both straight and curved sections configured and dimensioned to engage the infusion pump and pumping mechanism. The rigid curved wall 20 is configured and dimensioned to accept the infusion pump wheel and rollers, so there is free rotation of these elements when the pump is in operation, and the rollers can compress the flexible tubing 14 properly to create the pumping action. The cassette is designed so that the curved wall is sufficiently strong and rigid to retain its shape as the rollers or fingers of the infusion pump repeatedly press against the flexible tubing compressing it against the wall. The edges of the curved wall at the openings 28 may be beveled to avoid corners that can pinch the flexible tubing when the cassette 10 is inserted into the infusion pump and the infusion pump wheel and rollers push the flexible tubing back against the curved impression.

The openings 28 on either side of the rigid curved wall section are suitably sized, configured and dimensioned to allow the flexible tubing 14 to follow the contour of the curved impression without completely pinching off flow by pressing against either edge of the curve when the cassette is inserted into the infusion pump, and are aligned with the flexible tube when it is fixed in the straight-through position between the two tube supports, when the housing is not inserted in the infusion pump.

The fixed position and length of the flexible tubing in coordination with the configuration and dimensions of the cassette and pump produces the same amount of tension in the flexible tubing each and every time the cassette is engaged by the pumping mechanism. Engagement of the pumping mechanism with the cassette then creates suitable tension in the flexible tubing to allow a correct and accurate amount of fluid flow when the pump is operating.

In an embodiment, the first outside wall 54 has an opening 56 configured and dimensioned to hold an inlet tubing support 16 which passes through the opening, and the third outside wall 58 has an opening 60 configured and dimensioned to hold an outlet tubing support 18 which passes through the opening.

In another embodiment, the tubing supports are molded as part of the first and third outside walls to form a single integral part of the housing wall.

In either embodiment, the tubing supports 16 and 18 can have the form of either adaptors that connect a separate length of flexible tubing, which is fixed between the adaptors, with different tubing on the inlet and outlet sides, or bushings that have an inner diameter that is suitably dimensioned to be pushed over a unitary piece of flexible tubing and hold it snugly between the two bushings to prevent the cassette from sliding down the tubing when the cassette is not associated with the infusion pump.

The tubing supports can be made of a transparent material that allows the fluid flow to be observed, and any bubbles or obstructions to be detected or monitored. Alternatively, as described herein below, windows may be provided in the housing for this purpose.

When not a molded part of the housing, the adaptor used to connect different pieces of tubing may have a cube-shaped central section that is sized, configured and dimensioned to be held in place within the housing at the first outside wall opening 56 or third outside wall opening 60, with one round male junction extending from the central section into the housing having an outer diameter over which the flexible tubing can be pushed to form an airtight seal, and one round female junction extending from the central section out of the housing 12 with an inner diameter into which an intravenous line can be pushed to form an airtight seal. The male junction can have barbs to better secure the flexible tubing. The skilled artisan will appreciate that other designs may also be used for holding the tubing in the manner and position described herein.

When not a molded part of the housing, the bushing used to hold a length of flexible tubing preferably has a cube-shaped central section that is sized, configured and dimensioned to be held in place within the housing at the first outside wall opening 56 or third outside wall opening 60, with an interior stress-relief portion that extends from the central section into the housing, and an exterior stress-relief portion that extends from the central portion out from the housing. A hole having a diameter dimensioned to fit tightly over the flexible tubing passing through the bushing. The bushings hold the flexible tubing 14 snugly so the cassette does not slide down the tubing if allowed to hang from it, and prevents a change in tension in the flexible tubing due to the action of the infusion pump pulling on the tubing when the cassette is inserted in the infusion pump.

The flexible tubing 14 can be made of any elastomeric material. The elastomeric material may be a transparent flexible medical grade material such as, for example, silicone.

The anti-flow valve mechanism 34 has a moveable member 32 that is operatively associated with a force-applying member 46 at a face opposite a pinch head 48. The moveable member face in contact with the force-applying member is suitably dimensioned to allow sufficient contact between the force-applying member and the moveable member to transfer the force of the force-applying member to the pinch head. The face of the moveable member preferably has a raised or recessed feature that can seat the force-applying member to thereby keep the force-applying member aligned and prevent the loss of contact between the two components.

The moveable member 32 preferably has wider dimensions at the force-applying member contact end and narrower dimensions at the pinch head 48 end, and a tab member 30 extending from a face of the moveable member 32 perpendicular to the axis of the force-applying member 46 and pinch head 48. The pinch head can have different shapes such as a "T," "U," "V," or a wedge. Such shapes concentrate the force of the force-applying member to a smaller area to improve the closing action on the flexible tubing when in the default non-delivery position. The shape of the end of the pinch head in contact with the tubing can have either a flat face, curved face with a range of radii, or a sharp corner, where the curved face is the preferred embodiment. Such curved end faces reduce the wear on the portion of tubing that becomes crimped when the moveable member is in the non-delivery position.

The pinch head 48 presses against one side of the flexible tubing 14 and compresses it against a reinforcement 50 on the opposite side thereby closing the tubing and preventing any free fluid flow when the cassette is not inserted in an infusion pump.

The tab member 30 extends from the moveable member 32 perpendicular to the pinch head through an opening 36 in the first face 38 of the housing 12. The tab member 30 is sufficiently long to extend above the first face 38 of the housing 12, and engage an activation mechanism on the infusion pump, which would cause the moveable member 32 to retract and increase the stored force in the force-applying member 46 when the cassette 10 is associated with the infusion pump. The moveable member 32 is made of a tough impact resistant material sufficient to withstand repeated engagement of the tab with the infusion pump activation mechanism while resisting the force of the force-applying member when the cassette is associated with the infusion pump, as well as contact between the pinch head and the flexible tubing when the cassette is disassociated from the pump.

The force-applying member 46 is positioned between the fourth outside wall 52 and the moveable member 32, which thereby translates the force through the pinch head 48 to compress the flexible tubing 14. The force-applying member has an increase in stored force when the cassette 10 is associated with an infusion pump, and the contact between an activation mechanism and the tab member 30 causes the anti-flow valve mechanism 34 to retract. The force-applying member may be a round compression spring made of stainless steel or another material suitable for use in a medical environment, however it may also be a leaf spring, lever or elastic element. The force-applying member has sufficient strength to completely pinch the flexible tubing closed when the tab is released, but can be compressed when the cassette is associated with the infusion pump. The force is applied to the tubing through the pinch head, which can have different shapes such as a "T," "U," "V," or a wedge. These shapes result in a smaller contact surface between the pinch head and the flexible tubing, and thereby concentrates the force exerted by the force-applying member.

Figure 8:
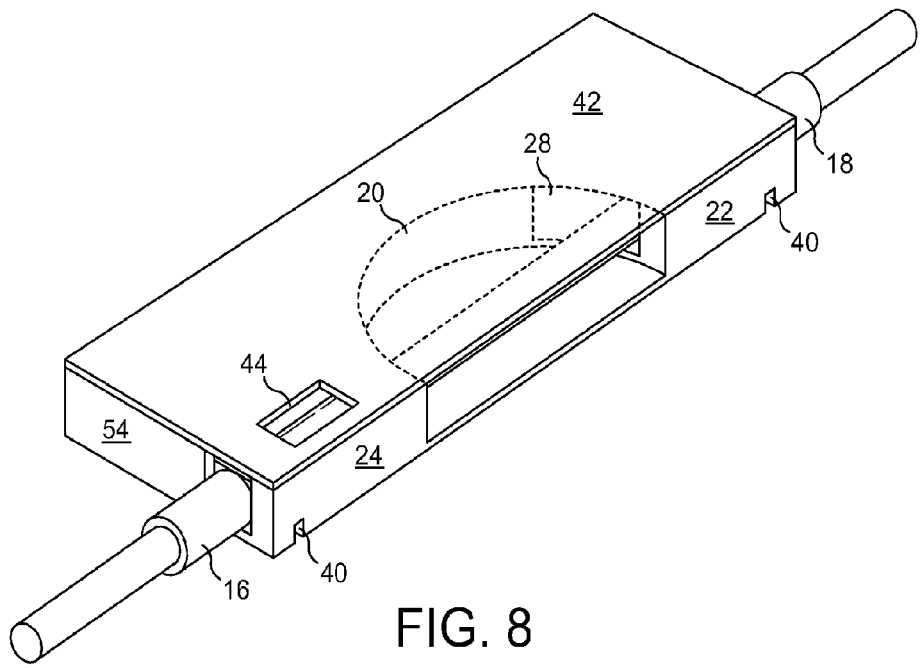
FIG. 8 is a perspective view of a cassette illustrating another embodiment of a housing without portions of a first and second face cut away to create an open area according to an embodiment of the present disclosure.

Referring to FIG. 8, the first face 38 of the housing 12 is rectangular in shape to match the dimensions of the outside walls of the housing, but could have a curved cut-away portion that is configured and dimensioned to match the straight wall sections 22, 24 and curved wall section 20 of the second outside wall 26 to form an open area in conjunction with the cut-away portion of the second face thereby exposing the tubing 14 (see, FIG. 1). The first face 38 has an opening 36 suitably positioned to allow the tab member 30 of the piston 32 to extend through the opening and above the first face. The first face 38 has two registration grooves 40 configured and dimensioned to receive a raised feature on the infusion pump. The grooves 40 polarize the cassette 10 so it can only be inserted one way into the infusion pump. In an embodiment, the shape of the grooves is a straight line.

The second face 42 of the housing 12 may be rectangular in shape to match the dimensions of the outside walls of the housing (see, FIG. 8), but may have a curved cut-away portion that is configured and dimensioned to match the straight wall sections 22, 24 and curved wall section 20 of the second outside wall 26 to form an open area in conjunction with the cut-away portion of the second face thereby exposing the tubing 14 (see, FIG. 1). The second face 42 has two openings 44 placed on opposite sides of the curved cut-away portion aligned with the position of the flexible tube when held in a straight-through position by the inlet 16 and outlet 18 tubing supports. These openings allow observation of the fluid flow and the presence of bubbles or obstructions.

Either of the faces 38, 42 or the wall 52 can have features for holding the force-applying member in its proper position.

Figure 9:
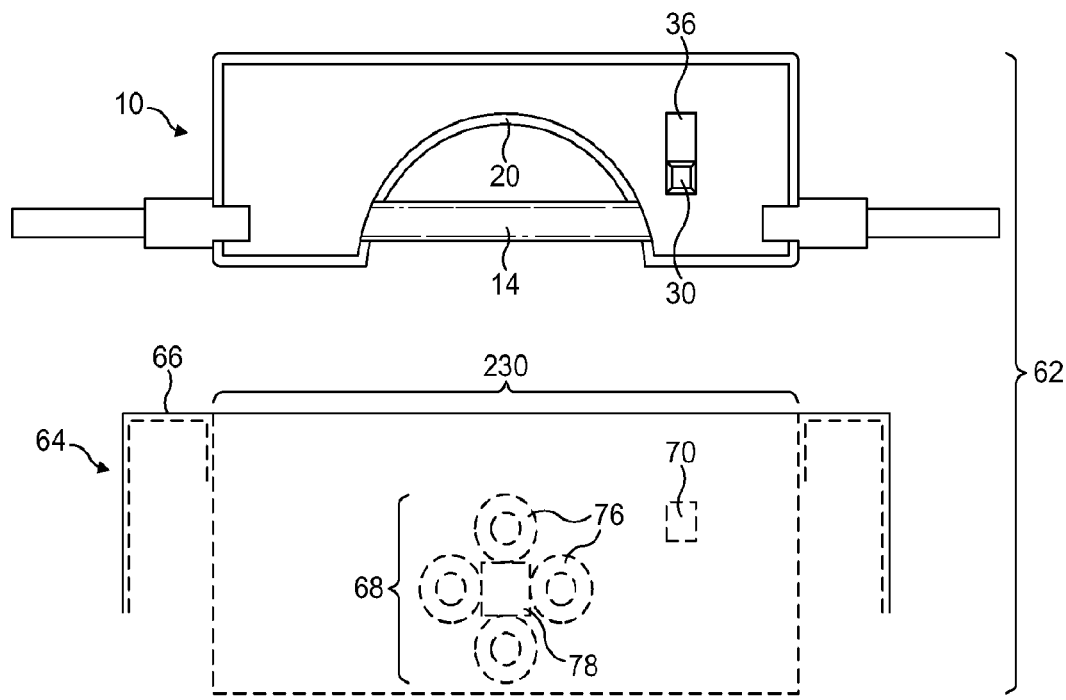
FIGS. 9-12 are a series of views showing stages of engagement of a cassette tubing and tab member with a pump mechanism and engagement mechanism for insertion of a cassette into a pump according to an embodiment of the present disclosure.
Figure 10:
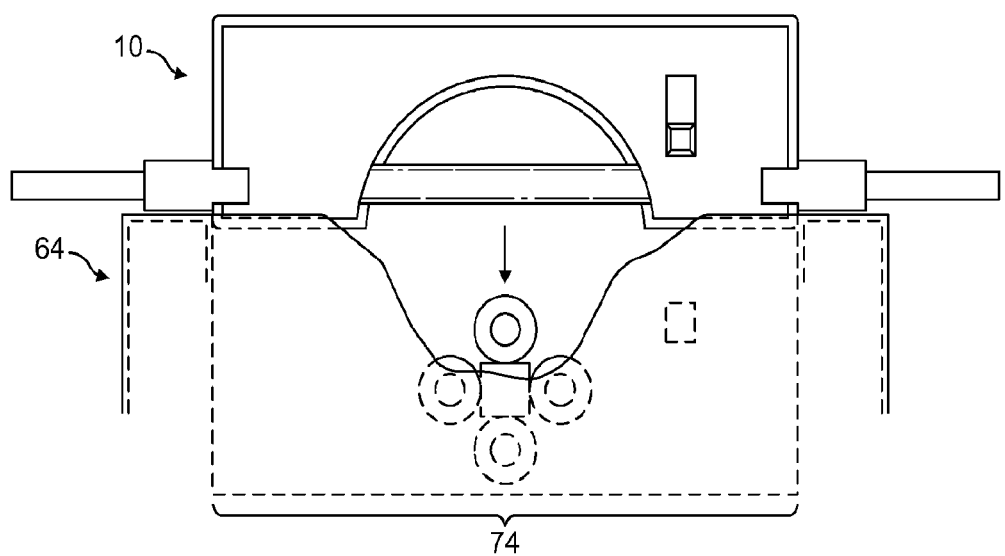

Referring to FIGS. 9-12, the cassette and infusion pump include the cassette/pump fluid delivery system 62. Referring to FIG. 9, the infusion pump 64 includes a housing 66 containing a pump mechanism 68 that engages the flexible tubing 14 of the cassette 10, an activation mechanism 70 that can engage the tab member 30 on the cassette, and optionally a feature for attaching or adjoining a cassette to the housing (not shown).

The pump housing 72 is configured and dimensioned so as to receive and engage with the cassette 10. Engagement can be achieved by either insertion of the cassette 10 into an opening 74, recess or depression in one of the faces of the housing, where the opening 74, recess or depression is configured and dimensioned to accept the cassette, or by attachment or adjoining of the cassette to a position on the exterior of the of the housing. The cassette can be attached or adjoined and secured by some feature such as tabs, clips, latches, catches, fasteners, or any combination thereof.

The pump mechanism 68 has one or more rollers 76 or fingers arranged around a central hub 78 that can rotate freely, and is configured and dimensioned to fit within the area defined by the rigid curved wall 20 of the cassette when engaging the flexible tubing. The pump mechanism 68 stretches and applies tension to the tubing 14 by pressing the tubing between the rollers 76 or fingers of the pump mechanism 68 and the rigid curved wall of the cassette 20. The stretching and tensioning occurs because the length of tubing that is initially held between the ends of the cassette in a straight line is made to take a longer path when engaged by the pump mechanism (see, FIG. 11). This engagement conforms the tubing to the space between the rigid curved wall and the pump mechanism (see, FIG. 12). The length of tubing 14 is in contact with and compressed between the curved wall 20 and the pumping mechanism rollers 76, so the pump can deliver fluid through the tube. The pumping mechanism creates the same amount of tension in the flexible tubing each and every time it is engaged with the cassette, and this tension allows a correct and accurate amount of fluid to flow through the tubing when the pumping mechanism is activated. The positioning, tensioning and amount of fluid flow are repeatable each and every time a the cassette and pump are engaged. The action of the pump mechanism causes a controlled flow of fluid of a correct and accurate amount through the flexible tubing, and restricts the flow of fluid through the tubing when stopped.

The pumping mechanism can move to engage the tubing automatically when the cassette is engaged with or inserted into the pump through the use of a sensor or trigger that detects the presence of the cassette. Movement of the pumping mechanism from a retracted position to a extended position that engages the flexible tubing can be achieved using a motor, piston or similar drive mechanism. The pumping mechanism may follow a linear or circular path between an initial position and the position where the tubing is compressed between the curved wall 20 and the pumping mechanism rollers 76. The pumping mechanism moves in the plane of the tubing, so that the rollers contact the tubing at a proper angle and stretch the tubing the proper amount, such that the tubing is accurately positioned in contact with and between the curved wall and the pumping mechanism.

In another embodiment, the pumping mechanism can rotate around an axis that is parallel to the axis of the tubing, such that the pumping mechanism swings up from a position perpendicular to the plane of the cassette to a position in the plane of the tubing.

The infusion pump 64 has an activation mechanism for engaging the tab member 30 of the anti-flow valve mechanism 34 that causes the tab member 30 to move between the fluid non-delivery position (see, FIG. 3), and a fluid delivery position (see, FIG. 4) to allow fluid flow through the tubing.

Figure 11:
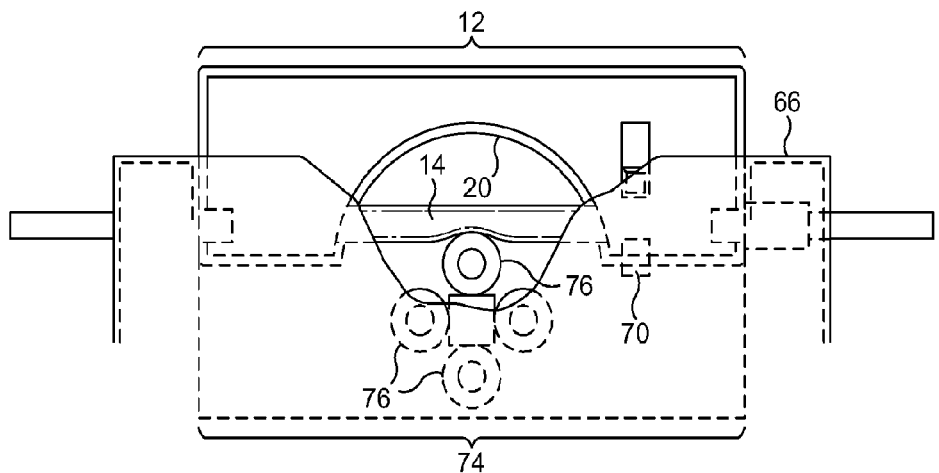
Figure 12:
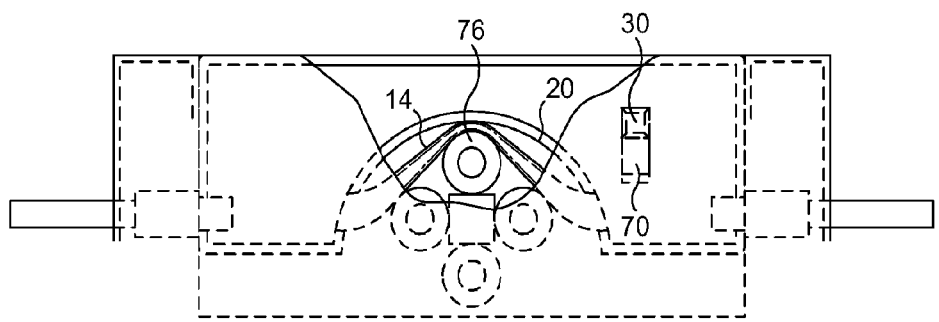

The activation mechanism can include either a protrusion or wall 80 that makes contact with the tab member 30 as the cassette engages the pump to move the tab to the fluid delivery position and to hold it there after the cassette is inserted into the infusion pump (see, FIGS. 11-12).

The protrusion or wall 80 extends from the housing of the pump and is suitably configured and dimensioned to extend into the path of the tab member, thereby preventing the tab from moving more than a specific distance into the opening 74 of the pump housing 12 when the cassette is inserted into the pump (see, FIGS. 11-12). The protrusion can be a raised feature that is essentially the same size as the tab member located in the path of the tab member. The protrusion can have any shape that can block the motion of the tab member. In an embodiment, the tab member is wedge-shaped with the flat face contacting the tab and the wedge sloping back away from the contact face. This arrangement provides the maximum contact surface between the tab 30 and activation mechanism 70 with sufficient strength and durability to withstand repeated insertion of cassettes without wearing or breaking. The protrusion should be suitably sized to avoid interference with the actual insertion of the cassette into the infusion pump. The wall extends perpendicularly across the path of the tab member, wherein the length of the wall perpendicular to the path of the tab member is at least greater than the width of the tab member, and could extend across the entire length of the opening in the infusion pump housing.

In another embodiment, the activation mechanism may be an arm or a multiple component assembly configured and dimensioned to cause the tab member to move between the fluid non-delivery position and a fluid delivery position. The activation mechanism could move the tab member as the cassette is engaged with or inserted into the pump, after the cassette is engaged with or inserted into the pump, or as or after the pumping mechanism engages the flexible tubing of the cassette. The activation mechanism can move independently of both the cassette and the pumping mechanism when moving the tab member. The sequence of engaging the cassette with the infusion pump, engaging the pumping mechanism, and moving the anti-flow valve mechanism between the delivery and non-delivery positions as well as the reverse sequence of disassociating the cassette can be altered to accommodate the particular requirements of the fluid delivery system application.

The movement of the activation mechanism may be triggered by engagement of the cassette with the pump or pumping mechanism, activation of the pumping mechanism, or may be triggered automatically by a separate triggering event, or manually by a user at some chosen time. Where engagement of the pumping mechanism with the cassette prompts the activation mechanism to push the tab member to the fluid delivery position, the movement of the tab member may be sufficiently delayed to allow the pumping mechanism rollers 76 to pinch the tubing 14 closed before the anti-flow valve mechanism 34 is moved to the fluid delivery position. This allows compression of the flexible tubing at one location before releasing the compression at another location, and thereby prevents any interim leakage though the tubing.

Engagement of the activation mechanism with the tab member can be initiated automatically upon engagement with or insertion of the cassette into the pump through the use of a sensor, switch or trigger. The engagement of the activation mechanism with the tab member may also be initiated manually by a user starting the pump or independently activating a sensor, switch or trigger. Movement of the activation mechanism to engage the tab member can be achieved using a drive mechanism such as a motor, piston or similar device. The drive mechanism can move the activation mechanism directly, or it may move the pumping mechanism directly and the activation mechanism through association with the pumping mechanism.

The removal of the cassette from the pump can automatically disengage the activation mechanism and releases the tab member so that the force-applying member returns to the biased fluid non-delivery position to prevent flow of fluid through the tubing. Alternatively, when the infusion pump activation mechanism engages the tab member 30 after the cassette is inserted into the infusion pump to allow compression of the flexible tubing by the pumping mechanism rollers 76 before moving the anti-flow valve mechanism 34 to the fluid delivery position, the activation mechanism would disengage and release the tab member 30 so that the force-applying member 46 returns the moveable member 32 to the fluid non-delivery position to prevent flow of fluid through the tubing before compression by the rollers is released and the cassette is removed from the pump. This prevents any interim leakage though the tubing.

The sequence of associating the cassette with the infusion pump, engaging the pumping mechanism, and moving the anti-flow valve mechanism between the delivery and non-delivery positions as well as the reverse sequence of disassociating the cassette can be altered to accommodate the particular requirements of the fluid delivery system application.

The infusion pump can also have one or more registration components that engage the registration grooves of the cassette. The registration components can be pins, raised tracks or other raised features that are configured and dimensioned to fit into the registration grooves in the cassette face to prevent the cassette from being associated with the pump in an incorrect manner or orientation. The registration grooves can have a variety of lengths, cross-sectional sizes and shapes including but not limited to triangular, square, rectangular, "T," and circular.

According to yet another embodiment of the present disclosure, a pinch clamp assembly for engaging a tube with an enteral feeding or infusion pump adapted to feed nutritionals or to infuse medical solutions to a patient is provided. The pinch claim assembly may include a base including holding means for holding a tube in operative engagement with the base, a first clamping surface and supporting means for supporting a connector, a clamping element having a second clamping surface engageable with the tube and moveable between an open position allowing flow of fluid through the tube and a closed position wherein the tube is occluded by the clamping element, a connector for connecting the tube with a port on a patient, the connector being removable from the pinch clamp assembly, and a spring, wherein the connector is adapted to engage with the clamping element so as to hold the clamping element in the open position, wherein the clamping element is forced from the open to the closed position by the force of the spring as soon as the connector is removed from the assembly, and wherein the clamping element is adapted to be moved from the closed to the open position when the pinch clamp assembly is mounted to the enteral feeding or infusion pump and the connector is removed.

Thereby, the free-flow condition is prevented when the pinch clamp assembly is in its delivery state because the connector which is to be connected to the port of the patient is still part of the pinch clamp assembly. As soon as the connector is removed the clamping element will automatically move to its closed position due to the force of the spring preventing any flow through the pumping section of the silicone tube. Therefore, the free-flow condition is again prevented when the respective connectors are connected to the port on the one end and to the solution or formula container on the other end. In this state, i.e., after the removal of the connector, the pinch clamp assembly may be inserted into the enteral feeding or infusion pump. When inserting the pump, the clamping element is opened due to the interaction of the pump with the clamping element. However, there is no free-flow condition because the pumping section of the silicone tube is so tightly wrapped around the pumping mechanism (rotor unit) of the enteral feeding or infusion pump that a flow of solution through the silicone tube is prevented. Thus, a free-flow condition of an infusion set including the pinch clamp assembly according to the present disclosure is avoided at all times, in particular before its first use.

The pinch clamp assembly according to the present disclosure may be stored for a long time such as five years in its delivery state because the clamping element is in its open position and the silicone tube is not compressed or pinched thus preventing degradation or sticking of the material. Also, the anti-free-flow mechanism is an integral part of the pinch clamp assembly avoiding any additional components.

The pinch clamp assembly of the present disclosure may also be tamper-resistant because for a normal user it is impossible to close the clamping element with her or his hands when the connector is still inside the assembly. Only cutting the connector with its tip separated from the remainder might lead to the free-flow condition, however, this will inevitably destroy the function of the connector where both ends include special adapters that must fit other parts such as a port, luer lock or the like.

The clamping element may be hinged at the base. This enables a rocker-like movement and mechanism and ensures the opening/closing interaction of the spring and the clamping element. A snap-in arrangement provides sufficient fixing to the clamping element.

In an embodiment, the connector is an enteral spike, an IV (intravenous) spike, an enteral feeding adapter, an IV luer lock adapter or other enteral or IV component. All possible connectors known in the art of enteral feeding or infusion can be used.

The connector may be threadedly coupled to the clamping element and/or the supporting means. This ensures that the connector is well fixed to the clamping element and prevents the connector from unintentionally falling out of the assembly. Other fixing means of the connector to the clamping element are also possible such as magnetic means, bayonet joint or the like.

In an embodiment, the base is formed as a cassette such that the pinch clamp assembly may be integrally mounted to the enteral feeding or infusion pump. A cassette provides a flat construction which is not bulky and yet includes a compact format.

In another embodiment, the base, the clamping element and the connector are made of recyclable plastic material such as thermoplastics, the spring is made of metal and the pumping section of the tube is made of silicone or silicone replacement tubing. This enables a simple recycling procedure of this one-way and single-use equipment where only the spring is of a different material.

The base may include a cylindrically-shaped holding element to accommodate spring. This ensures that the spring which is one of the core functional parts is constantly held at its place within the assembly.

In an embodiment, the clamping element has a first leg with a tube blocking portion, a second leg having means for engagement with the spring and a retainer for engagement with the connector, and a swivel pin adapted to engage with a suitable seating on the base. The tube blocking portion ensures optimal interaction with the clamping surface of the base, the means for engagement with the spring ensure that the spring is kept at its designated functional place at all times, and the retainer ensures the engagement of the connector with the clamping element.

In another embodiment, the retainer is constructed as a cap or dust cover which is adapted to accommodate the tip of the connector. This enlarges the area of guidance for the connector and thus ensures the proper engagement of the connector with the clamping element. Furthermore, it prevents dirt from getting into the opening of the connector. Also, a larger threaded area may be provided in such a cap and on the connector thus improving the engaging function.

In an embodiment, the clamping surfaces are uneven, corrugated or finned. Depending on the specific requirements of the silicone tubing, different set-ups of the clamping surfaces may be used.

The base may include a first and a second inner wall between which clamping element is arranged. This ensures a good guidance of the clamping element perpendicular to the direction of the tube and avoids a potential access point for tampering to take out the clamping element.

According to another embodiment of the present disclosure, an enteral feeding or infusion pump includes a pinch clamp assembly as mentioned above, wherein the pump has releasing means adapted to engage with the clamping element so as to release the clamping element from the closed to the open position.

In an embodiment, the flow through the pumping section is only enabled when the pinch clamp assembly is mounted. This ensures that the anti-free-flow mechanism is only disabled when the pinch clamp assembly is entirely mounted to the infusion pump.

Figure 13:
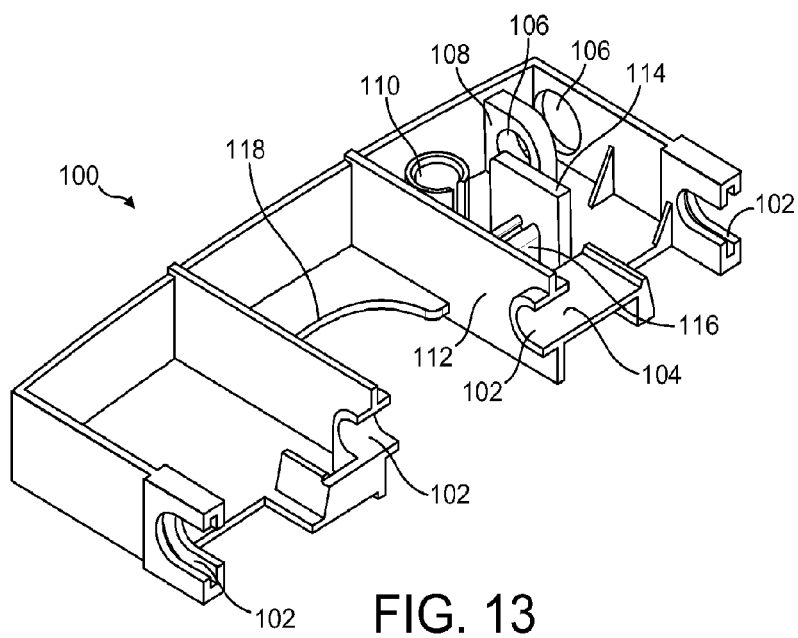
FIG. 13 shows a perspective view of a cassette according to an embodiment of the present disclosure.

FIG. 13 depicts a perspective view of the main component of an embodiment of the pinch clamp assembly according to the present disclosure, which includes cassette 100 forming the base of the assembly. Cassette 100 is configured generally rectangular and in a relatively flat structure. It is assumed that the cassette 100 is fabricated by injection molding out of a thermoplastic material such as polypropylene, polystyrene, polyethylene or acrylnitrile-butadiene-styrene (ABS), also other suitable thermoplastics may be used. Cassette 100 includes four holding means 102 at opposing sides to support the pumping section of a silicone tube (not shown in this figure). Holding means 102 to accommodate the silicone tube are positioned towards the center and near the longitudinal edge of the cassette 100.

Base or cassette 100 further includes a first clamping surface 104 adjacent to holding means 102. First clamping surface 104 is flat and substantially parallel to the general plane of cassette 100. Its area is large enough to provide optimal clamping of the tube. Supporting means 106 are provided in cassette 100 in the form of a substantially round recess formed in a sidewall of the cassette 100 and a further substantially round recess formed in an inner wall 108 which is substantially parallel to the side wall which accommodates support 106. The substantially round recesses have substantially the same axis and are provided to support a connector which will be described in more detail later.

Cassette 100 further includes a cylindrically-shaped holding element 110 which is adapted to accommodate a spring as will be explained later. Parallel inner side walls 112 and 114 are formed substantially perpendicular to the direction of the tube. In addition a seating 116 is formed on the ground plate of cassette 100. In order not to overcomplicate the figures with components not essential for the present disclosure, the tube has been omitted at this point. The bottom portion of cassette 100 has a rotor unit recess 118. When mounting the pinch clamp assembly according to the present disclosure to the enteral feeding or infusion pump the pins of the peristaltic rotor unit will fit into the space freed by the rotor unit recess 118. The claw-like contact area of holding means 102 is sufficiently large to provide a firm fit of the silicone tube.

Figure 14:
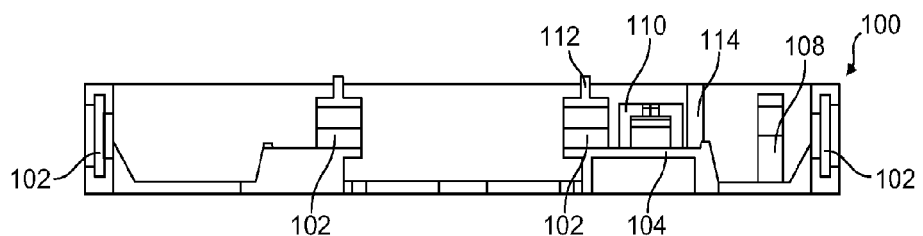
FIGS. 14-16 show a front view plan view and side view, respectively, of a cassette according to an embodiment of the present disclosure.
Figure 15:
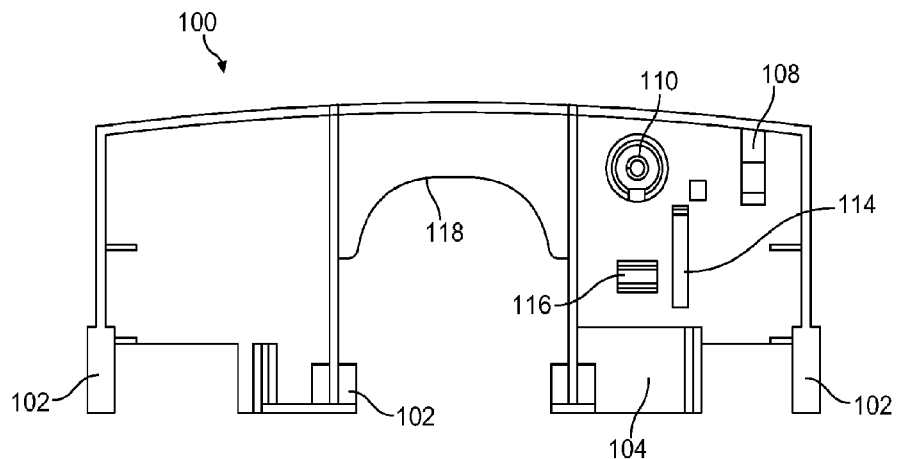
Figure 16:
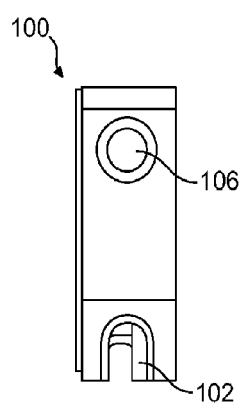

FIGS. 14, 15 and 16 are front, plan and side views of the pinch clamp assembly components of FIG. 13, wherein like numerals refer to like elements.

Figure 17:
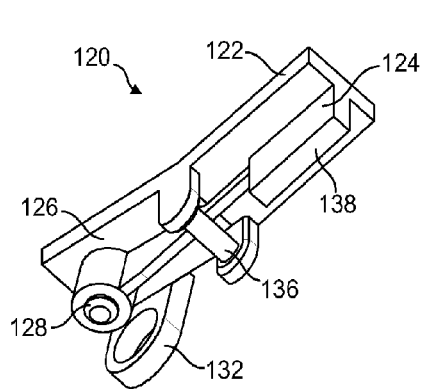
FIGS. 17-18 show perspective views of a clamping element of a pinch clamp assembly according to an embodiment of the present disclosure.
Figure 18:
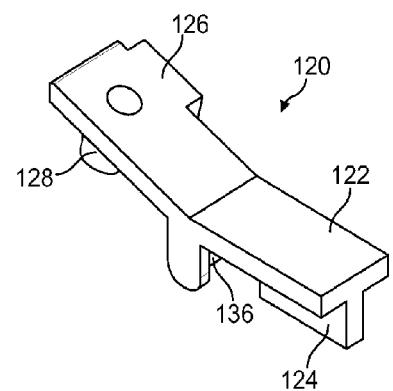
Figure 19:
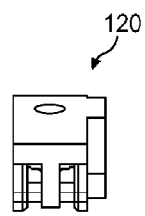
FIGS. 19-22 show a front view, left side view, plan view, and right side view, respectively, of a clamping element of a pinch clamp assembly according to an embodiment of the present disclosure.
Figure 20:
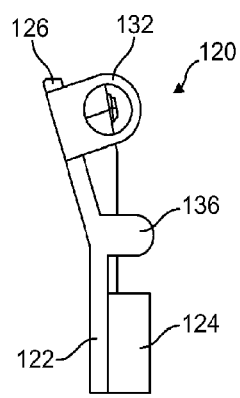
Figure 21:
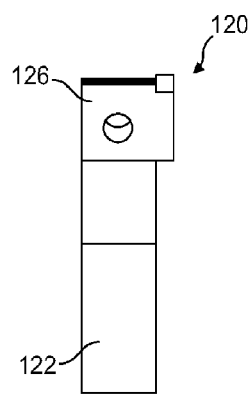
Figure 22:
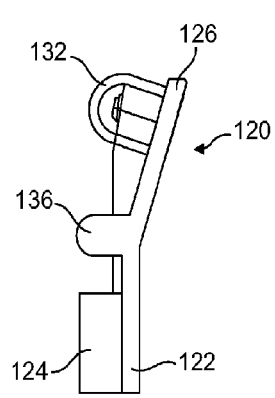

FIGS. 17, 18 show perspective views of a clamping element 120 according to an embodiment of the pinch clamp assembly of the present disclosure. Clamping element 120 is the central element of the pinch clamp assembly and is formed by first leg 122 with a tube blocking portion 124, a second leg 126 having means 128 for engagement with spring 130 (not shown) and a retainer 132 for engagement with connector 134. First leg 122 and second leg 126 stand against each other in an angle of approx. 10° to 20° so that a rocker-like setup is formed with a swivel pin 136 sitting in between. Swivel pin 136 is adapted to fit into the seating 116 formed in the cassette 100. Also, clamping element 120 is guided and enclosed between inner side walls 112 and 114. The tube blocking portion 124 has a second clamping surface 138 which is adapted to interact and engage with first clamping surface 104 of cassette 100. The means 128 are designed such that a perfect fit with spring 130 may be achieved. For stability purposes a T-bar like link between first leg 122, second leg 126, means 128 and tube blocking portion 124 is provided.

FIGS. 19, 20, 21 and 22 are front, left hand side, plan, and right hand side views, respectively of the clamping element shown in FIGS. 17 and 18, wherein like numerals refer to like elements.

In an embodiment shown in FIGS. 17 to 22, the retainer 132 is formed substantially as a ring to accommodate the tip of connector 134. It must be noted that the connection between second leg 126 and retainer 132 should be very firm to ensure an optimal operation of the clamping element 120 as part of the pinch clamp assembly according to the present disclosure.

FIGS. 23, 24 show perspective views of a clamping element 120 according to an embodiment of the pinch clamp assembly of the present disclosure. In this embodiment, the form of retainer 132 is different because retainer 132 is formed as an elongated cylindrical cap or dust cover extending substantially perpendicular to the rocking direction clamping element 120. Enlarging the ring of retainer 132 of the embodiment of FIGS. 17-18 along its central axis will lead to the shape of retainer 132 of the embodiment of FIGS. 23-24. It must be noted that shapes other than a cylindrical cap are possible. Also retainer 132 may include a flat surface on the inside or a thread. What is important is the interaction of retainer 132 with connector 134, as will be explained in detail later.

FIGS. 25, 26, 27 and 28 are front, left hand side, plan, and right hand side views, respectively of the clamping element shown in FIGS. 23 and 24, wherein like numerals refer to like elements.

Figure 29:
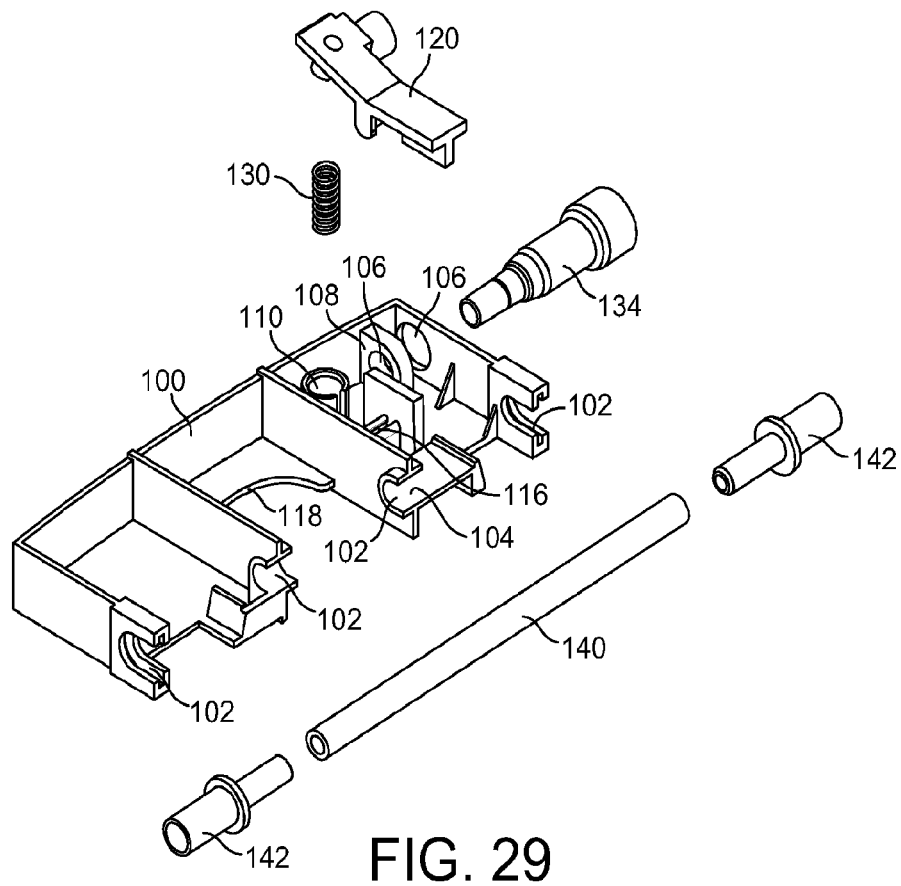
FIG. 29 shows a perspective exploded view of a pinch clamp assembly according to an embodiment of the present disclosure.
Figure 31:
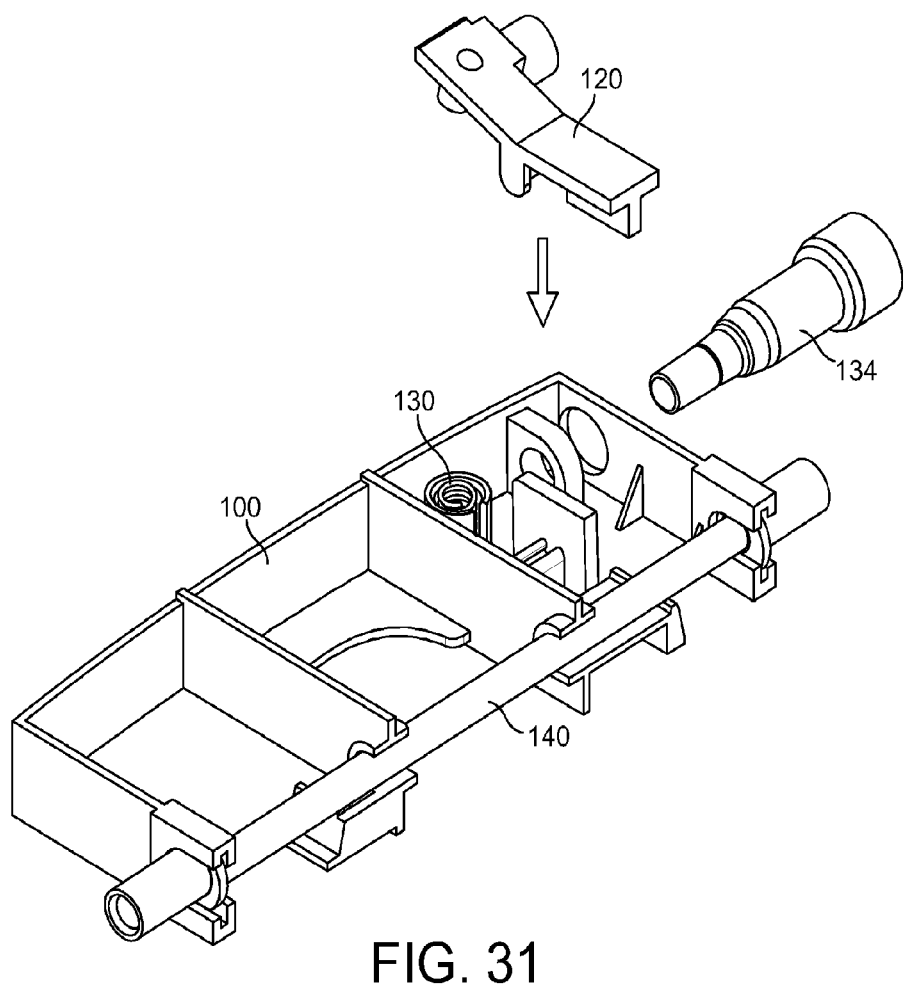
FIG. 31 shows a perspective exploded view of a pinch clamp assembly according to an embodiment of the present disclosure.

FIG. 29 shows a perspective exploded view of the embodiment of the pinch clamp assembly in FIGS. 17-18 according to the present disclosure in a status before assembly of its components. Tube 140 includes a pumping section made of silicone or any other suitable material. On either end of tube 140 two tube fitting elements 142 are provided being adapted to hold silicone tube 140 and to fit into the holding means 102 provided at the longitudinal ends in the cassette 100 of the pinch clamp assembly. In order to provide a good fit the tube fitting elements 142 have a flange which is adapted to engage the recesses formed in the holding means 102 of cassette 100. FIG. 31 shows the tube 140 fitted into the pinch clamp assembly according to the present disclosure. It is to be noted, that usually only the pumping section of the tubing portion of the entire infusion set is made of silicone, whereas the remaining portions of the tube are made of PVC (polyvinylchloride). Further it must be noted that the other components of an infusion set like the PVC tube are not depicted in the accompanying drawings.

Figure 30:
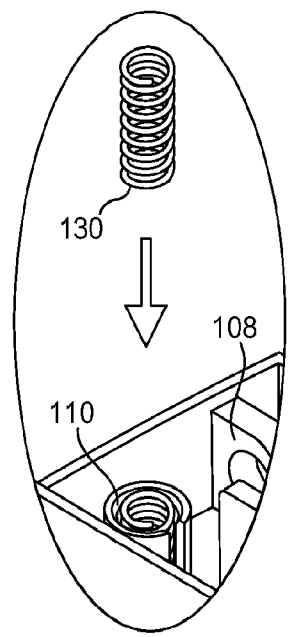
FIG. 30 shows a pinch clamp assembly having a spring according to an embodiment of the present disclosure.

Another component of the pinch clamp assembly according to the present disclosure is spring 130, which may be of metal or other suitable material with like characteristics. Before the clamping element 120 can be mounted to the cassette or base 100, the spring 130 must be inserted in the cylindrically-shaped holding element 110, as can be seen in detail in FIG. 30. Thereafter, the connector 134, which in the shown embodiment is an enteral adapter, may be mounted to the assembly together with the clamping element 120 (see, FIG. 31). The swivel pin 136 of clamping element 120 must be inserted in the seating 116 of cassette 100 against the force of the spring 130. Thereby, the tube 140 will be compressed between the first and second clamping surfaces 104 and 138 on base 100 and the tube blocking portion 124 of clamping element 120. In the shown embodiment, the clamping surfaces of the tube blocking portion 124 and the second leg 126 are flat. However, it is possible that the clamping surfaces are uneven, corrugated or finned so as to facilitate the squeezing function of the clamping element 120 depending on the characteristics of the silicone tube.

Figure 32:
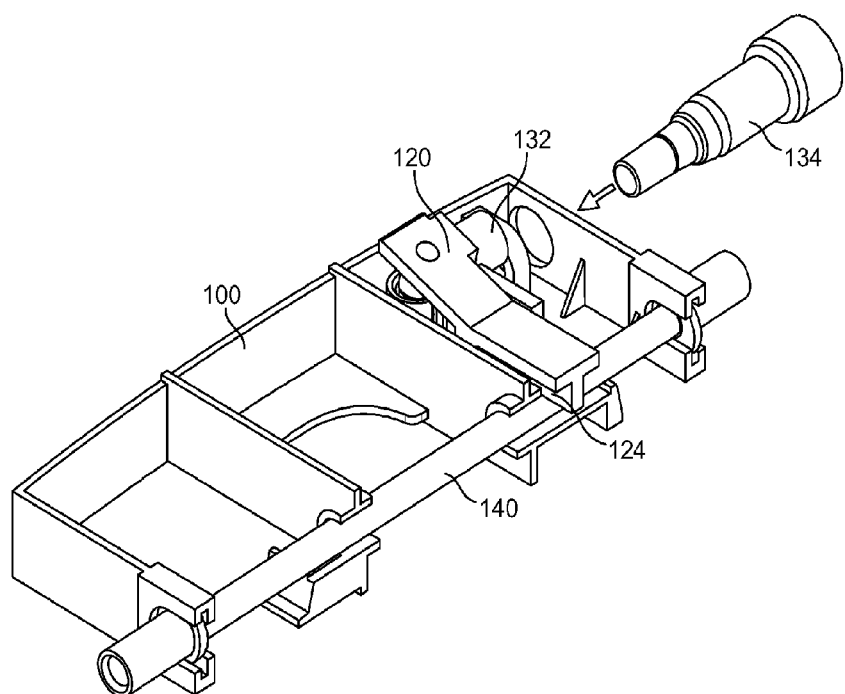
FIG. 32 shows a perspective exploded view of a pinch clamp assembly according to an embodiment of the present disclosure.

The tube must not be compressed during the delivery status of the pinch clamp assembly. Therefore, the clamping element 120 must somehow be tilted such that the clamping surfaces stay apart. This may be achieved by holding down the clamping element 120 on the second leg 126 so that the spring 130 is compressed with one end in the cylindrically-shaped holding element 110 and the other end on means 128. Then, in the lowest position of the second leg 126, i.e., when means 128 substantially touch the cylindrically-shaped holding element 110, the connector 134 which is meanwhile inserted through the supports 106 in the side wall and in the inner wall 108 of cassette 100 (see, FIG. 32), is moved along its axis further with its tip such that it is inserted into the retainer or cap 132 of clamping element 120. Retainer or cap 132 of FIGS. 23-24 may be formed as a cylinder which is closed on the clamping element side thus preventing dust to enter the connector 134 when in engagement. This engagement serves as a locking mechanism keeping the clamping element 120 down on the side of the second leg 126 which in turn means that the first leg 122 is kept on top such that the first and second clamping surfaces 104 and 138 are apart and thus freeing tube 140. This position where the tube 140 is open and the clamping element 120 is held down against the force of the spring 130 is called the open position.

Figure 33:
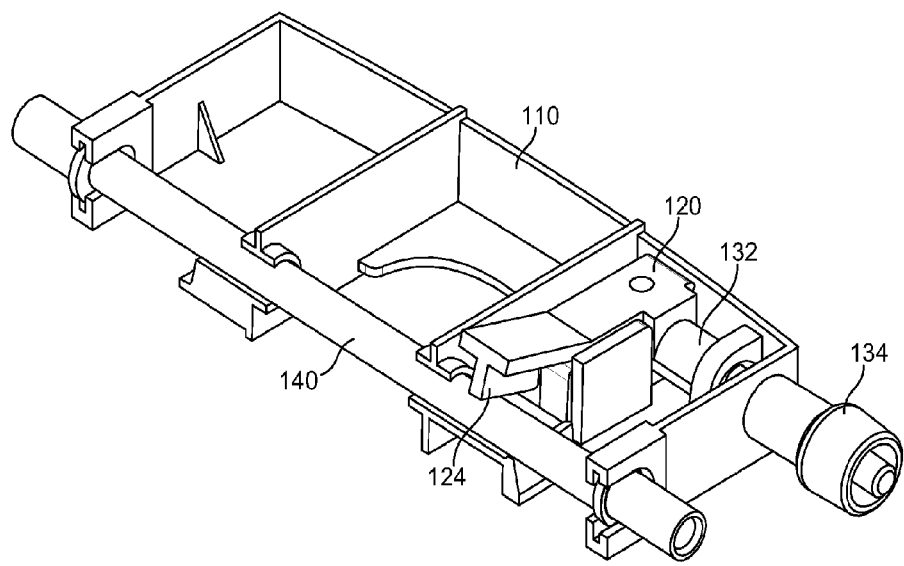
FIG. 33 shows a perspective view of a pinch clamp assembly in delivery status according to an embodiment of the present disclosure.
Figure 34:
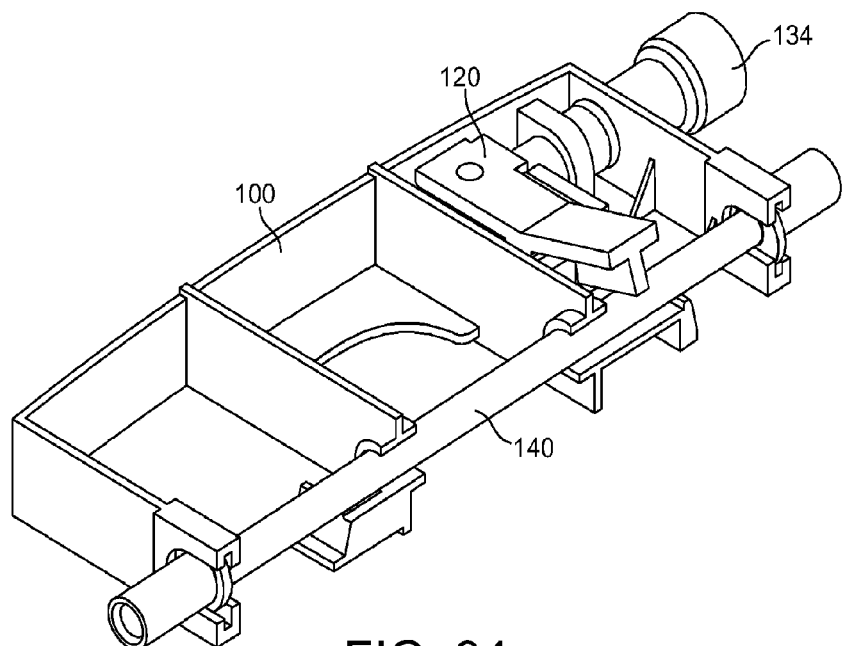
FIGS. 34-35 show a pinch clamp assembly according to an embodiment of the present disclosure.
Figure 35:
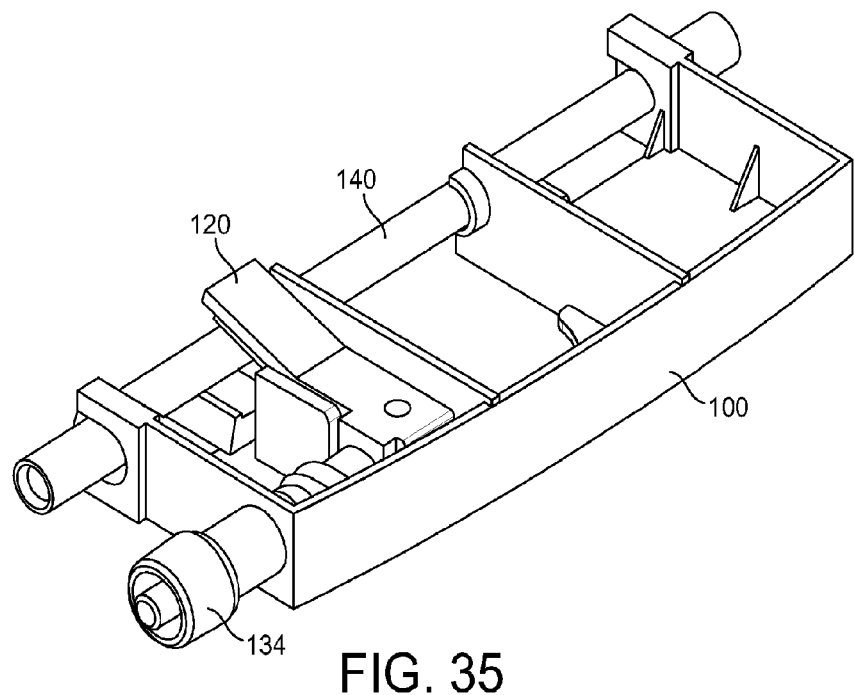

FIGS. 33, 34 and 35 show the embodiment of FIGS. 23-24 of the pinch clamp assembly according to the present disclosure in the open position, viewed from different sides. It must be noted that the connector 134 is firmly engaged with the retainer 132 such that it cannot fall out of the assembly without pulling in axial direction. The FIGS. show as connector 134 an enteral adapter which on one end has a tapered fit. It is to be noted that other types of connectors may be used and that the connector 134 is on its outwardly directing end directly connected to a tube, e.g., via solvent bonding. Also, luer type locks may be used for connecting to a tube.

The engagement between the connector 134 and the retainer 132 and/or the supports 106 in the sidewall of the cassette 100 and the inner wall 108 may be improved by providing a thread on the opposing surfaces. This may be useful in the embodiment of FIGS. 23-24 where the retainer 132 is formed as cap or dust cover.

As stated before, the open position with the connector 134 mounted in the pinch clamp assembly represents the delivery status. In order to mount the pinch clamp assembly in an enteral feeding or infusion pump the connector 134 must be removed from the assembly, must be mounted to the port of the patient, and the assembly without connector 134 must be inserted into the corresponding slot in the pump.

As soon as the connector 134 is removed from the pinch clamp assembly, the clamping element will go to the closed position thereby blocking the flow through the tube 140. Removing the connector 134 means moving the tip of the connector away from its engagement with retainer 132 (cap/dust cover or ring). This disengagement releases the spring 130 which will push against the means 128 of clamping element 120 and move the second leg 126 up. In turn, this will lead to an immediate closure of the tube 10 as the clamping surfaces 104 and 138 are pressed against each other with the silicone tube 140 in between. The clamping element 120 thus serves a tilting switch opening and closing the flow through the tube 140 depending on the status of the spring 130. The closed position can be seen in FIGS. 36 and 37 showing different perspective views of the embodiment of FIGS. 23-24 of the pinch clamp assembly according to the present disclosure.

While connector 134 is firmly engaged in and thus integral part of the pinch clamp assembly, the assembly may be in delivery state and in open position. It is not possible to generate a free flow condition since the connector 134 is held tightly within the assembly and removing the connector 134 from the assembly will immediately bring the clamping element 120 to its closed position. Thus, the flow through the silicone tube 140 is always occluded before inserting the pinch clamp assembly into the pump.

Figure 36:
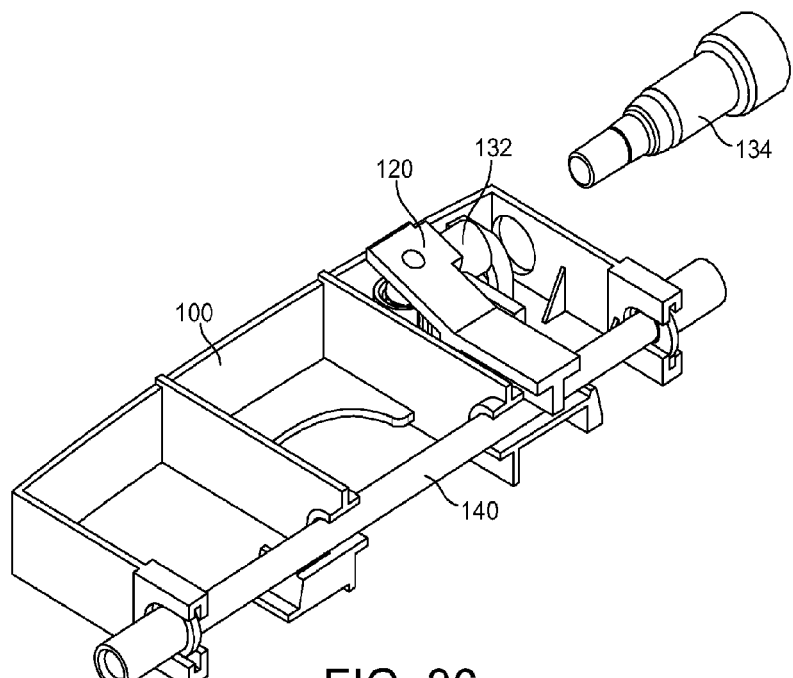
FIGS. 36-37 show perspective views of a pinch clamp assembly with a clamping element removed according to an embodiment of the present disclosure.
Figure 37:
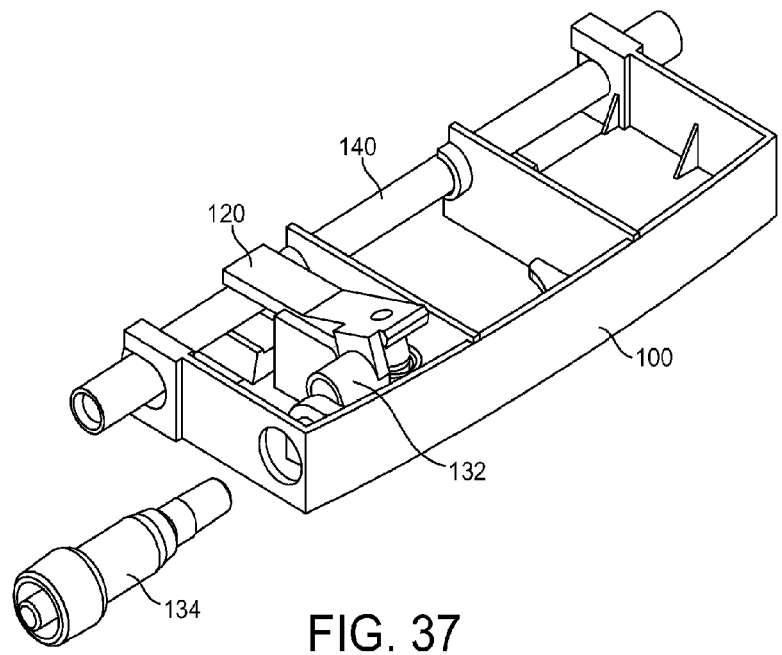

It is to be noted that the pinch clamp assembly as shown in FIGS. 36 and 37 is adapted to be mounted to an enteral feeding or infusion pump as is. Of course, before the mounting can take place, connector 134 has to be removed. When mounting the pinch clamp assembly, with connector 134 removed, to the enteral feeding or infusion pump the clamping element 120 is still in its closed position thereby occluding the flow of liquid through the pumping section of silicone tube 140. The free flow condition is thus avoided. However, the occluded status of the pumping section of the silicone tube 140 must be released as soon as the cassette 100 with the other components of the pinch clamp assembly is inserted into the enteral feeding or infusion pump. From FIGS. 36 and 37 it can be seen that the second leg 126 protrudes with its upper surface from the upper surface of the rest of the assembly. Therefore, the pump includes releasing means that will press down the second leg 126 of the clamping element 120 against the force of the spring 130 thus bringing the clamping surfaces 104 and 138 apart so as to open the flow through the tube 140. The skilled artisan will contemplate a variety of designs for the pump in order to press down the second leg 126 of the clamping element 120.

In an embodiment, a locking and releasing mechanism has been described. It is to be noted, that other locking-releasing mechanisms are possible such as a magnetic solution or a solution with fastening means. All alternative solutions, however, should be tamper-resistant so that the clamping element 120 cannot be opened easily by hand or with tools which are easily available to medical personnel without the connector 134 removed.

With the subject-matter of the present disclosure a pinch clamp assembly for engaging a tube with an enteral feeding or an infusion pump adapted to feed nutritionals or to infuse medical solutions to a patient has been provided, which has a relatively simply construction, ensures an anti-free-flow mechanism that works at all times, and allows for a long time storage of the silicone tube.

In another embodiment, the present disclosure relates to flow control devices and methods of using the flow control devices. In a general embodiment, the present disclosure provides a cassette including a housing having a constrictor, a tube attached to the housing and positioned through the constrictor, and a ball positioned inside the tube. In this configuration, the ball and constrictor combination form the anti-free flow mechanism. The ball restricts fluid flow through the tube when the cassette is not in use. The cassette can be part of an enteral administration device or system that administers nutritional compositions to a person or patient in need of same.

The cassette that houses the anti-free flow mechanism provides the user an elegant way to install the anti-free flow mechanism and feeding tube set into a pumping device via features built into a housing of the cassette and also provides other built in functionality (sensor ports, etc.) for successful delivery of the nutritional composition to a person or patient. The anti-free flow mechanism prevents leakage/flow of the nutritional composition in the enteral feeding tube set, for example, in the following instances: 1) before and after the feeding tube set is primed with the feeding fluid, 2) during the loading and unloading of the feeding tube set into and out of the pumping device and 3) after the feeding tube set has been removed from the pumping device.

As used herein, the term "nutritional composition" includes, but is not limited to, complete nutritional compositions, partial or incomplete nutritional compositions, and disease or condition specific nutritional compositions. A complete nutritional composition (i.e., those which contain all the essential macro and micro nutrients) can be used as a sole source of nutrition for the patient. Patients can receive 100% of their nutritional requirements from such complete nutritional composition. A partial or incomplete nutritional composition does not contain all the essential macro and micro nutrients and cannot be used as a sole source of nutrition for the patient. Partial or incomplete nutritional compositions can be used as nutritional supplements.

Figure 38:
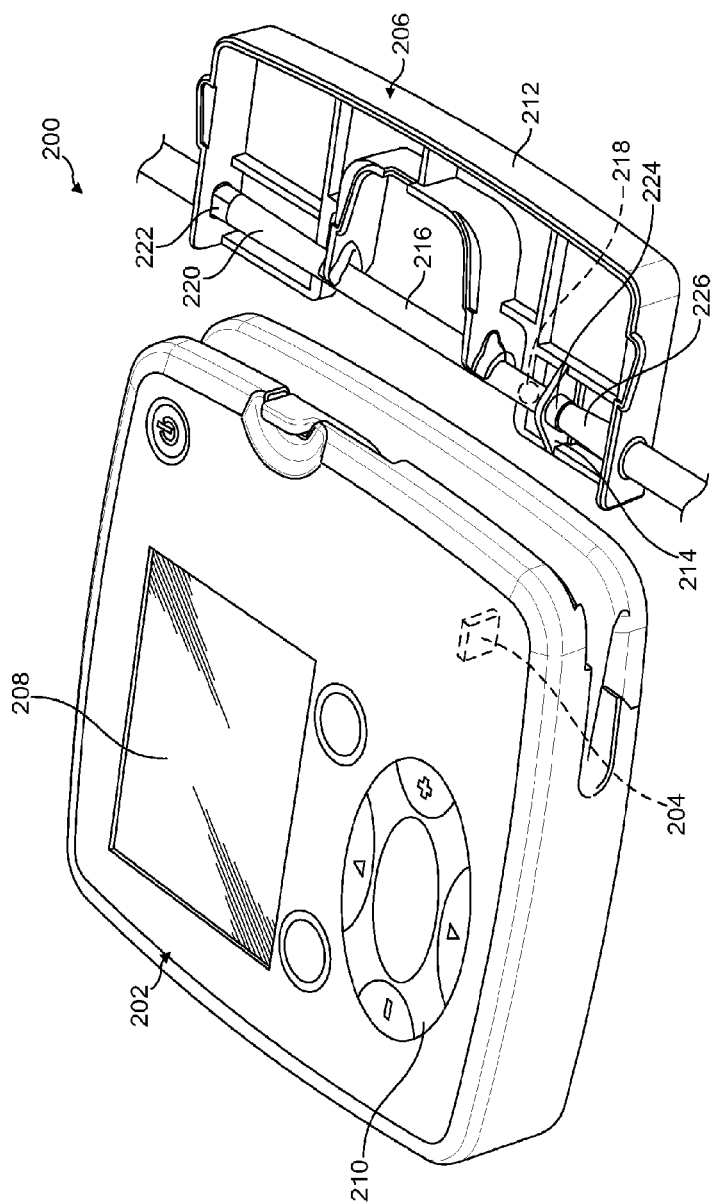
FIG. 38 shows a pumping device and a cassette having an anti-free flow mechanism according to an embodiment of the present disclosure.
Figure 39:
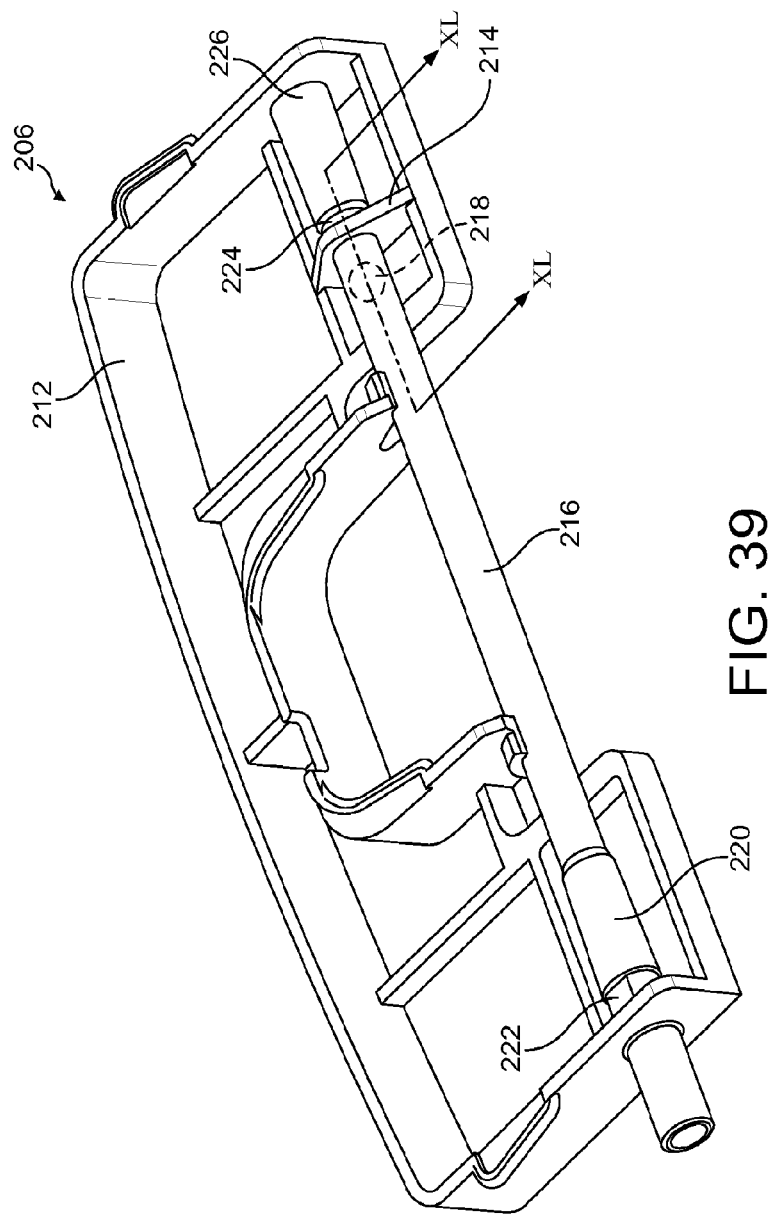
FIG. 39 shows a cassette having an anti-free flow mechanism according to an embodiment of the present disclosure.

In an embodiment illustrated in FIGS. 38-39, the present disclosure provides a flow control system 200 including a pumping device 202 having a dislodging mechanism 204. Flow control system 200 further includes a cassette 206 removably attached to pumping device 202. The design of cassette 30 can help in loading an enteral feeding tube set (not shown) into pumping device 202 without having to route/guide the tubes or stretch the tubes from the tube set over a rotor (e.g., part of a peristaltic pump).

Pumping device 202 can be an enteral feeding pump. Non-limiting examples of pumping devices are described in U.S. Pat. No. 6,659,976, which is incorporated herein by reference. Pumping device 202 can include a monitor/information screen 208 and a control pad 210 for operating pumping device 202.

Cassette 206 can have any suitable shape such as the one shown in FIGS. 38-39 and is design to be positioned within pumping device 202. Non-limiting examples of alternative cassette configurations are described in U.S. Pat. Nos. D504,506, D505,199, D455,489, D501,924 and D507,647, which are incorporated herein by reference. Cassette 206 can be made from any suitable rigid, semi-rigid or flexible material. Cassette 206 can also be "keyed/poka yoked" such that it can be inserted into pumping device 202 only one way.

As illustrated in FIGS. 38-39, cassette 206 includes a housing 212 having a constrictor 214 constructed and arranged to align with dislodging mechanism 204 of pumping device 202 when cassette 206 is positioned within pumping device 202. A flexible tube 216 is attached to housing 212 and positioned through constrictor 214. Flexible tube 216 can be made of any suitable materials such as silicone. It should be appreciated that any suitable portion of flexible tube 216 can be flexible while the remaining portion is rigid or semi-rigid.

Figure 40:
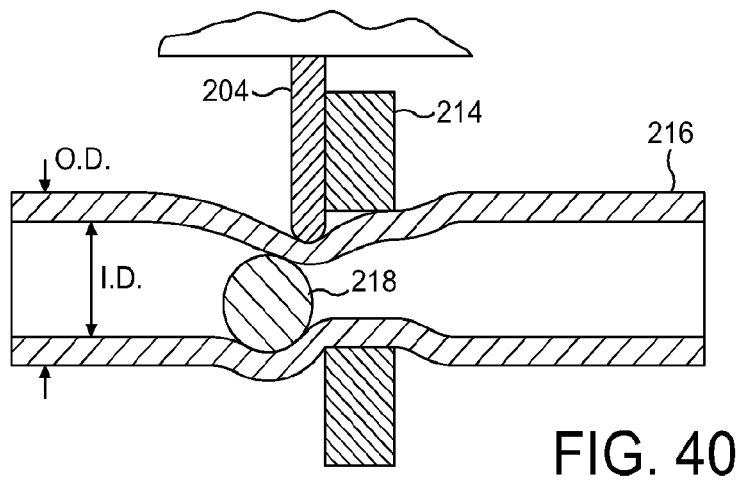
FIG. 40 shows a cross-section view XL-XL of the anti-free flow mechanism shown in FIG. 39.

A ball 218 is located or positioned inside flexible tube 216. Constrictor 214 is constructed and arranged to prevent ball 218 from moving through flexible tube 216 at the location proximate constrictor 214. For example, constrictor 214 can define a hole or passage that is slightly smaller than the outside diameter ("OD") of flexible tube 216 that is assembled in cassette 206 as seen in FIG. 40. It should be appreciated that ball 218 can have any suitable shape (e.g., spherical, cube, polygonal) to match the inner diameter ("ID") shape of the passageway of flexible tube 216.

Flexible tube 216 can include a first end 220 attached to an inlet port 222 and a second end 224 attached to an outlet port 226. As a result, fluid can flow through flexible tube 216 in the direction from first end 220 to second end 224. Inlet port 222 can be attached to a tube connected to a nutritional composition source. Outlet port 226 can be attached to a tube connected to the person receiving the nutrition composition.

In alternative embodiments, inlet port 222 and outlet port 226 can include upstream and downstream occlusion detection sensors (not shown), respectively. The term "upstream" refers to the section of the tube between a nutritional composition source (e.g., feed bag) and a pump rotor (e.g., peristaltic pump) used to provide fluid flow. The term "downstream" refers to the section of the tube between the pump rotor and a distal end connector to a person receiving the nutritional composition.

Cassette 202 can include sensor ports and sensor windows built-in. For example, the shape and size of the ports and windows can work uniquely with the sensors in the pumping device to detect upstream and downstream occlusion and/or to detect air in the fluid flow line or tubing. In addition, any portion of cassette 206 can incorporate other features to prevent cassette 206 from being incorrectly inserted into pumping device 202.

During operation, when flexible tube 216 is inserted into constrictor 214, flexible tube's 216 OD will conform to the size of the hole of constrictor 214 and proportionally reduce the ID of flexible tube 216. Ball 218 is placed inside flexible tube 216 of cassette 206, directly in the flow path of the fluid and in the upstream side of the constrictor 214 (see, FIG. 40). Ball 218 is sized such that, it is larger than the reduced ID of flexible tube 216 at the location proximate constrictor 214.

When a fluid in flexible tube 216 is under pressure, ball 218 will be pushed towards and against constrictor 214 (see, FIG. 40). Because ball 218 is larger than the reduced ID of flexible tube 216 at constrictor 214, ball 218 will squeeze flexible tube 216 against the surface of constrictor 214. As a result, the tube material between ball 218 and constrictor 214 acts as a gasket or o-ring to prevent ball 218 from passing through constrictor 214.

The fluid pressure acting on ball 218 forces ball 218 against the gasket formed and occludes the fluid flow path through flexible tube 216. With increasing pressure, the sealing force on ball 218 increases proportionally thereby creating a much better seal to prevent fluid flow.

Figure 41:
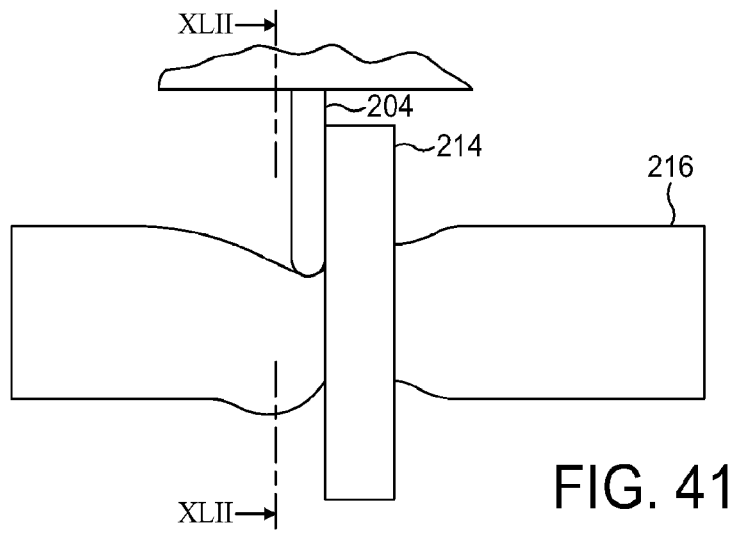
FIG. 41 shows a partial side view of the anti-free flow mechanism shown in FIG. 39.
Figure 42:
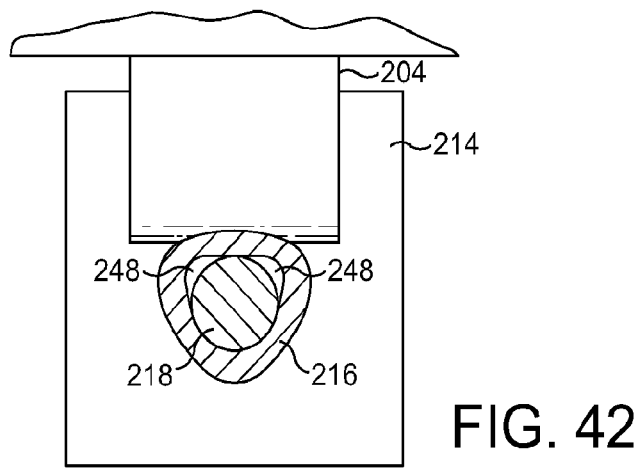
FIG. 42 shows a cross-section view XLII-XLII of the anti-free flow mechanism shown in FIG. 40.

To un-occlude or allow fluid flow through flexible tube 216, ball 218 is mechanically dislodged by dislodging mechanism 204, which can be incorporated in pumping device 202 as shown in FIGS. 38 and 40-42. As seen in FIGS. 40-42, dislodging mechanism 222 will push on the outer surface of flexible tube 216 and dislocate ball 218 by moving ball 218 out of its seated/sealing position. Once ball 218 is dislocated/dislodged, the flow path is open and fluid will flow through flexible tube 216 through newly formed voids 248 due to the distortion of the ID of flexible tube 216.

On removal of dislodging mechanism 204 (e.g., by removing cassette 206 from pumping device 202), ball 218 will reseat itself (due to the elasticity of flexible tube 218 and the fluid pressure that acts on it) in constrictor 214 and seal the flow path once again (see, FIG. 40). As a result, the anti-free flow mechanism can be unlocked and deactivated by pump 202 when cassette 206 is inserted and reactivated when it is removed from pump 202. Unlike conventional anti-free flow devices in existing enteral feeding tube sets, cassette 206 is not deactivated by closing a door, by pressure, or a roller clamp. Instead, it will be deactivated by physically dislodging ball 218 via a feature in pumping device 202.

In sum, the anti-free flow mechanism inside cassette 206 can be activated by pressure and deactivated via mechanically displacing ball 218. No spring is required in the system to activate the anti-free flow mechanism. Pressure acting on ball 218 will seal the flow path thereby preventing flow through flexible tube 216. This anti-free flow mechanism prevents any static pressure loss during pumping. When cassette 206 is inside pumping device 202, the flow can be prevented/controlled by pump rollers (e.g., peristaltic pumps) within pumping device 202.

Figure 43:
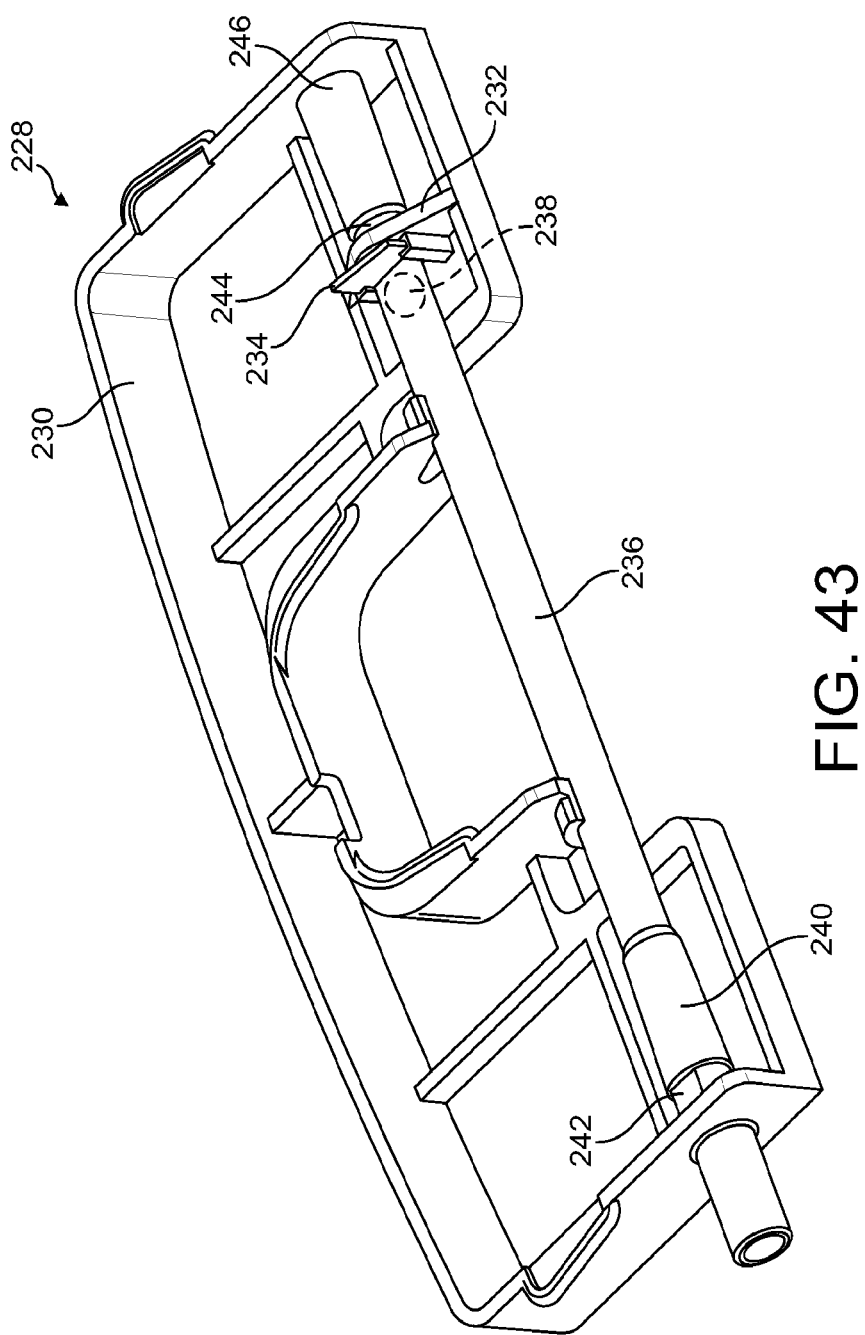
FIG. 43 shows a cassette having an anti-free flow mechanism according to an embodiment of the present disclosure.

In an alternative embodiment illustrated in FIG. 43, the present disclosure provides a cassette 228 including a housing 230 having a constrictor 232 and a dislodging mechanism 234 movably attached at nor near constrictor 232. A flexible tube 236 is attached to housing 230 and positioned through constrictor 232. A ball 238 is positioned inside flexible tube 236. Constrictor 232 is constructed and arranged to prevent ball 238 from moving through flexible tube 236 at the location proximate constrictor 232. Flexible tube 236 can include a first end 240 attached to an inlet port 242 and a second end 244 attached to an outlet port 246. Cassette 228 can be removably attached to any suitable pumping device.

A pumping device compatible with cassette 228 does not need to include any dislodging mechanism. In this regard, when cassette 228 is inserted into the pumping device, a surface of the pumping device can push down on dislodging member 234 into flexible tube 236 and cause dislodging member 234 to dislodge or move ball 238 from its position at or near constrictor 232. As a result of the distortion of flexible tube 236, fluid can flow past ball 238. When cassette 228 is removed from the pumping device, flexible tube 236 can reform to its original shape thereby allowing ball 238 to be re-positioned at or near constrictor 232 and block flow in flexible tube 236.

In yet another embodiment, the present disclosure provides a method of controlling fluid flow in a tube. The method includes providing a cassette including 1) a housing having a constrictor, 2) a tube attached to the housing and positioned through the constrictor, and 3) a ball positioned inside the tube. Fluid flow is occluded through the tube by positioning the ball within the tube at a location proximate the constrictor. The method further includes passing fluid through the tube by dislodging the ball within the tube.

In an embodiment, the ball is dislodged when the cassette is positioned inside a pumping device. For example, a dislodging mechanism can be attached to the cassette and constructed and arranged to dislodge the ball when the cassette is positioned inside a pumping device. Alternatively, a dislodging mechanism can be attached within a pumping device and constructed and arranged to dislodge the ball when the cassette is positioned inside a pumping device.

In yet another embodiment, the present disclosure relates to flow control devices and methods of using the flow control devices. In a general embodiment, the present disclosure provides a cassette including a housing having a flow restrictor, and a tube attached to the housing and positioned adjacent the flow restrictor. The flow restrictor may include a locking member in combination with a spring and/or a peg that is attached to the housing. In this configuration, the locking member of the flow restrictor is so constructed and arranged to rotate from a first position that restricts fluid flow through the tube to a second position that allows fluid to flow through the tube. The arrangement of the locking member in the first position restricts fluid flow through the tube when the cassette is not in use. The cassette can be part of an enteral administration device or system that administers nutritional compositions to a person or patient in need of same.

The cassette that includes the flow restriction mechanism provides the user an elegant way to install the flow restriction mechanism and feeding tube set into a pumping device via features built into a housing of the cassette and may also provide other built in functionality for successful delivery of the nutritional composition to a person or patient. The flow restriction mechanism prevents leakage/flow of the nutritional composition in the enteral feeding tube set, for example, in the following instances: 1) before and after the feeding tube set is primed with the feeding fluid, 2) during the loading and unloading of the feeding tube set into and out of the pumping device and 3) after the feeding tube set has been removed from the pumping device.

Figure 44:
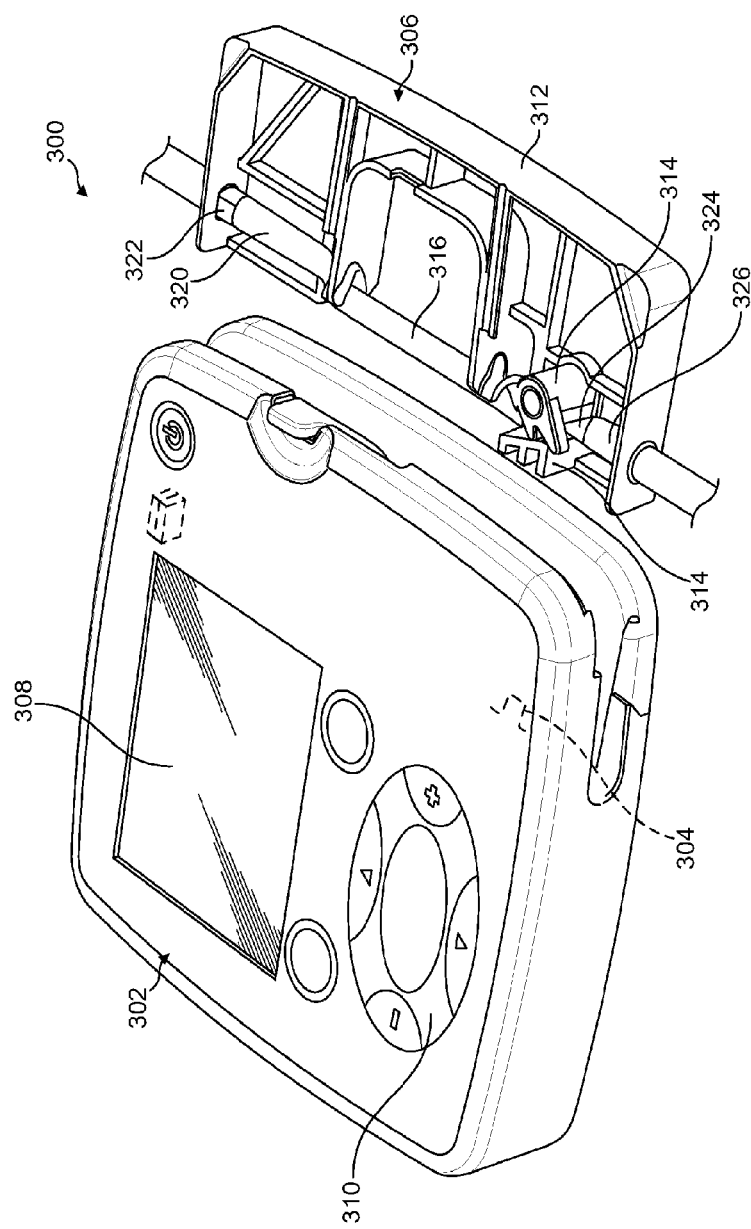
FIG. 44 shows a pumping device and a cassette having a flow restriction mechanism according to an embodiment of the present disclosure.
Figure 45:
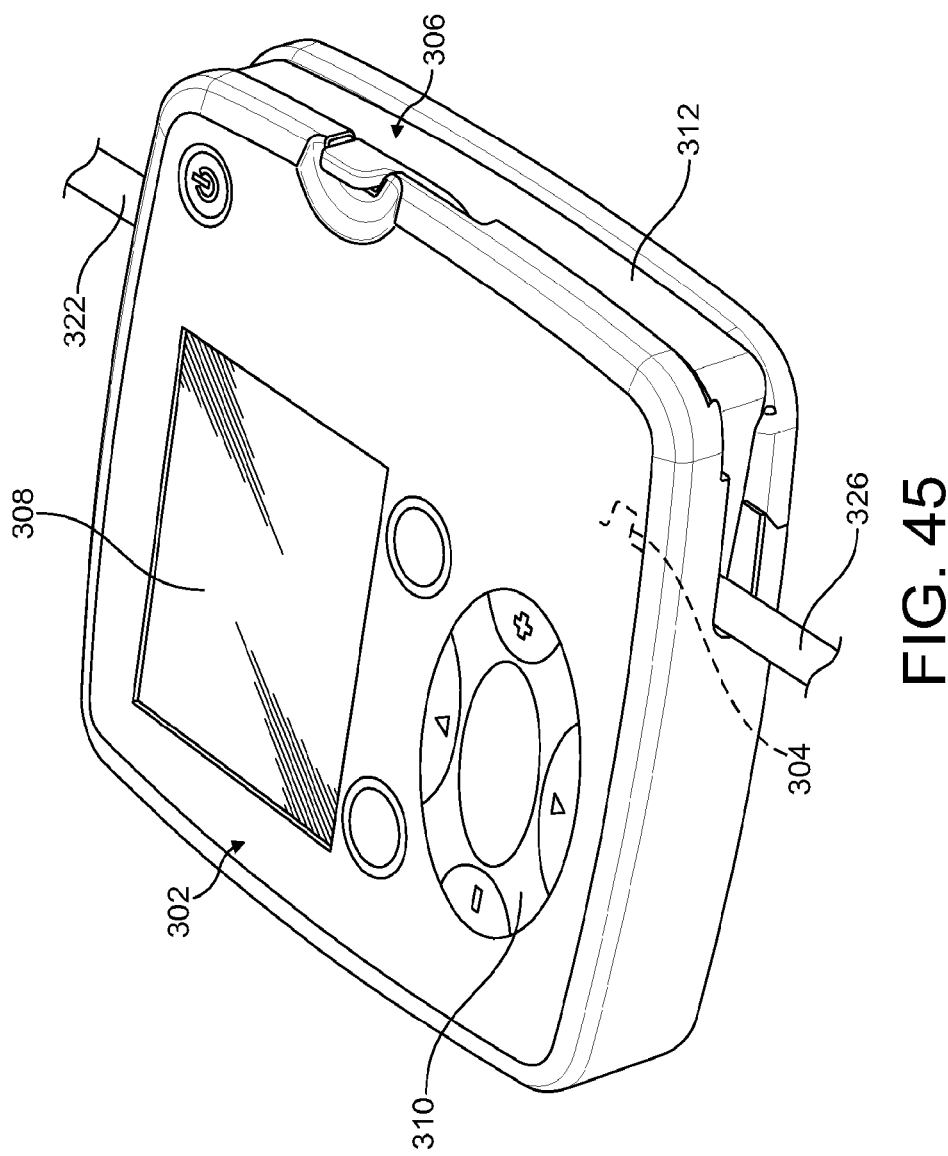
FIG. 45 shows the pumping device and the cassette of FIG. 44 with the cassette inserted into the pumping device according to an embodiment of the present disclosure.

In an embodiment illustrated in FIGS. 44-45, the present disclosure provides a flow control system 300 including a pumping device 302 having an actuation member 304. Flow control system 300 further includes a cassette 306 removably attached to pumping device 302. The design of cassette 306 can help in loading an enteral feeding tube set (not shown) into pumping device 302 without having to route/guide the tubes or stretch the tubes from the tube set over a rotor (e.g., part of a peristaltic pump).

Pumping device 302 can be an enteral feeding pump. Non-limiting examples of pumping devices are described in U.S. Pat. No. 6,659,976, which is incorporated herein by reference. Pumping device 302 can include a monitor/information screen 308 and a control pad 310 for operating pumping device 302.

Figure 46:
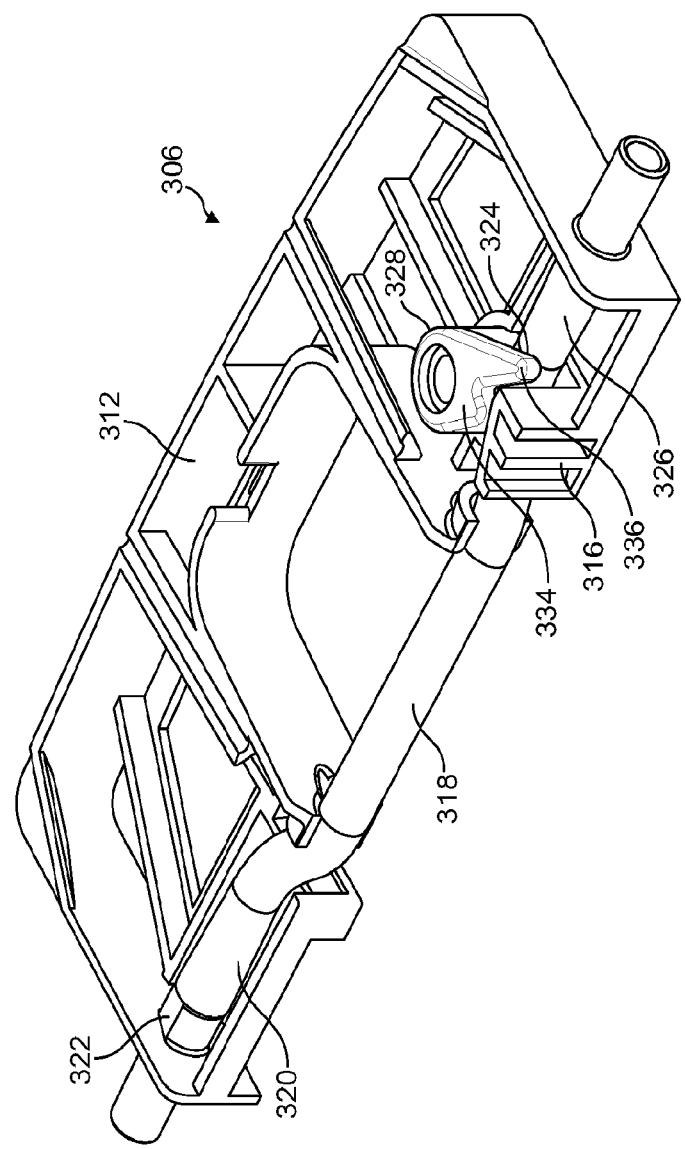
FIG. 46 shows a cassette having a flow restriction mechanism according to an embodiment of the present disclosure.
Figure 47:
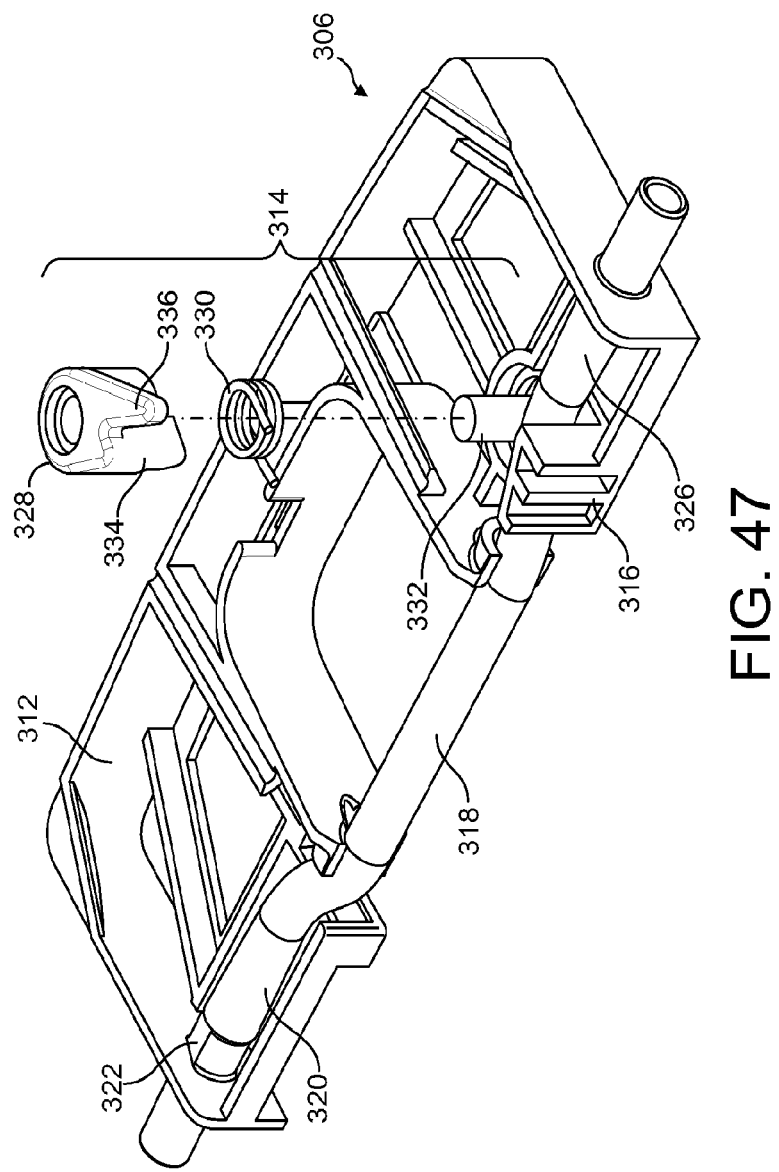
FIG. 47 shows an exploded view of a cassette having a flow restriction mechanism according to an embodiment of the present disclosure.

Cassette 306 can have any suitable shape such as the one shown in FIGS. 44 and 46-47 and is design to be positioned within pumping device 302. Non-limiting examples of alternative cassette configurations are described in U.S. Pat. Nos. D504,506, D505,199, D455,489, D501,924 and D507,647, which are incorporated herein by reference. Cassette 306 can be made from any suitable rigid, semi-rigid or flexible material. Cassette 306 can also be "keyed/poka yoked" such that it can be inserted into pumping device 302 only one way.

As illustrated in FIGS. 44-45, cassette 306 includes a housing 312 having a flow restrictor 314 constructed and arranged to align with actuation member 304 of pumping device 302 when cassette 306 is inserted into pumping device 302. Housing 312 further includes a stopper 316 located or positioned adjacent flexible tube 318 on a side of flexible tube 318 opposite flow restrictor 314. Flexible tube 318 is attached to housing 312 and positioned adjacent flow restrictor 314. Flexible tube 318 can be made of any suitable materials such as silicone. It should be appreciated that any suitable portion of flexible tube 318 can be flexible while the remaining portion is rigid or semi-rigid.

Flexible tube 318 can include a first end 320 attached to an inlet port 322 and a second end 324 attached to an outlet port 326. As a result, fluid can flow through flexible tube 318 in the direction from first end 322 to second end 324. Inlet port 322 can be attached to a tube connected to a nutritional composition source. Outlet port 326 can be attached to a tube connected to the person receiving the nutrition composition.

As is shown in FIG. 47, in an embodiment, flow restrictor 314 includes a locking member 328, a spring 330 and a peg 332 that is attached to housing 312. Locking member 328 includes an occluding portion 334 and an actuating portion 336. As mentioned above, flow restrictor 314 is so constructed and arranged to align with actuation member 304 of pumping device 302. Specifically, actuating portion 46 of flow restrictor 314 is so constructed and arranged to be contacted by actuation member 304 to rotate flow restrictor 314. Although shown as substantially rectangular in shape, actuation member 304 may have any shape or size that is sufficient to contact and rotate flow restrictor 314. For example, actuation member 304 may have a shape that is square, rectangular, triangular, oblong, parabolic, etc. Likewise, it will also be understood that actuating portion 336 of flow restrictor 314 may have any shape or size that is sufficient to be contacted and rotated by actuation member 304. For example, actuating portion 336 may have a shape that is square, rectangular, triangular, oblong, parabolic, etc. Further, the skilled artisan will also appreciate that occluding portion 334 of flow restrictor 314 may have any shape or size that is sufficient to occlude flexible tube 318 by pressing flexible tube 318 against stopper 316. For example, actuating portion 336 may have a shape that is square, rectangular, triangular, oblong, parabolic, etc.

During operation, when cassette 306 is inserted into pumping device 302, actuation member 304 will contact actuating portion 336 of locking member 328. Upon continued insertion into pumping device 302, actuation member 304 will actuate flow restrictor 314. In an embodiment, actuation member 304 actuates flow restrictor 314 by pushing actuating portion 336 of locking member 328 in a direction that is away from pumping device 302 to rotate locking member 328 counter-clockwise. Locking member 328 and spring 330 rotate about a common axis of rotation that is shared with peg 332. The skilled artisan will appreciate that locking member 328 need not rotate counter-clockwise. Rather, in another embodiment, locking member 328 may rotate clockwise.

In an embodiment where flow restrictor 314 is actuated by rotation, flow restrictor 314 rotates from a first, or resting position, as shown in FIGS. 44 and 46, to a second, or actuated position (not shown) as cassette 306 is inserted into pumping device 302. In the first, or resting position, flow restrictor 314 is located proximate stopper 316. By "located proximate stopper 316," it is understood that at least a portion of flow restrictor 314 is positioned close enough to stopper 316 to prevent fluid from flowing through flexible tube 318. Accordingly, when flow restrictor 314 is in a first or resting position and spring 330 is in a corresponding biased position, an occluding portion 334 of locking member 328 may press flexible tube 318 against stopper 316 so as to occlude flexible tube 318 and prevent fluid flow therethrough. Cassette 306 may be in the first, or resting position prior to insertion of cassette 306 into pumping device 302, and after cassette 306 is removed from pumping device 302.

As previously discussed, as cassette 306 is inserted into pumping device 302, actuation member 304 contacts actuating portion 336 of locking member 328. Upon continued insertion into pumping device 302, actuation member 304 will continue to act upon actuating portion 336 of locking member 328 to rotate locking member 328 to a second, actuated position (not shown), thereby applying tension to spring 330 and moving occluding portion 334 of locking member 328 away from stopper 316 such that flow restrictor 314 is located away from stopper 316. By "located away from stopper 316," it is understood that flow restrictor 314 is positioned sufficiently far enough away from stopper 316 to allow fluid to flow through flexible tube 318. Accordingly, when flow restrictor 314 is in an actuated position, occluding portion 334 of locking member 328 does not occlude flexible tube 318 against stopper 316 and, therefore, allows fluid to flow therethrough.

When cassette 306 is fully inserted into pumping device 302, actuation member 304 remains in contact with actuating portion 336 of locking member 328 to allow fluid to flow through flexible tube 318 during the time that cassette 306 resides in pumping device 302. As cassette 306 is removed from pumping device 302, actuation member 304 loses contact with actuating portion 336 of locking member 328 allowing the tension on spring 330 to relax. As the tension on spring 330 relaxes, spring 330 and locking member 328 are allowed to return to the first, or resting, position. In an embodiment, the locking member 328 and spring 330 relax and rotate clockwise until actuating portion 336 of locking member 328 contacts stopper 316, which prevents further clockwise rotation of locking member 330. Accordingly, when cassette 306 is removed from pumping device 302, flow restrictor 314 moves to the first, relaxed position, which occludes flexible tube 318.

As a result, flow restrictor 314 can be unlocked and deactivated by pumping device 302 when cassette 306 is inserted in pumping device 302 and reactivated when it is removed from pumping device 302. Unlike conventional anti-free flow devices in existing enteral feeding tube sets, cassette 306 is not deactivated by closing a door, by pressure, or a roller clamp. Instead, it will be deactivated by physically rotating flow restrictor 314 via a feature in pumping device 302.

In sum, the flow restriction mechanism of cassette 306 can be activated by a bias on spring 330 and deactivated via application of tension to spring 330 by rotating locking member 328. The locking member 328, which works in conjunction with the bias of spring 330, will seal the flow path thereby preventing flow through flexible tube 318. This flow restriction mechanism prevents any static pressure loss during pumping. When cassette 306 is inside pumping device 302, the flow can be prevented/controlled by pump rollers (e.g., peristaltic pumps) within pumping device 302.

As previously discussed, the use of enteral feeding pumps, in conjunction with an enteral feeding tube set as part of an enteral feeding system, for the administering of medical fluids is also well known in the medical arts. The enteral feeding tube set will typically include several long sections of tubing, connected to a centralized, shorter section of tubing that can be incorporated into a pumping device. One common concern with the enteral feeding tube set is that it is undesirable for large quantities of air to be provided with the enteral feeding solution. In enteral systems, excessive air may irritate the digestive system of the patient and complicate other medical conditions.

Any air within the enteral feeding tube set can also render the volumetric calculations of the enteral feeding pump inaccurate. Having an unknown quantity of air passing through the tube set causes the enteral feeding system to be unable to accurately determine the actual amount of solution that has been delivered to the patient. As a result, over a period of time, the excessive amounts of air passing through the enteral feeding system can cause significant differences in the amount of enteral feeding solution the system indicates to be delivered and the actual amount delivered to the patient.

In yet another embodiment, the present disclosure relates to air bubble sensor systems and methods of using the air bubble sensor systems. The air bubble sensor systems utilize infra-red technology and can be incorporated in pumping devices. The pumping device can be part of an enteral administration device or system that administers nutritional compositions to a person or patient in need of same.

A disease or condition specific nutritional composition is a composition that delivers nutrients or pharmaceuticals and can be a complete or partial nutritional composition. Disease or condition specific nutritional compositions are those designed to aid with a given situation, such as Impact® sold by Nestlé Nutrition to decrease post-operative infections, Diabetisource AC® sold by Nestlé Nutrition for people with diabetes or hyperglycemia, and Novasource® Pulmonary sold by Nestlé Nutrition for those patients with pulmonary disease or those requiring ventilator support.

Figure 48:
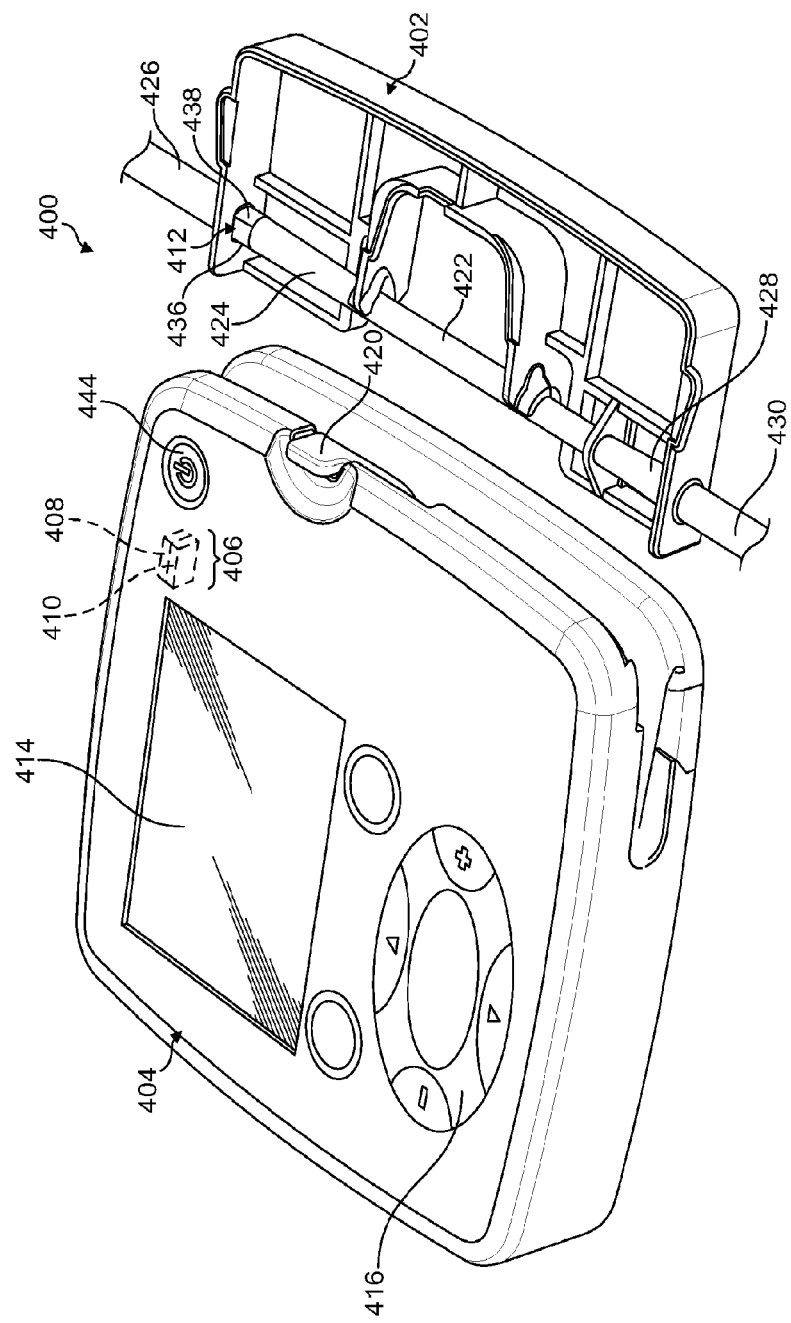
FIG. 48 shows a pumping device and cassette having a sensor system according to an embodiment of the present disclosure.
Figure 49:
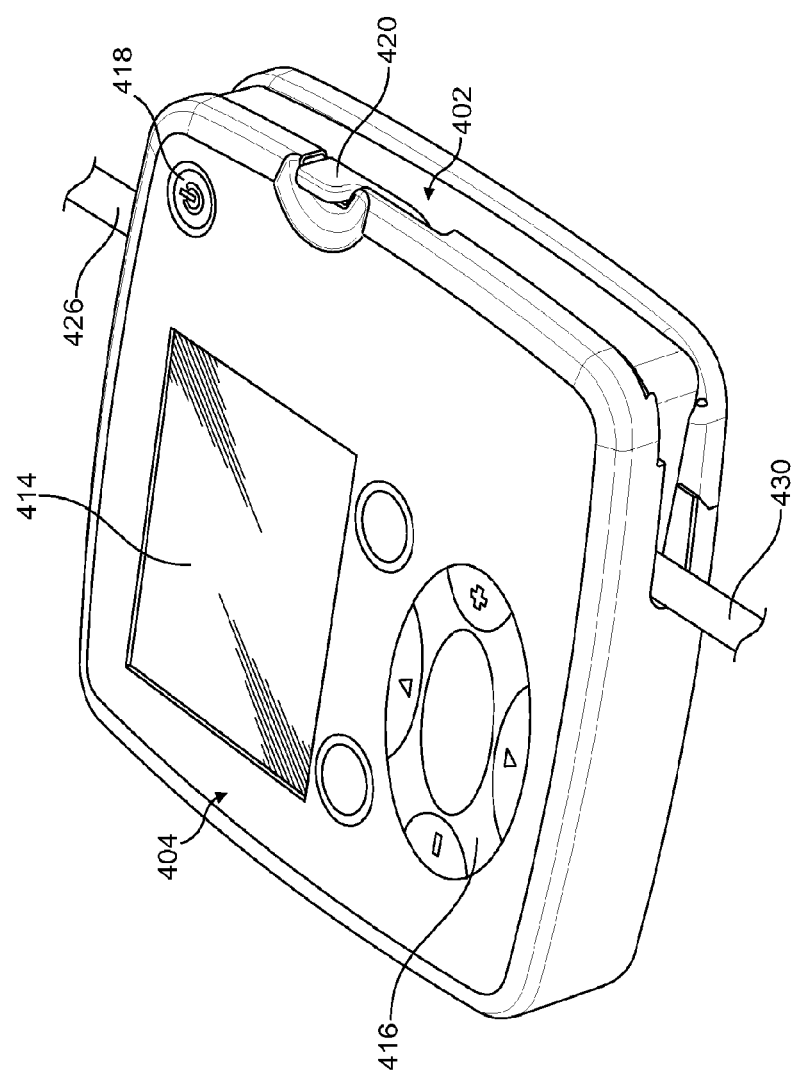
FIG. 49 shows the pumping device and the cassette of FIG. 48 with the cassette inserted into the pumping device according to an embodiment of the present disclosure.

As illustrated in FIGS. 48-49, in an embodiment, the present disclosure provides an air bubble sensor system 400 including a cassette 402 removably attachable to a pumping device 404. Pumping device 404 can include an infra-red sensor system 406 having an infra-red reflective light emitting diode 408 and an infra-red phototransistor receiver 410 positioned as part of the air bubble sensor system within an inner section of pumping device 404. Infra-red light emitter 408 can be a light emitting diode.

Figure 50:
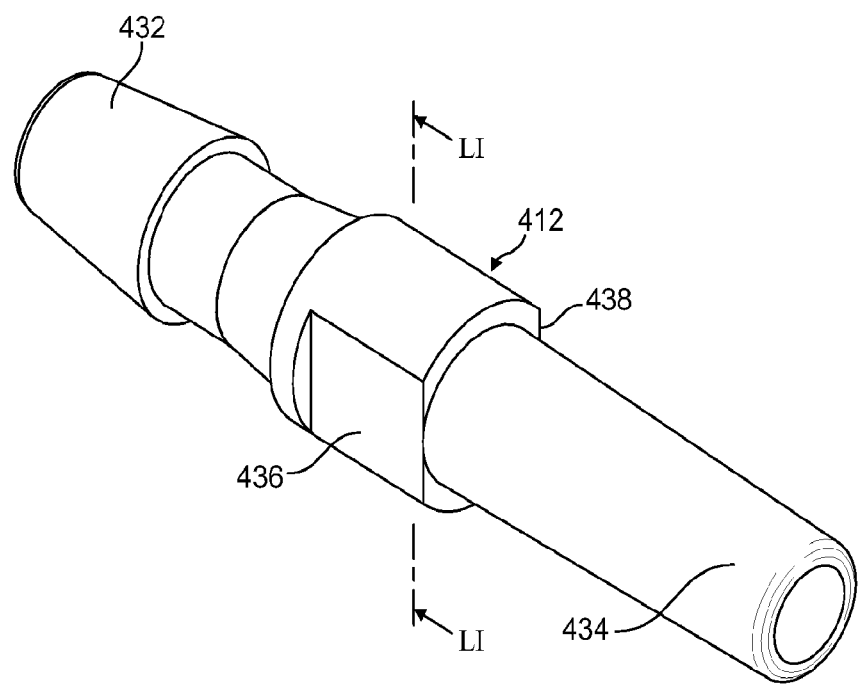
FIG. 50 shows a detection chamber according to an embodiment of the present disclosure.

Cassette 402 further includes a detection chamber 412 as part of the air bubble sensor system. Details of detection chamber 412 are shown in FIG. 50. Infra-red reflective light emitting diode 408 and infra-red phototransistor receiver 410 can be positioned to lay side-by-side and perpendicular to the length of detection chamber 412 as illustrated in FIG. 48.

Pumping device 404 can be an enteral feeding pump. Non-limiting examples of pumping devices are described in U.S. Pat. No. 6,659,976, which is incorporated herein by reference. Pumping device 404 can include a monitor/information screen 414 and a control pad 416 for operating pumping device 404. Monitor/information screen 414 and control pad 416 can also be used in conjunction with the air bubble sensor system in embodiments of the present disclosure. Pumping device 404 can further include a power button 418 and a release mechanism 420 for releasing cassette 402 from pumping device 404.

Cassette 402 can include a housing or support structure having any suitable shape such as the one shown in FIG. 48. Cassette 402 can be designed to be inserted partially or wholly within pumping device 404 as seen in FIG. 49. The design of cassette 402 can help in loading an enteral feeding tube set into pumping device 404 without having to route/guide the tubes or stretch the tubes from the tube set over a rotor (e.g., part of a peristaltic pump) contained within pumping device 404. Non-limiting examples of alternative cassette configurations are described in U.S. Pat. Nos. D504,506, D505,199, D455,489, D501,924 and D507,647, which are incorporated herein by reference. Cassette 402 can be made from any suitable rigid, semi-rigid or flexible material. Cassette 402 can also be designed such that it can be inserted into pumping device 404 only one way.

As seen in FIG. 48, cassette 402 includes a tube 422 attached to detection chamber 412 at a first end 424. Tube 422 can be flexible and have portions that are rigid or semi-rigid. Tube 422 can be a feeding tube and be constructed and arranged to be incorporated with the rotors of a pump (e.g., peristaltic pump) in pumping device 404.

Detection chamber 412 can be attached to a tube 426 leading away from cassette 402. Tube 422 can further include a second end 428 attached to a tube 430 leading away from cassette 402. As a result, fluid can flow through tube 422 in the direction from first end 424 to second end 428. Tube 426 can be connected to a nutritional composition source. Tube 430 can be connected to the person receiving the nutrition composition.

Figure 51:
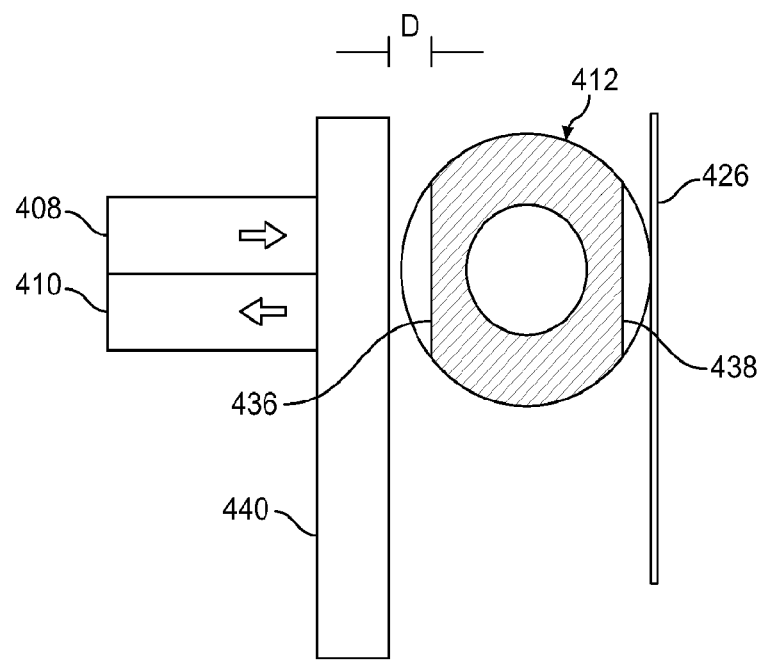
FIG. 51 shows an infra-red reflective sensor using the detection chamber of FIG. 50 according to an embodiment of the present disclosure.

As illustrated in FIGS. 50-51, detection chamber 412 can have an elongated body including a first end 432 configured to be removably attachable to tube 426 and a second end 434 configured to be removably attachable to first end 424 of tube 422. It should be appreciated that detection chamber 412 can also be integrally attached (e.g., as a single piece) with tube 422 and/or tube 426.

Detection chamber 412 can further include a window 436 to allow infra-red light or energy from infra-red reflective sensor 406 to pass through. Window 436 can be made from any suitable optically clear material that allows infra-red light from infra-red reflective sensor 406 to pass. From their position in pumping device 404 (see, FIG. 48), infra-red light emitter 408 and infra-red phototransistor receiver 410 are positioned at or near window 436 when cassette 402 is inserted into detection chamber 404. In an embodiment, infra-red reflective light emitting diode 408 and infra-red phototransistor receiver 410 can be in a stacked position along the height of detection chamber 412 as illustrated in FIG. 51.

Detection chamber 412 can be made from a molded, plastic chamber constructed and arranged to hold a tube on each end. For example, detection chamber 412 can be made from a transparent polyvinyl chloride material. In addition to window 436, any portion of detection chamber 412 can include an infra-red transparent surface or a solid surface to prevent transmission of infra-red light.

In an embodiment, an infra-red reflective surface 426 can be positioned behind window 436 to reflect infra-red light back to be detected by infra-red phototransistor receiver 410. Infra-red reflective surface 426 can be any suitable reflective surface such as a white paper or metallic surface. Infra-red reflective surface 426 can be incorporated as part of detection chamber 412. Alternatively, infra-red reflective surface 426 can be incorporated as part of cassette 402 at a location behind window 436 or an inner section of pumping device 404 at a location behind window 436 when cassette 402 is inserted into pumping device 404.

In an alternative embodiment, detection chamber 412 includes a second window 438 that assists in reflecting infra-red light back to the infra-red reflective sensor. Although window 438 is shown parallel to window 436 in FIG. 51, window 438 can be varied at any suitable angle to optimize the reflection of the infra-red light.

During operation, a nutritional composition passes through detection chamber 412 and through tube 422 to be administered to a person. Infra-red light emitter 408 emits an infra-red light that passes through window 436 and through the nutritional composition where it reflects off infra-red reflective surface 426. The strength of the reflected infra-red light can be monitored using infra-red phototransistor receiver 410. If there are changes to the strength of the infra-red signal, this can indicate that a discrepancy such as air bubbles appears within the nutritional composition. The strength of the reflected infra-red light or energy can vary depending on the contents of the nutritional composition and can be properly calibrated in view of same.

In another embodiment, detection chamber 412 can include an infra-red blocking material (not shown) to prevent the infra-red light from entering the chamber at an angle which interferes with the reflection signal. The infra-red blocking material can be any suitable material such as a black tape or a solid surface that prevents the transmission of infra-red light. The infra-red blocking material can be incorporated as part of detection chamber 412 at any suitable location.

Infra-red sensor system 406 can be any suitable infra-red sensor system having an infra-red emitting and detection device. Non-limiting examples of infra-red sensor system 406 include infra-red sensors developed under the QRD series by Fairchild Semiconductor. Infra-red light emitter 408 and infra-red phototransistor receiver 410 can be supported or positioned on a support 440 (e.g., within pumping device 404). If support 440 is used, it should be made of a suitable optically clear material that allows infra-red light to pass (e.g., polycarbonate).

Infra-red light emitter 408 and infra-red phototransistor receiver 410 can be positioned in a suitable manner with respect to window 436 of detection chamber 412 and with respect to each other so that a desired amount of the infra-red light sent out by infra-red light emitter 408 and reflected in detection chamber 412 is detected by infra-red phototransistor receiver 410. Infra-red light emitter 408 and infra-red phototransistor receiver 410 can be placed next to detection chamber 412 in contact with window 436 or spaced apart a suitable distance ("D") from window 436 to optimize the infra-red light emission and detection. Infra-red light emitter 408 and infra-red phototransistor receiver 410 can be placed side-by-side in contact with each other or spaced apart.

In an alternative embodiment, the present disclosure provides a cassette that incorporates an infra-red reflective sensor including an infra-red light emitter and an infra-red phototransistor receiver. In this regard, the pumping device does not house the infra-red reflective sensor. However, the infra-red reflective sensor on the cassette can be constructed and arranged to interact with the pumping device so that the results of the infra-red reflective sensor can be displayed on a monitor of the pumping device.

In yet another embodiment, the present disclosure provides a method of detecting air bubbles in a tubing for an enteral feeding system. The method includes providing an air bubble sensing system including 1) a detection chamber constructed and arranged for attaching to a feeding tube, 2) an infra-red reflective sensor including an infra-red light emitting diode, and 3) an infra-red phototransistor receiver, the infra-red reflective sensor and the infra-red phototransistor receiver positioned at or near the detection chamber. The detection chamber and the feeding tube can be incorporated as part of a cassette that can be attached to a pumping device.

The method further includes attaching the detection chamber to a feeding tube, and detecting an air bubble within the detection chamber by transmitting an infra-red light into the detecting chamber and detecting reflected infra-red light using the infra-red phototransistor receiver. If air bubbles are detected in the detection chamber, the pumping device can be stopped, for example, during an enteral feeding cycle.

Figure 52:
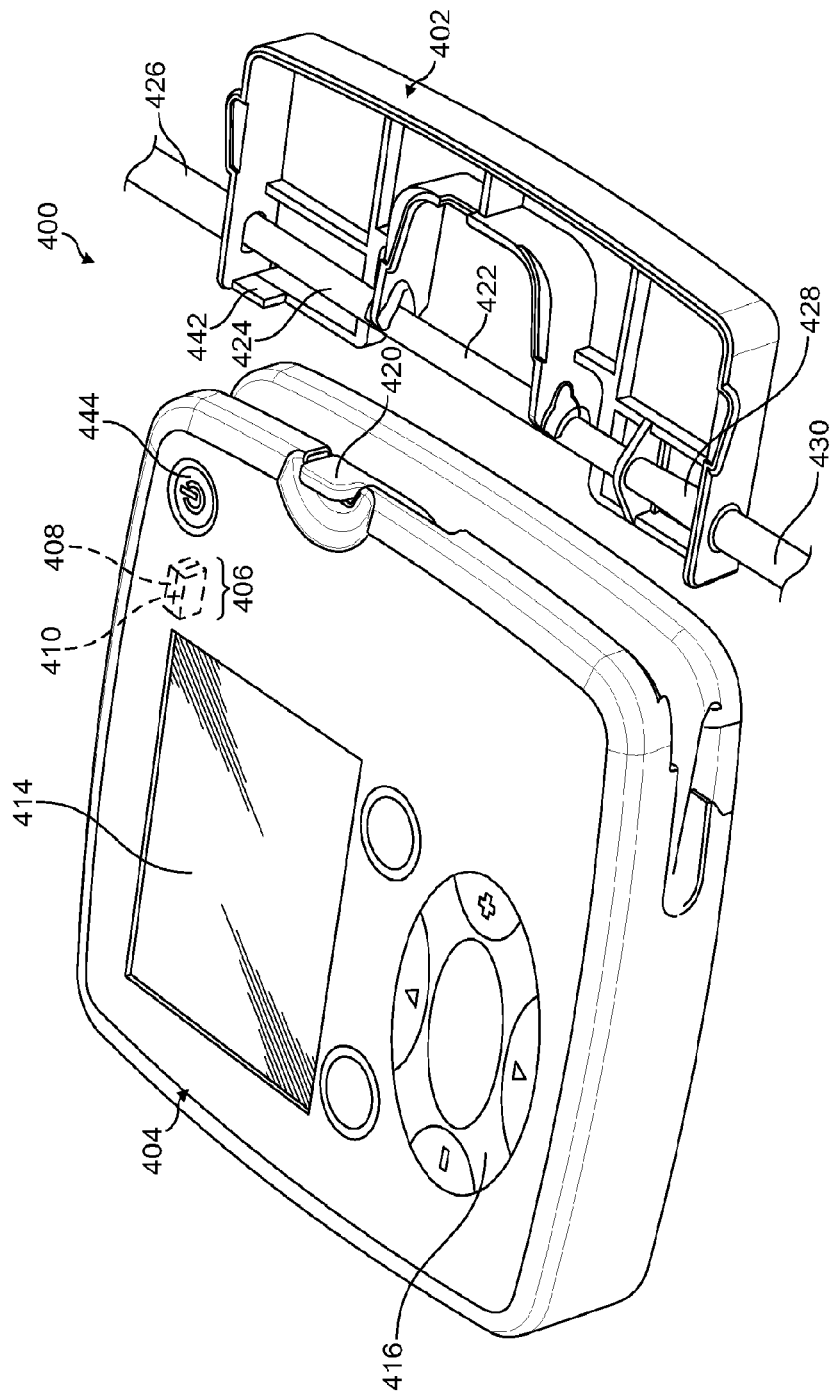
FIG. 52 shows a pumping device and cassette having a false reading component for an air-in-line sensor according to an embodiment of the present disclosure.

In an alternative embodiment, and as illustrated in FIG. 52, the present disclosure provides a cassette 402 having a component 442 that provides a false reading to infra-red sensor system 406. In other words, cassette 402 may include a component 442 that provides a consistent positive reading to infra-red sensor system 406 such that infra-red sensor system 406 will not detect any changes to the strength of an emitted infra-red signal.

For example, cassette 402 may be manufactured for use without detection chamber 412 having windows 436 or 438, and/or without infra-red reflective surface 426 being located on an opposite side of detection chamber 412 as infra-red system 406. In such an embodiment, cassette 402 may be manufactured to simply include cassette 402 with tubing 422 having first and second ends 424, 428. In such an embodiment, infra-red sensor system 406 cannot properly detect the strength of an emitted infra-red signal. Instead, infra-red sensor system 406 may read the failure to detect the strength of the emitted infra-red signal as an error and may prohibit pumping device 406 from delivering therapy to a patient.

To avoid such a situation, cassette 402 may be manufactured with component 442 to provide a false reading to infra-red sensor system 406. Such a component may include any component known in the art that will reflect a sufficient and consistent amount of an emitted infra-red signal back to the infra-red sensor system 406 such that infra-red sensor system 406 detects no change in the strength of the infra-red signal. The component may include, for example, an infra-red reflective surface such as white paper or a metallic surface, as discussed previously, or infra-red reflective plastics, glass, paint, tape, etc. Although component 442 is illustrated in FIG. 52 as a piece of infra-red reflective plastic, the skilled artisan will understand that any of the previously mentioned infra-red reflective materials, or any similar materials known in the art, may be used.

In an embodiment where cassette 402 is manufactured without infra-red sensor components such as, for example, detection chamber 412, false reading component 442 may be located on cassette 402 intermediate tubing 422 and infra-red sensor system 406. For example, in an embodiment, component 442 is an infra-red reflective piece of plastic formed integrally with cassette 402 and located intermediate tubing 422 and infra-red sensor system 406, as is shown in FIG. 52. Such a configuration will allow infra-red sensor system 406 to emit an infra-red signal using infra-red reflective light emitting diode 408, which may be reflected using false reading component 442, and which will be received by infra-red sensor system 406 using infra-red phototransistor receiver 410. According to such a configuration, infra-red sensor system 406 will continuously receive a positive and continuous infra-red signal regardless of the presence of air or other impurities in tubing 422.

As previously discussed, the use of enteral feeding pumps, in conjunction with an enteral feeding tube set as part of an enteral feeding system, for the administering of medical fluids is well known in the medical arts. The enteral feeding tube set will typically include several long sections of tubing, connected to a centralized, shorter section of tubing that can be incorporated into a pumping device. One common concern with the enteral feeding tube set is that it may become blocked or occluded over time without the patient's knowledge. If the feeding tube set does become occluded, the enteral feeding system may malfunction, and the patient will not receive the necessary nutrition, which could lead to adverse health problems for the patient.

In an embodiment, the present disclosure relates to occlusion sensor systems and methods of using the occlusion sensor systems. The occlusion sensor systems utilize infra-red technology and can be incorporated in pumping devices. The pumping device can be part of an enteral administration device or system that administers nutritional compositions to a person or patient in need of same.

Figure 53:
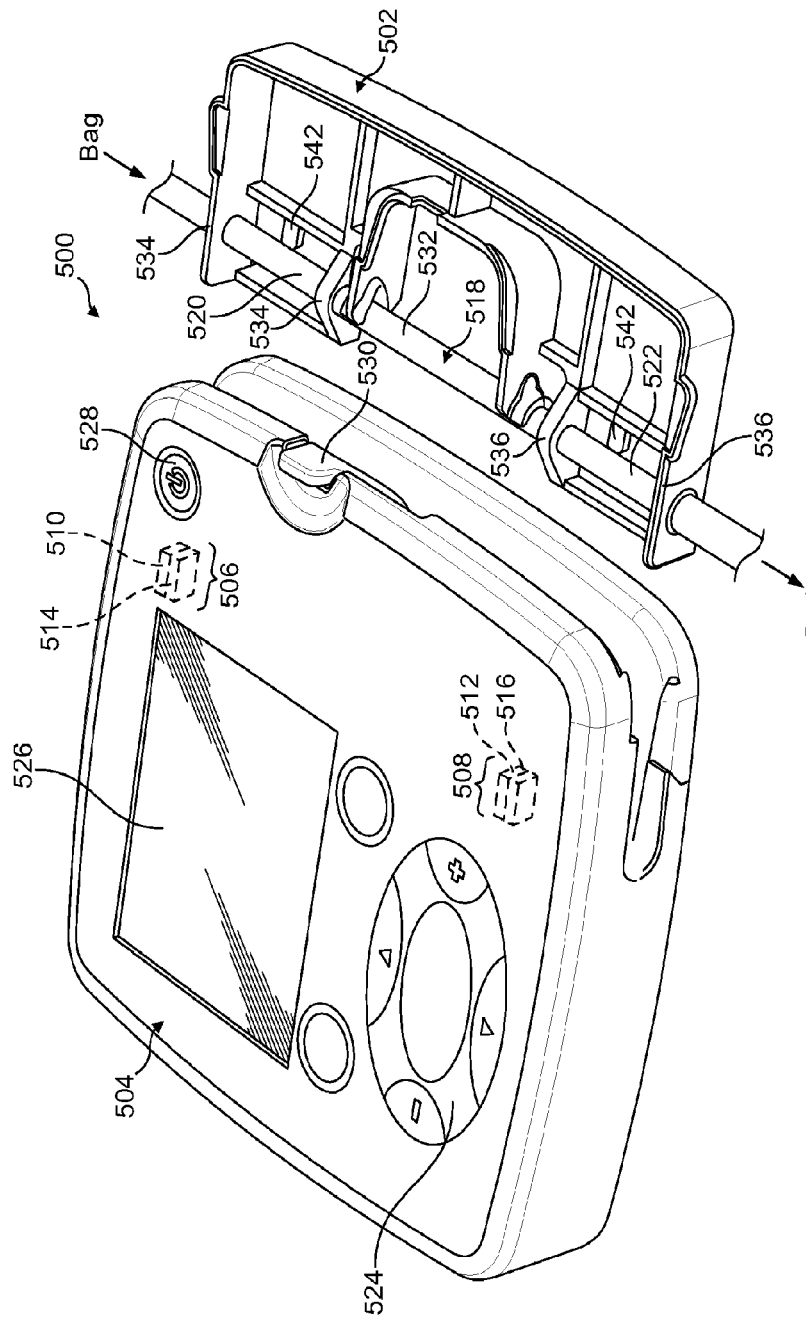
FIG. 53 shows a pumping device and cassette having an occlusion sensor system according to an embodiment of the present disclosure.
Figure 54:
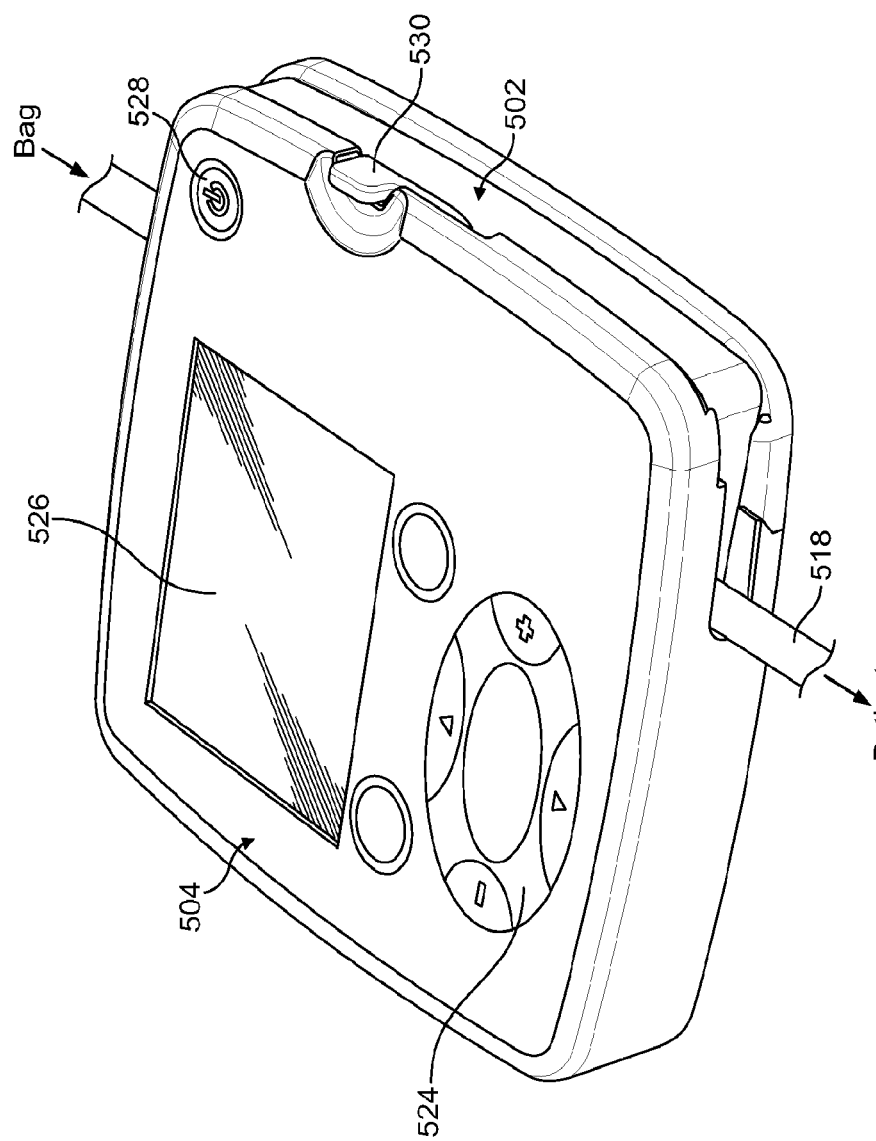
FIG. 54 shows the pumping device and the cassette of FIG. 53 with the cassette inserted into the pumping device according to an embodiment of the present disclosure.

As illustrated in FIGS. 53-54, in an embodiment, the present disclosure provides an occlusion sensor system 500 including a cassette 502 removably attachable to a pumping device 504. Pumping device 504 can include one or more infra-red sensors 506 and 508. Infra-red sensors 506 and 508 include infra-red reflective light emitters 510 and 512, respectively. Infra-red sensor 506 and 508 further include infra-red phototransistor receiver or photo-diodes 514 and 516, respectively, positioned as part of the occlusion sensor system 500 within an inner section of pumping device 504. Infra-red light emitters 510 and 512 can be a light emitting diode.

Infra-red sensors 506 and 508 can be any suitable infra-red sensor having an infra-red emitting device and a detection device. Non-limiting examples of infra-red sensors 506 and 508 include infra-red sensors developed under the QRD series by Fairchild Semiconductor. Infra-red light emitters 510 and 512 and infra-red phototransistor receiver or photo-diodes 514 and 516 can be supported or positioned on any suitable support (e.g., within pumping device 504).

Cassette 502 further includes tube 518 as part of the occlusion sensor system. When cassette 502 is inserted into pumping device 504, infra-red reflective light emitters 510 and 512 and infra-red phototransistor receiver or photo-diodes 514 and 516 can be positioned to lay side-by-side and along the length of tube 518 at different portions 520 and 522, respectively, of tube 518 as illustrated in FIG. 53.

Fluid can flow through tube 518 in the direction from first portion 520 to second portion 522. Tube 518 can extend from portion 520 to be connected to bag containing a nutritional composition source and can extend from portion 522 to be connected to the person receiving the nutrition composition.

Infra-red sensors 506 and 508 can be positioned on either side of a pump (not shown) within pumping device 504. For example, the pump can be located at a central location of pumping device 504 and would interact with a portion 532 of tube 518 located on cassette 502. Accordingly, infra-red sensor 506 interacts with portion 520 of tube 518 located upstream of the pump (e.g., receive a nutritional composition from a container or bag). Infra-red sensor 508 would interact with portion 522 of tube 518 located downstream of the pump (e.g., sending a nutritional composition to the patient).

Pumping device 504 can be an enteral feeding pump. The pump contained within pumping device 504 can be a peristaltic pump. Non-limiting examples of pumping devices are described in U.S. Pat. No. 6,659,976, which is incorporated herein by reference. Pumping device 504 can include a monitor/information screen 526 and a control pad 524 for operating pumping device 504. Monitor/information screen 526 and control pad 524 can also be used in conjunction with the occlusion sensor system in embodiments of the present disclosure. Pumping device 504 can further include a power button 528 and a release mechanism 530 for releasing cassette 502 from pumping device 504.

Cassette 502 can include a housing or support structure having any suitable shape such as the one shown in FIG. 53. Cassette 502 can be designed to be inserted partially or wholly within pumping device 504 as seen in FIG. 54. The design of cassette 502 can help in loading an enteral feeding tube set into pumping device 504 without having to route/guide the tubes or stretch the tubes from the tube set over a rotor (e.g., part of a peristaltic pump) contained within pumping device 504. Non-limiting examples of alternative cassette configurations are described in U.S. Pat. Nos. D504,506, D505,199, D455,489, D501,924 and D507,647, which are incorporated herein by reference. Cassette 502 can be made from any suitable rigid, semi-rigid or flexible material. Cassette 502 can also be designed such that it can be inserted into pumping device 504 only one way.

Tube 518 can be flexible and have portions that are rigid or semi-rigid. Tube 518 can be a feeding tube and be constructed and arranged to be incorporated with the rotors of a pump (e.g., peristaltic pump) in pumping device 504.

Figure 55:
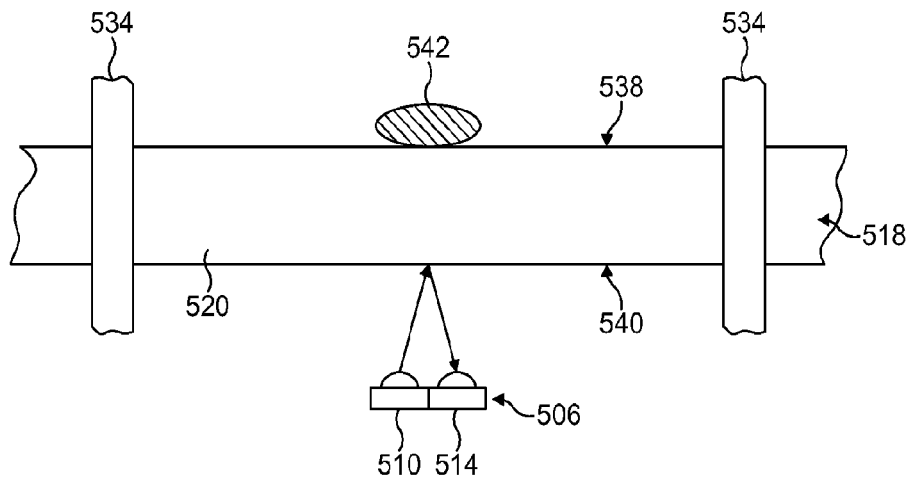
FIGS. 55-57 show the detection of an occlusion in a tube according to an embodiment of the present disclosure.
Figure 56:
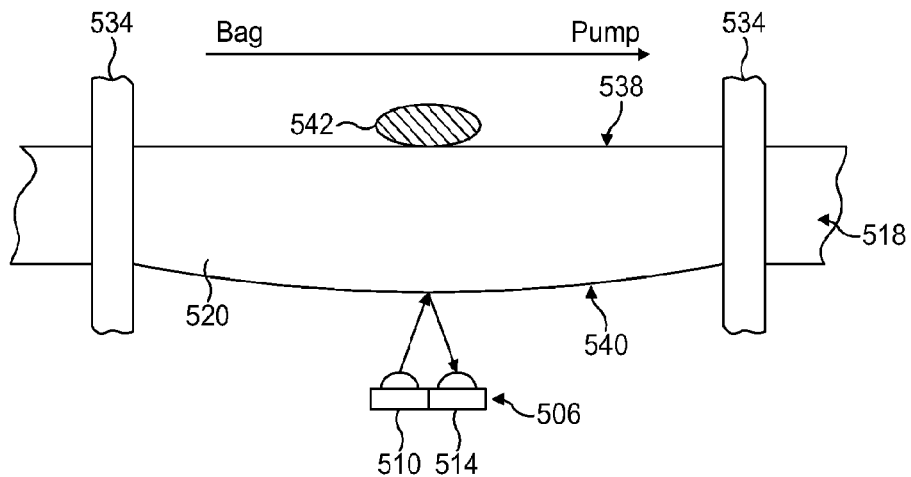
Figure 57:
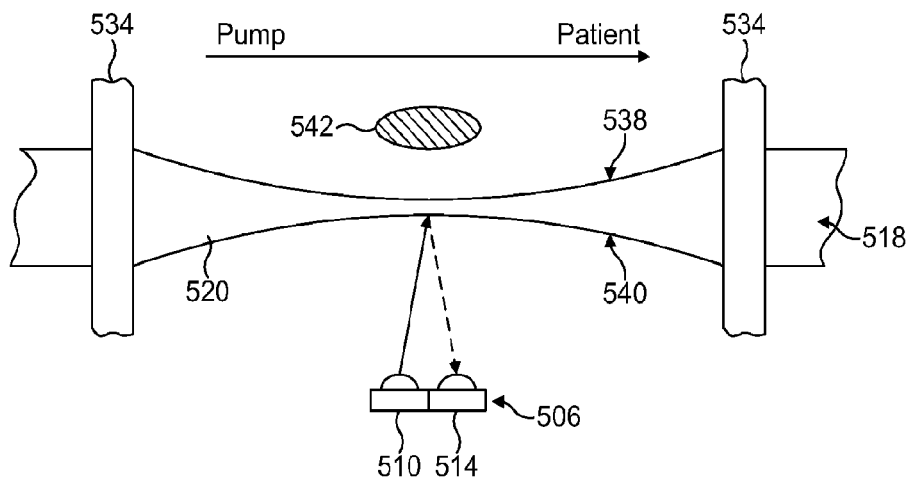

During operation as shown in FIGS. 55-57, a pump (not shown) within pumping device 504 located near portion 532 pumps the nutritional composition from a bag through cassette 502 via tube 518 to a patient. If there is no occlusion either between the bag and the pump or the pump and the patient, the sidewalls of tube 518 at portions 520 and 522 remain stationary (e.g., do not expand or contract). Portions 532 and 536 of the cassette 502 covering tube 518 on either side of portions 520 and 522, respectively, act as tube retention mechanisms that help retain tube 518 in position within cassette 502.

If an occlusion in tube 518 occurs upstream of the pump (e.g., between the bag and the pump), the pump will continue to attempt to pass the nutritional composition through tube 518. However, because no nutritional composition is passing through, the sidewalls 538 and 540 of portion 520 of tube 518 will begin to contract (e.g., move inward) as shown in FIG. 56. At the same time, infra-red light emitter 510 will emit infra-red light toward sidewall 540 of tube 518 facing infra-red light emitter 510. Because sidewall 540 will be opaque or include an infra-red reflective material, sidewall 540 will reflect the infra-red light back to be detected by infra-red phototransistor receiver or photo-diode 514.

An intensity or amount of the reflected infra-red light will be proportional to the distance that sidewall 540 is from infra-red sensor 506. As a result, if the intensity of the reflected light changes because sidewall 540 is further away from infra-red sensor 506, this shows that sidewall 540 has contracted thereby signifying that the occlusion has occurred upstream of the pump. The intensity of the detected infra-red emitted light at various stages of contraction of sidewall 540 can be measured and calibrated so that the amount of contraction (e.g., related to the strength of the occlusion) can be determined using a computer processor, for example, on pumping device 504. It is understood that the change in direction is dependant upon the position of the tubing in relation to optimal focal point (maxima for photo detector current) of the sensor. If the initial spacing is less than the maxima point, then as the tubing shrinks the received reflected energy will increase. The inverse occurs when the tubing starts past the maxima point, the reflected energy will, in that case, decrease as the tubing contracts. Either mode can be useful but the selection can be a function of the mechanical constraints imposed in integrating the sensor as part of the larger system.

If an occlusion in tube 518 occurs downstream of the pump (e.g., between the pump and the patient), the pump will continue to attempt to pass the nutritional composition through tube 518. However, because the accumulating nutritional composition is building pressure up in tube 518 by passing through, the sidewalls 538 and 540 of portion 522 of tube 518 will begin to expand or bulge (e.g., move outward). At the same time, infra-red light emitter 512 will emit infra-red light toward sidewall 540 of tube 518 facing infra-red light emitter 512.

An intensity or amount of the reflected infra-red light will be proportional to the distance that sidewall 540 is from infra-red sensor 508. As a result, if the intensity of the reflected light changes because sidewall 540 is closer to infra-red sensor 508, this shows that sidewall 540 has expanded thereby signifying that the occlusion has occurred downstream of the pump. The intensity of the detected infra-red emitted light at various stages of sidewall 540 can be measured and calibrated so that the amount of expansion (e.g., related to the strength of the occlusion) can be determined using a computer processor, for example, on pumping device 504.

As illustrated in FIGS. 53 and 55-57, cassette 502 can include a bias bump 542 that is adjacent to tube 518 at portions 520 and 522. Bias bump 542 can be used to prevent sidewall 538 of tube 518 located on the same side as bias bump 542 from expanding past bias bump 542. As a result, sidewall 540 of tube 518 opposite bias bump 542 can expand further toward infra-red sensors 506 and 508 than would be possible without bias bump 542. This can increase the sensitivity of the occlusion detection.

Figure 58:
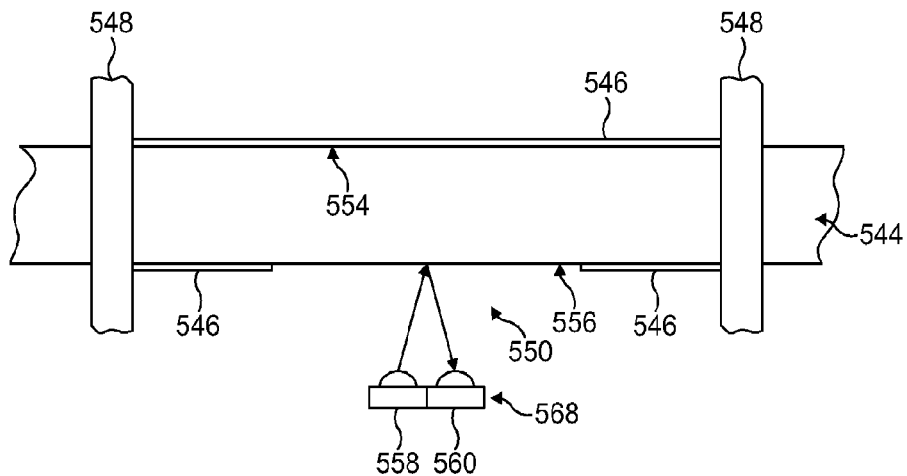
FIGS. 58-60 show the detection of an occlusion in a tube according to an embodiment of the present disclosure.
Figure 59:
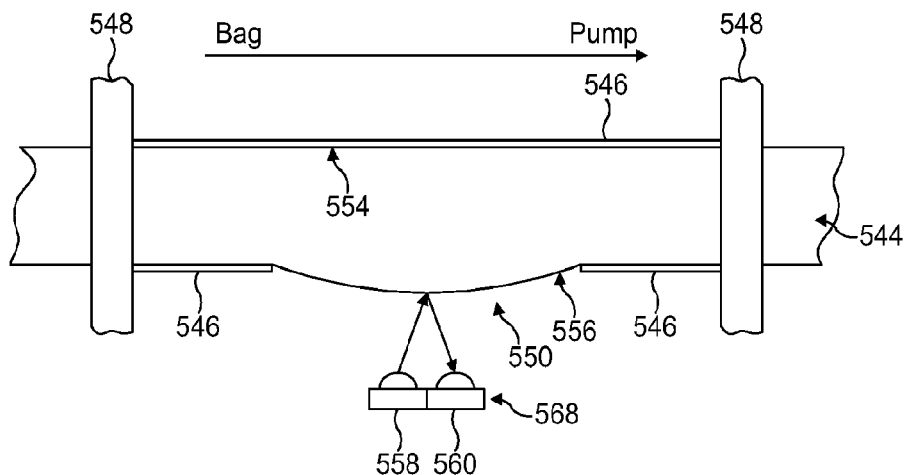
Figure 60:
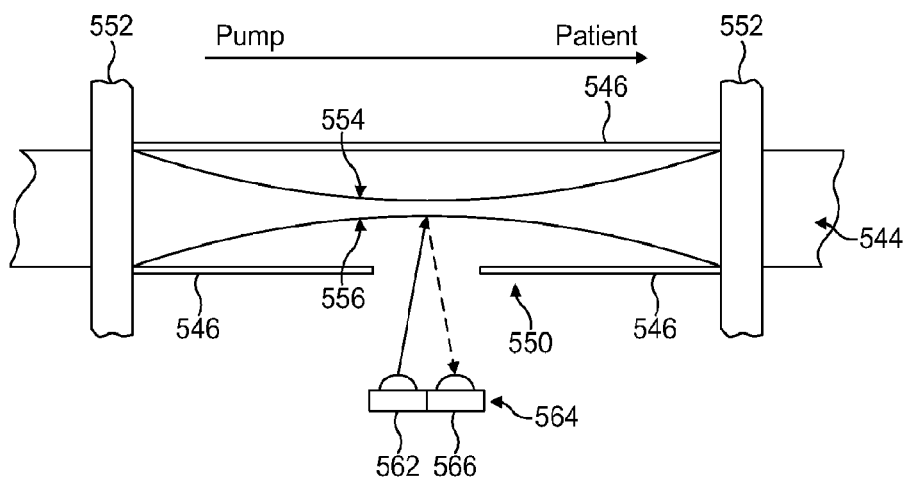

In another embodiment shown in FIGS. 58-60, a tube 544 can be positioned with a tube housing 546 that is integrated with a portion 548 of a cassette that holds tube 544. Tube housing 546 further defines a window 550. Tube housing 546 can be made, for example, from a molded, plastic chamber constructed and arranged to hold tube 544. For example, tube housing 546 can be made from an opaque polyvinyl chloride material. Any portion of tube housing 546 can include an infra-red transparent surface or a solid surface to prevent transmission of infra-red light or absorb infra-red light so that infra-red light only passes though window 550.

During operation as shown in FIGS. 58-60, a pump (not shown) pumps the nutritional composition from a bag through tube 544 to a patient. If there is no occlusion either between the bag and the pump or the pump and the patient, the sidewalls of tube 544 remain stationary (e.g., do not expand or contract). The portions 548 and 552 of the cassette covering tube 544 act as tube retention mechanisms that retain tube 544 in position with the cassette.

If an occlusion in tube 544 occurs upstream of the pump (e.g., between the bag and the pump), the pump will continue to attempt to pass the nutritional composition through tube 544. However, because no nutritional composition is passing through, the sidewalls 554 and 556 of tube 544 located upstream of the pump will begin to contract (e.g., move inward) as shown in FIG. 59. At the same time, infra-red light emitter 558 will emit infra-red light toward sidewall 556 of tube 544 through window 550 of tube housing 546. Because sidewall 556 will be opaque or include an infra-red reflective material, sidewall 556 will reflect the infra-red light back to be detected by an infra-red phototransistor receiver or photo-diode 560 of an infra-red sensor system 568. The intensity or amount of the reflected infra-red light is proportional to the distance that sidewall 556 is from infra-red sensor 568, and the change in intensity signifies that the occlusion has occurred upstream of the pump.

If an occlusion in tube 544 occurs downstream of the pump (e.g., between the pump and the patient), the pump will continue to attempt to pass the nutritional composition through tube 544. However, because the accumulating nutritional composition is building pressure up in tube 544 by passing through, the sidewalls 554 and 556 of tube 544 downstream of the pump will begin to expand or bulge (e.g., move outward) as shown in FIG. 60. At the same time, infra-red light emitter 562 of infra-red sensor 564 will emit infra-red light toward sidewall 556 of tube 544. The change in intensity of the reflected light increases measured by infra-red phototransistor receiver or photo-diode 566 shows that sidewall 556 has expanded thereby signifying that the occlusion has occurred downstream of the pump. Because of tube housing 546, only a portion of tube 544 located at window 550 will expand or pass through window 550 thereby providing a more concise expansion of tube 544.

Infra-red sensors 568 and 564 can be positioned in a suitable manner with respect to window 550 of tube housing 546 and with respect to each other so that a desired amount of the infra-red light sent out by infra-red sensors 568 and 564 and reflected off of tube 544 is detected by infra-red sensors 568 and 564. Infra-red light emitters 558 and 562 and infra-red phototransistor receiver or photo-diodes 560 and 566, respectively, can be placed side-by-side in contact with each other or spaced apart.

In an alternative embodiment, the present disclosure provides a cassette that incorporates an infra-red reflective sensor including an infra-red light emitter and an infra-red phototransistor receiver or photo-diode. In this regard, the pumping device does not house the infra-red reflective sensor. However, the infra-red reflective sensor on the cassette can be constructed and arranged to interact with the pumping device so that the results of the infra-red reflective sensor can be displayed on a monitor of the pumping device.

In yet another embodiment, the present disclosure provides a method of detecting occlusions in a tubing for an enteral feeding system. The method includes providing an occlusion sensing system including a feeding tube and an infra-red reflective sensor including an infra-red light emitting diode and an infra-red phototransistor receiver or photo-diode. The feeding tube can be incorporated as part of a cassette that can be attached to a pumping device of the enteral feeding system.

The method further includes detecting an occlusion within the feeding tube by transmitting an infra-red light toward the feeding tube and detecting reflected infra-red light using the infra-red phototransistor receiver or photo-diode, for example, based on an amount of the expanding or contracting of the feeding tube. If occlusions are detected in the feeding tube, the pumping device can be stopped, for example, during an enteral feeding cycle.

Figure 61:
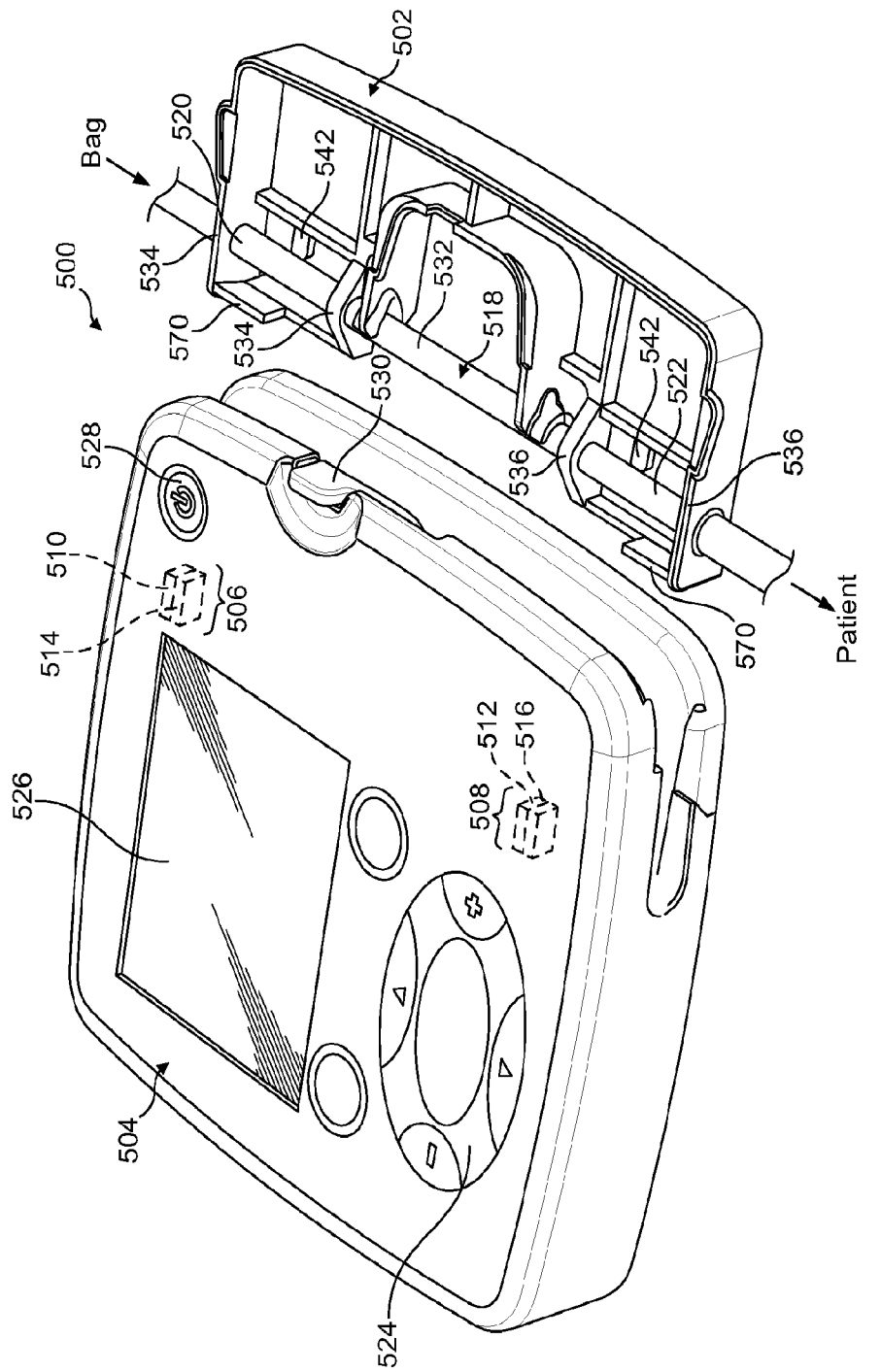
FIG. 61 shows a pumping device and cassette having a false reading component for an occlusion sensor according to an embodiment of the present disclosure.
Figure 62:
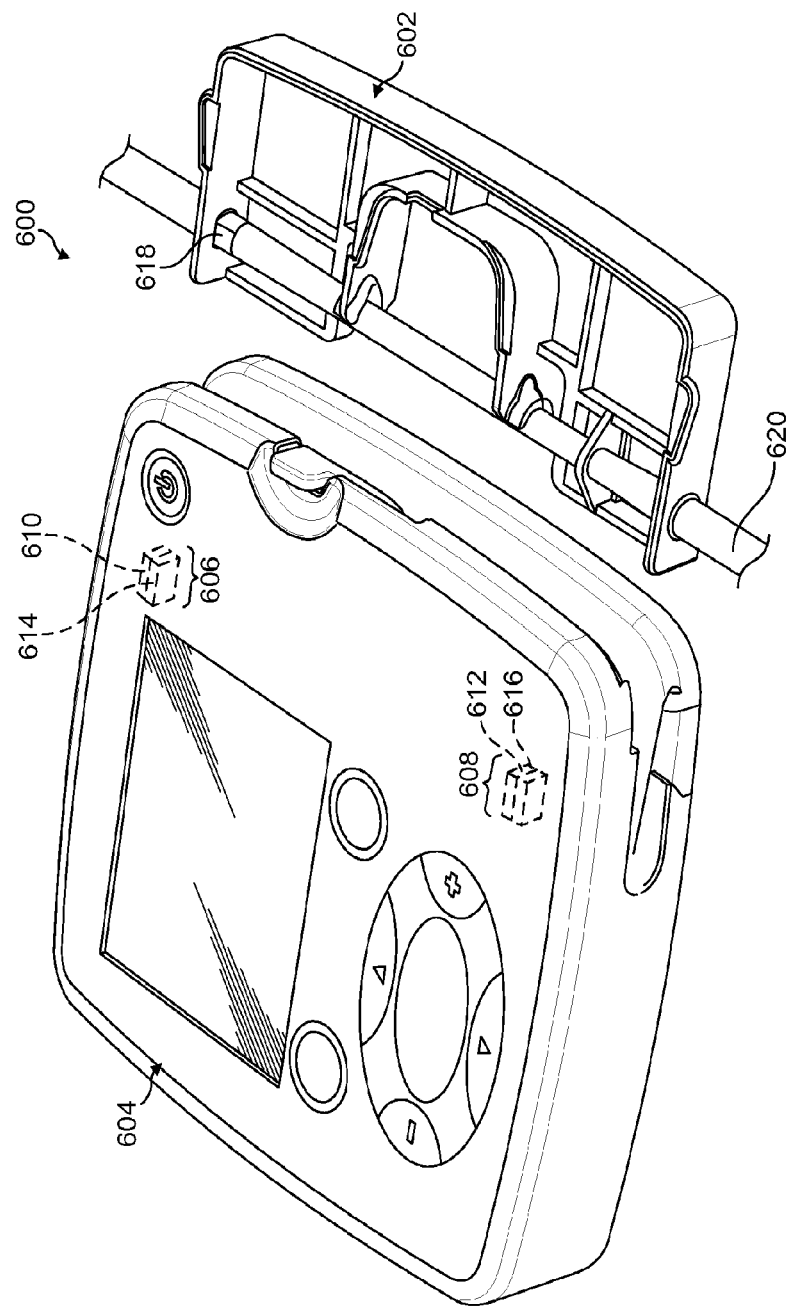
FIG. 62 shows a pumping device and cassette having both an air-in-line sensor device and an occlusion sensor device according to an embodiment of the present disclosure.

In an alternative embodiment, and as illustrated in FIG. 61, the present disclosure provides a cassette 502 having a component 570 that provides a false reading to infra-red sensors 506, 508. In other words, cassette 502 may include a component 570 that provides a consistent positive reading to infra-red sensors 506, 508 such that infra-red sensors 506, 508 will not detect any changes to the intensity of a reflected infra-red signal that is emitted from infra-red light emitters 510, 512, reflected by sidewall 540 of tubing 518 and detected by infra-red phototransistor receiver or photo-diode 514, 516.

For example, cassette 502 may be manufactured without bias bump 542, and without sidewall 540 of tubing 518 having an opaque or infra-red reflective surface. In such an embodiment, cassette 502 may be manufactured to simply include cassette 502 with tubing 518 having first and second portions 520, 522. In such an embodiment, infra-red sensors 506, 508 cannot properly detect the intensity of a reflected infra-red signal. Instead, infra-red sensors 506, 508 may read the failure to detect the intensity of the reflected infra-red signal as an error and may prohibit pumping device 504 from delivering therapy to a patient.

To avoid such a situation, cassette 502 may be manufactured with component 570 to provide a false reading to infra-red sensors 506, 508. Such a component may include any component known in the art that will reflect a sufficient and consistent amount of an emitted infra-red signal back to infra-red sensors 506, 508 such that infra-red sensors 506, 508 detect no change in the intensity of the reflected infra-red signal. The component may include, for example, an infra-red reflective surface such as white paper or a metallic surface, as discussed previously, or infra-red reflective plastics, glass, paint, tape, etc.

In an embodiment where cassette 502 is manufactured without infra-red sensor components such as, for example, bias bump 542 and sidewall 540 of tubing 518 having an opaque or infra-red reflective surface, false reading component 570 may be located on cassette 502 intermediate tubing 518 and infra-red sensors 506, 508. For example, in an embodiment, component 570 may be an infra-red reflective piece of plastic formed integrally with cassette 502 and located intermediate tubing 518 and infra-red sensors 506, 508. Such a configuration will allow infra-red sensors 506, 508 to emit an infra-red signal using infra-red light emitter 510, 512, which may be reflected using false reading component 570, and which will be received by infra-red sensors 506, 508 using infra-red phototransistor receiver or photo-diode 514, 516. According to such a configuration, infra-red sensors 506, 508 will continuously receive a positive and continuous infra-red signal regardless of the presence of an occlusion in tubing 518.

As discussed previously, any air within or occlusion of enteral feeding tubes can cause medical complications or adverse health problems for the patient receiving nutritional compositions via an enteral feeding system. Accordingly, cassettes may be provided that include air-in-line or occlusion sensors that are used to alert the patient or healthcare provider of a potential issue with the enteral feeding system. However, sometimes an air-in-line sensor or an occlusion sensor may not be sensitive enough to properly detect air and/or occlusions and, therefore, may not properly alert the patient or healthcare provider of potential adverse health concerns.

For example, for water-like feeds, an infra-red air-in-line sensor system provides a robust method of determining the feed to air to feed transitions that occur in the tubing of the cassette. For certain viscous feeds, however, a large amount of reside of material may remain in the air-in-line detection chamber after the transition to air. The remaining residue, therefore, prevents the timely detection of air in the detection chamber (e.g., an air-in-line condition). However, since an occlusion sensor also reacts to the absence or presence of feeds in the tubing in a manner entirely different from the air-in-line sensor, an occlusion sensor may be used to enhance the fluid to air detection process.

As discussed above, an occlusion sensor operates by measuring the infra-red light reflected from the tubing in the cassette, which may be, for example, a silicone tubing. The reflected infra-red energy is dependent upon the distance between the tubing and the sensor, as well as the type of feed in the tubing. An additional signal may also be observed from the occlusion sensor—a signal shift upon a feed to air or air to feed transition. The direction of the shift from the air state is dependent upon the type of feed. For example, for water and high water content feeds, which have lower infra-red reflectance, the transition from feed to air is a falling edge on a graph illustrating seconds on the x-axis and volts on a y-axis. In contrast, feeds that are more viscous and reflect infra-red signals stronger than air, the inverse is true. In other words, a more viscous feed with result with a transition from feed to air in a rising edge on a graph illustrating second on the x-axis and volts on a y-axis. The output signal from an inlet (proximal) occlusion sensor provides an advantageous point of observation since it is closest to the location of the air-in-line sensor.

Therefore, in yet another embodiment, the present disclosure provides an infra-red sensor system 600 including a cassette 602 having tubing 620, cassette 602 being removably attached to a pumping device 604. Pumping device 604 can include an air-in-line infra-red sensor system 606 and an occlusion infra-red sensor system 608. Each of the air-in-line infra-red sensor system 606 and the occlusion infra-red sensor system 608 are provided with an infra-red reflective light emitting diode 610, 612, and an infra-red phototransistor receiver 614, 616. Details of exemplary air-in-line infra-red sensor systems 606 and occlusion infra-red sensor system 608 are discussed above with respect to FIGS. 48-52 and 53-61, respectively.

Depending on the content of nutritional compositions, viscosities and residues of nutritional compositions can vary greatly. For example, FIGS. 63-66 illustrate exemplary feed to air transitions as measured by an air-in-line infra-red sensor 606 and an occlusion infra-red sensor 608 for different viscosity nutritional compositions. In each of the FIGS., the occlusion sensor data has been scaled up by a factor of two for clarity. The time differences in the FIGS. between the rising edges of the air-in-line infra-red sensor data and the occlusion infra-red sensor data is caused by the large physical distance between the sensor in the test bed.

Figure 63:
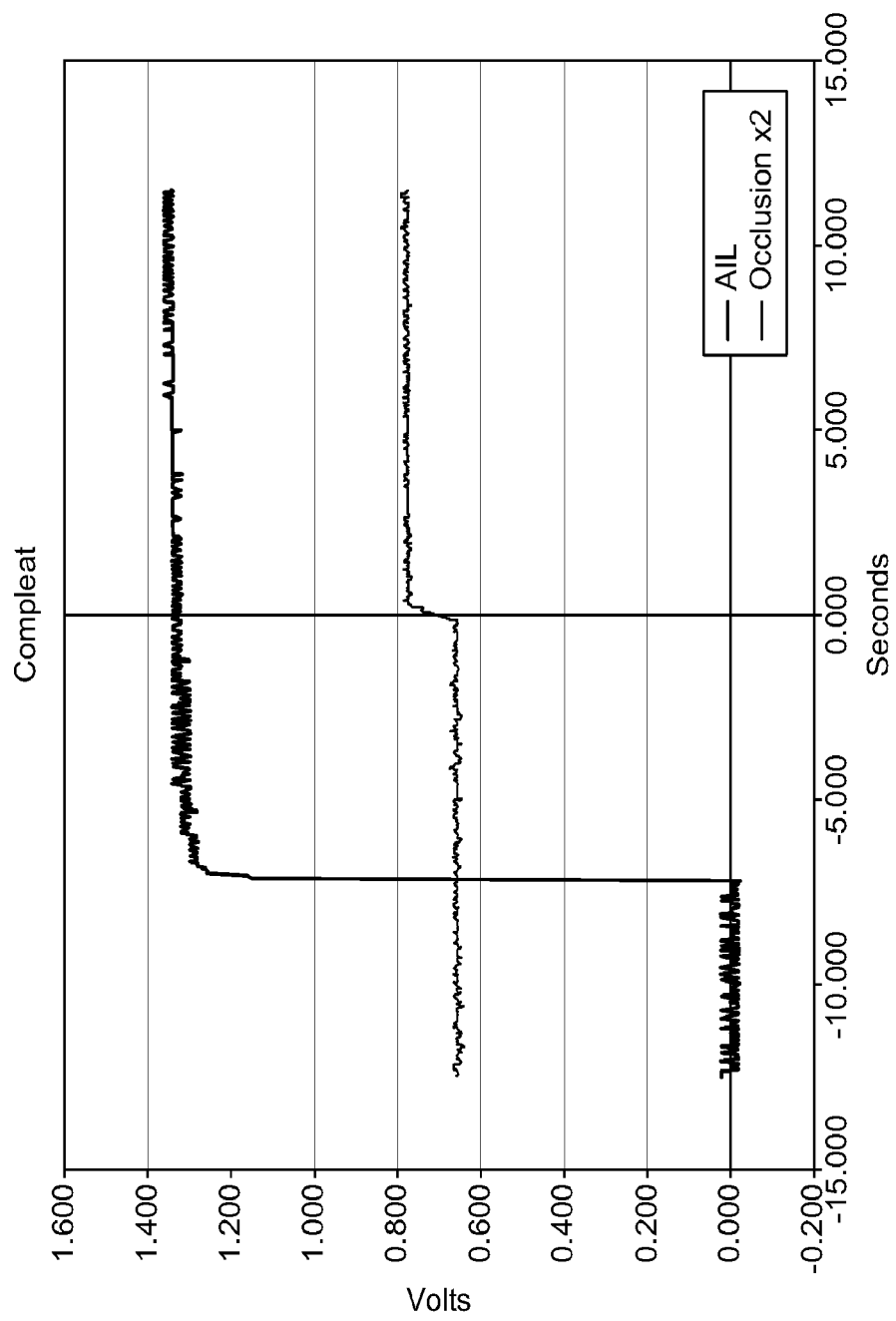
FIG. 63 shows a graph indicating feed to air transitions for a non-viscous, low residue feed as measured by an air-in-line sensor and an occlusion sensor according to an embodiment of the present disclosure.

As shown by FIG. 63, an air-in-line infra-red sensor 606 was able to provide a reliable indication of a transition from feed to air for the nutritional composition, COMPLEAT®, which is a nutritional composition manufactured by Nestlé Nutrition. COMPLEAT® is formulated with real foods including, for example, chicken, peas, carrots, tomatoes and cranberry juice cocktail, as well as a fiber blend. Accordingly, COMPLEAT® is a non-viscous, low residue feed.

Figure 64:
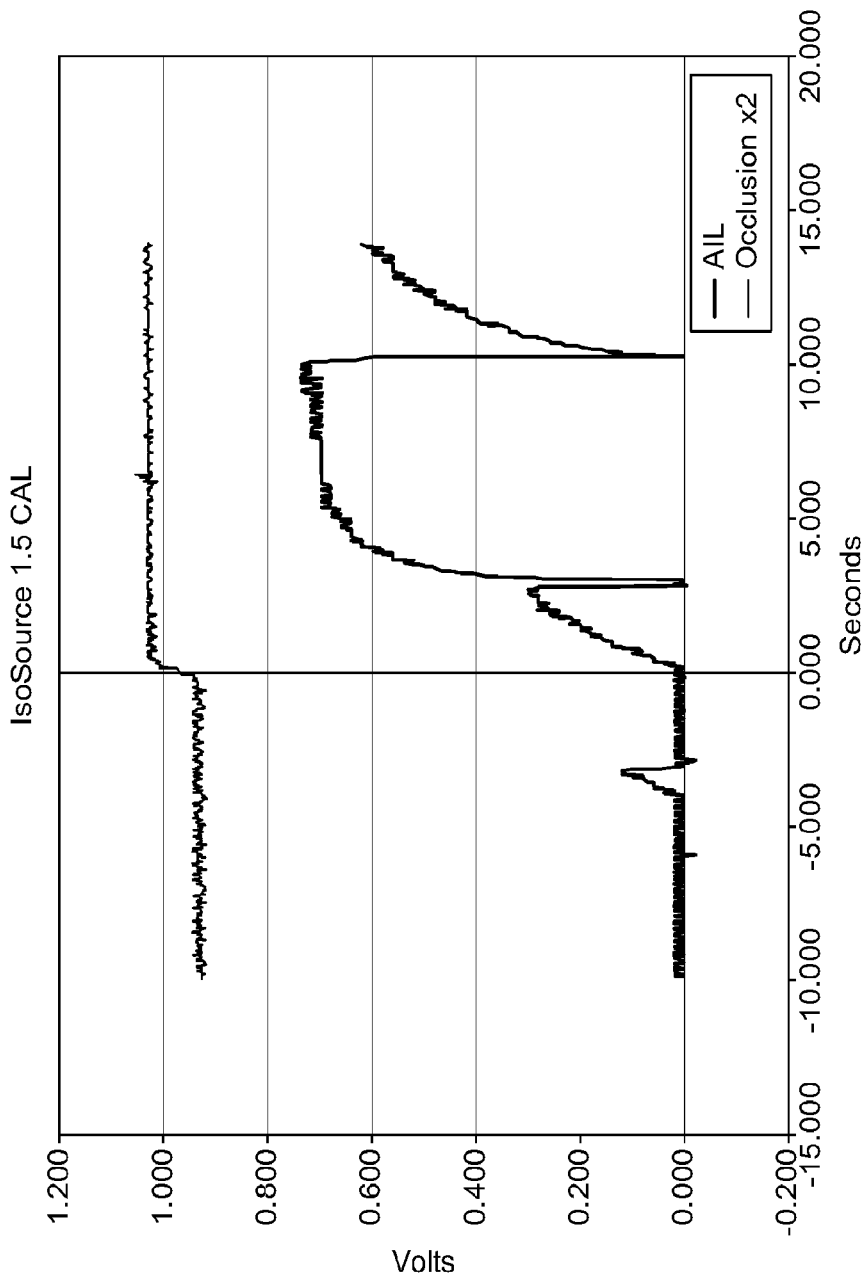
FIG. 64 shows a graph indicating feed to air transitions for a viscous, higher residue feed as measured by an air-in-line sensor and an occlusion sensor according to an embodiment of the present disclosure.

In contrast, the graph in FIG. 64 illustrates that an air-in-line sensor 606 cannot properly detect the transition from feed to air for a nutritional composition such as ISOSOURCE® 1.5 CAL, also manufactured by Nestlé Nutrition. In contrast to the non-viscous, low residue feed of FIG. 63, ISOSOURCE® 1.5 CAL is more viscous and, therefore, has a greater amount of residue. As is shown in FIG. 64, the late changes in the air-in-line sensor 606 reading are due to the residue gradually flowing off the air-in-line detection chamber 618 walls while pumping device 604 continues to run, and as small slugs of residual feed move from a feed reservoir (not shown), past the air-in-line sensor 606 and gradually carry away the residue. In contrast to the air-in-line sensor 606, the occlusion sensor 608 provides a clear indication of the feed to air transition.

Figure 65:
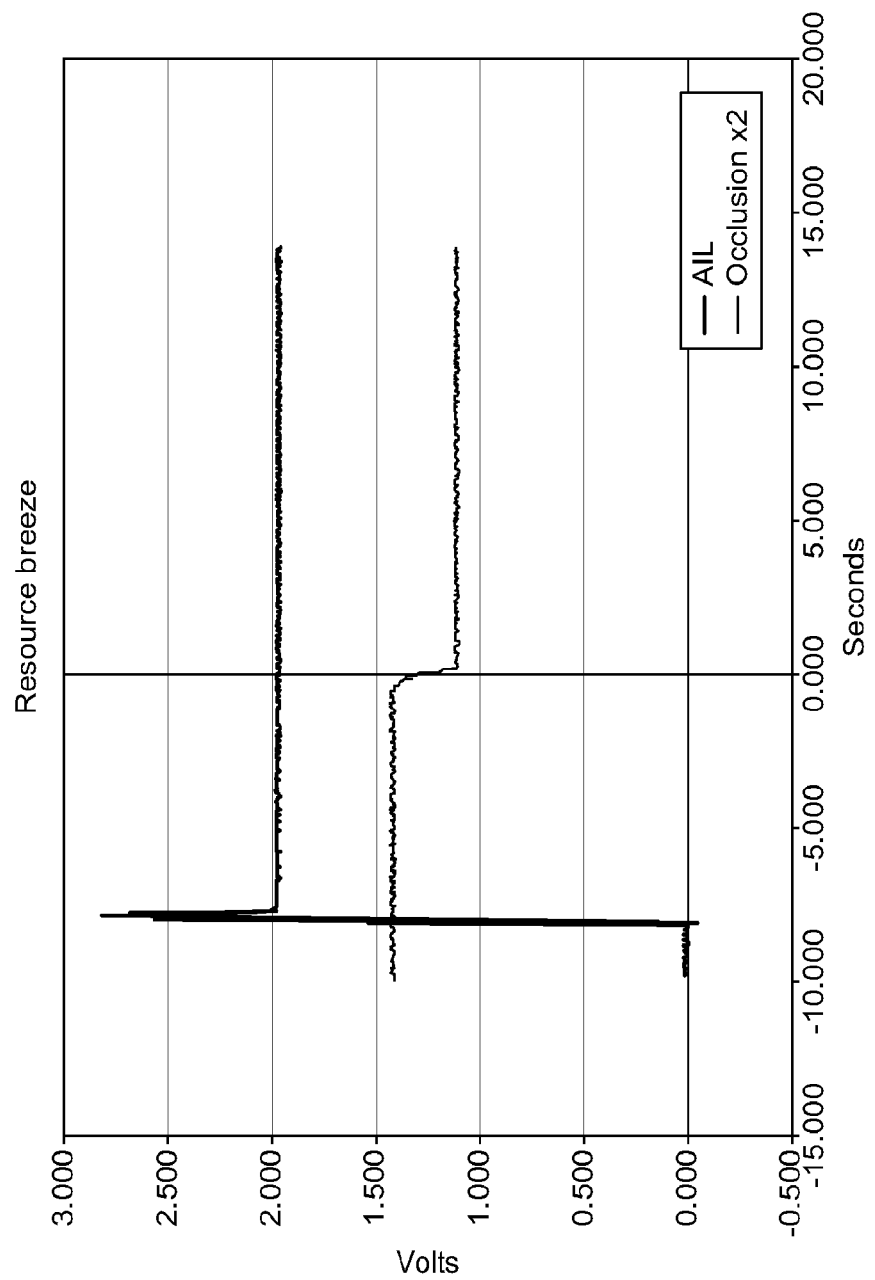
FIG. 65 shows a graph indicating feed to air transitions for a non-viscous, watery feed as measured by an air-in-line sensor and an occlusion sensor according to an embodiment of the present disclosure.

FIG. 65 illustrates that a non-viscous, watery feed such as RESOURCE® BREEZE manufactured by Nestlé Nutrition, has a different reaction than previous graphs with respect to occlusion sensor 608 signal. RESOURCE® BREEZE is a fruit-flavored, clear liquid nutritional beverage and, thus, is a watery feed. As discussed previously, because watery feeds have lower infra-red reflectance, watery feeds all produce a positive offset to the baseline of the occlusion sensor data such that the fluid to air transition is marked by a falling edge.

Figure 66:
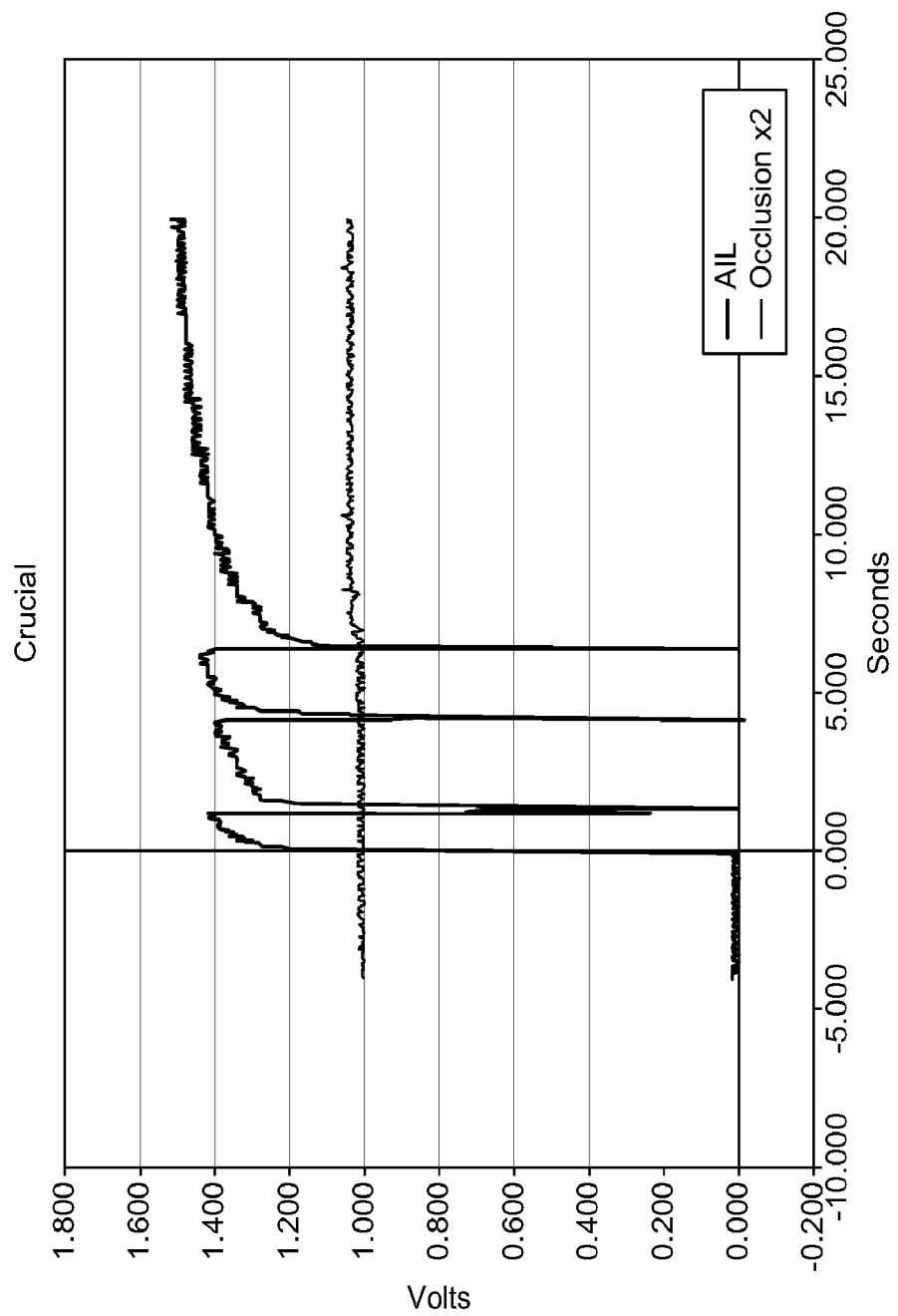
FIG. 66 shows a graph indicating feed to air transitions for a feed/water blend containing high amounts of peptide-based proteins as measured by an air-in-line sensor and an occlusion sensor according to an embodiment of the present disclosure.

In certain embodiments, the presence of an occlusion sensor 608 may be enough to properly detect a fluid to air transition. However, this is not always the case. For example, FIG. 66 illustrates a graph for the air-in-line and occlusion sensor data that resulted from testing with Nestlé Nutrition's CRUCIAL® nutritional composition, which is a feed/water blend composition containing high amounts of peptide-based protein, omega-3 fatty acids, and elevated levels of antioxidants, vitamins and minerals. As shown in FIG. 66, the occlusion signal is very weak for the feed/water blend, which indicates that there are conditions where the feed ingredients that cause a strong infra-red reflection (e.g., rising edge fluid to air transition) when mixed with water (e.g., a strong absorber, falling edge fluid to air transition) cancel each other out to result in an occlusion sensor signal equivalent to air.

Therefore, by using both air-in-line infra-red sensors 606 and occlusion infra-red sensors 608, cassettes and pumps of the present disclosure should be able to accurately detect initial fluid to air transitions regardless of the feed type.

As previously discussed, cassettes of the present disclosure may be used in combination with enteral feeding systems for the administration of medical fluids. The cassettes typically include an enteral feeding tube set having several long sections of tubing that are connected to a centralized, shorter section of tubing. When the cassette is inserted into a pumping device of the enteral feeding system, a pump (e.g., a peristaltic pump) may be forced into a recessed area of the cassette, thereby forcing a tubing of the cassette to be stretched into the recessed area of the cassette. Because infusion cassettes typically have blunt edges across which the tubing is stretched, the tubing may be kinked as the tubing is stretched over the edges of the cassette. Such kinking is undesirable as is may occlude the tube and prevent fluids from passing through the tube.

Figure 67:
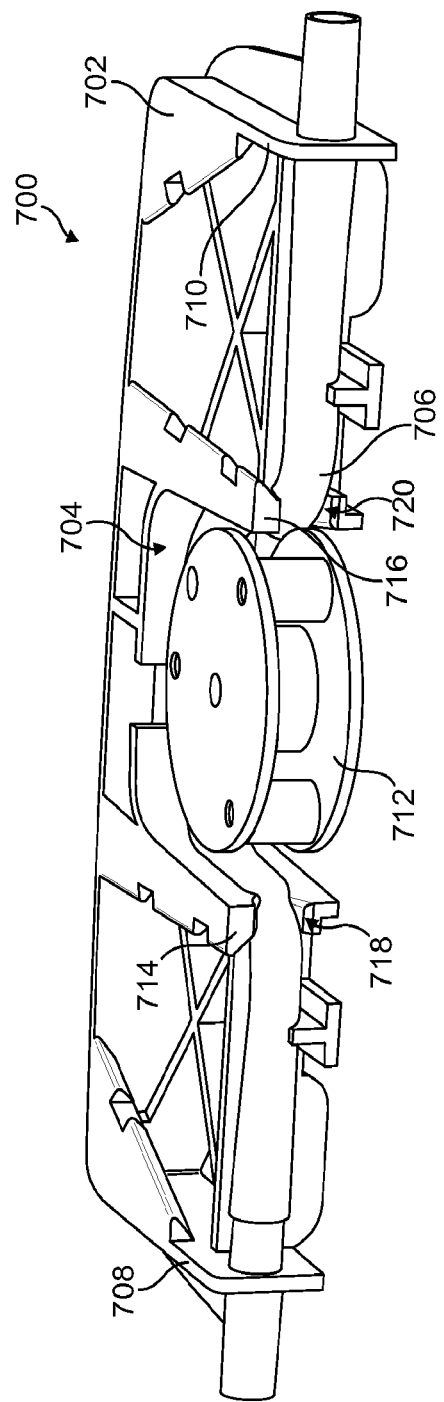
FIG. 67 shows a cassette having a housing with notches according to an embodiment of the present disclosure.

In an embodiment, and as shown in FIG. 67, cassette 700 is provided in accordance with the present disclosure. Cassette 700 includes housing 702, a recessed area 704 within housing 702, and tubing 706. Tubing 706 is connected to cassette 700 at first and second ends 708, 710 of cassette 700. When cassette 700 is inserted into a pumping device (not shown) having a pump 712 such as, for example, a peristaltic pump, pump 712 contacts tubing 706 and pushes tubing 706 into recessed area 704 of housing 702. As pump 712 stretches and pushes tubing 706 into recessed area 704, tubing 706 is forced to traverse and bend at edges 714, 716 of housing 702 where housing 702 begins to form recessed area 704. Requiring tubing 706 to traverse and to bend at edges 714, 716 to stretch into recessed area 704 increases the risk that tubing 706 will kink at the location where the tubing 706 bends.

Figure 68:
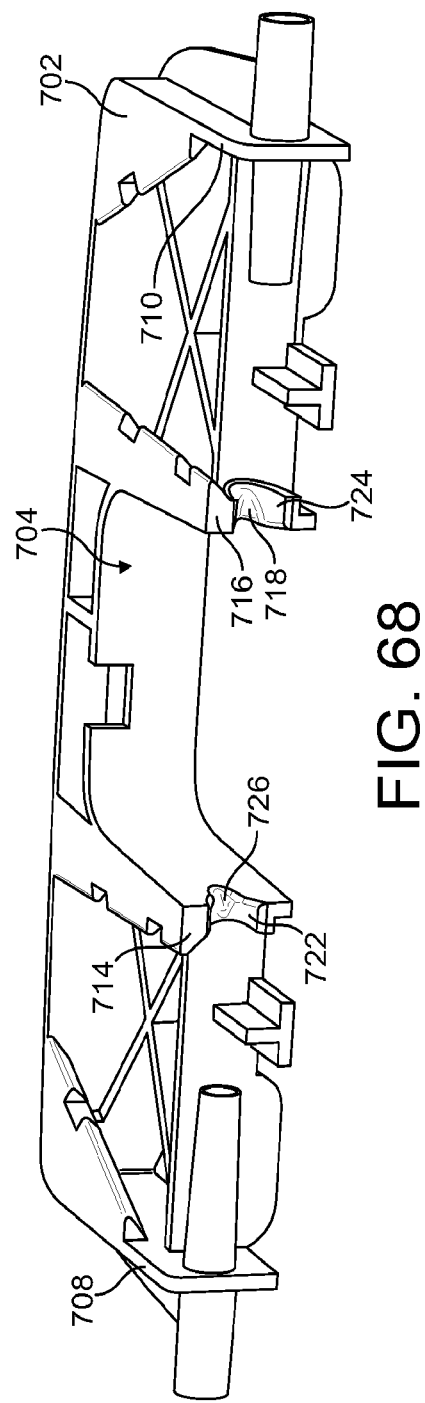
FIG. 68 shows a cassette having a housing with notches according to an embodiment of the present disclosure.

In an embodiment, and to avoid kinks from forming in tubing 706 at the location of edges, 714, 716, notches 718, 720 may be formed into edges 714, 716 that allow tubing 706 to stretch into recessed area 704 without bending at a sharp, 90° angle. Instead, notches 718, 720 provide tubing 706 with a somewhat rounded shape that allows tubing 706 to assume a softer bend as tubing 706 stretches into recessed area 704. Notches 718, 720 may have any shape known in the art including, for example, semi-circular, "V"-shaped, oblong, squared, rectangular, etc. In an embodiment illustrated in FIG. 68, notches 718, 720 are substantially "V"-shaped. To form the substantially "V"-shape edges of housing 702 in FIG. 68, edges 714, 716 include a cut-away portion 722, 724 having a substantially semi-circular shape, which opens in a direction of insertion of cassette 700 into a pumping device (not shown). Cut-away portion 722, 724 is further shaped to include a beveled edge 726, 728 on a central portion on a recessed area 704 side of cut-away portion 722, 724. The combination of the cut-away portion 722, 724 and beveled edge 726, 728 form a "V"-shape that allows tubing 706 to bend softly as tubing is stretched into recessed area 704. The softer bend of tubing 706 helps to prevent the formation of kinks in tubing 706 at edges 714, 716.

As discussed above with respect to flow restriction devices for cassettes, it is important that infusion pump cassettes be properly loaded into pumping devices so as to avoid leakage of infusion fluids from the cassette tubing. Similarly, once properly inserted into a pumping device, the cassette must be secured in the device so that any movement of the device or cassette does not shift the position of the cassette within the device to cause leakage of the infusion fluids.

Figure 69:
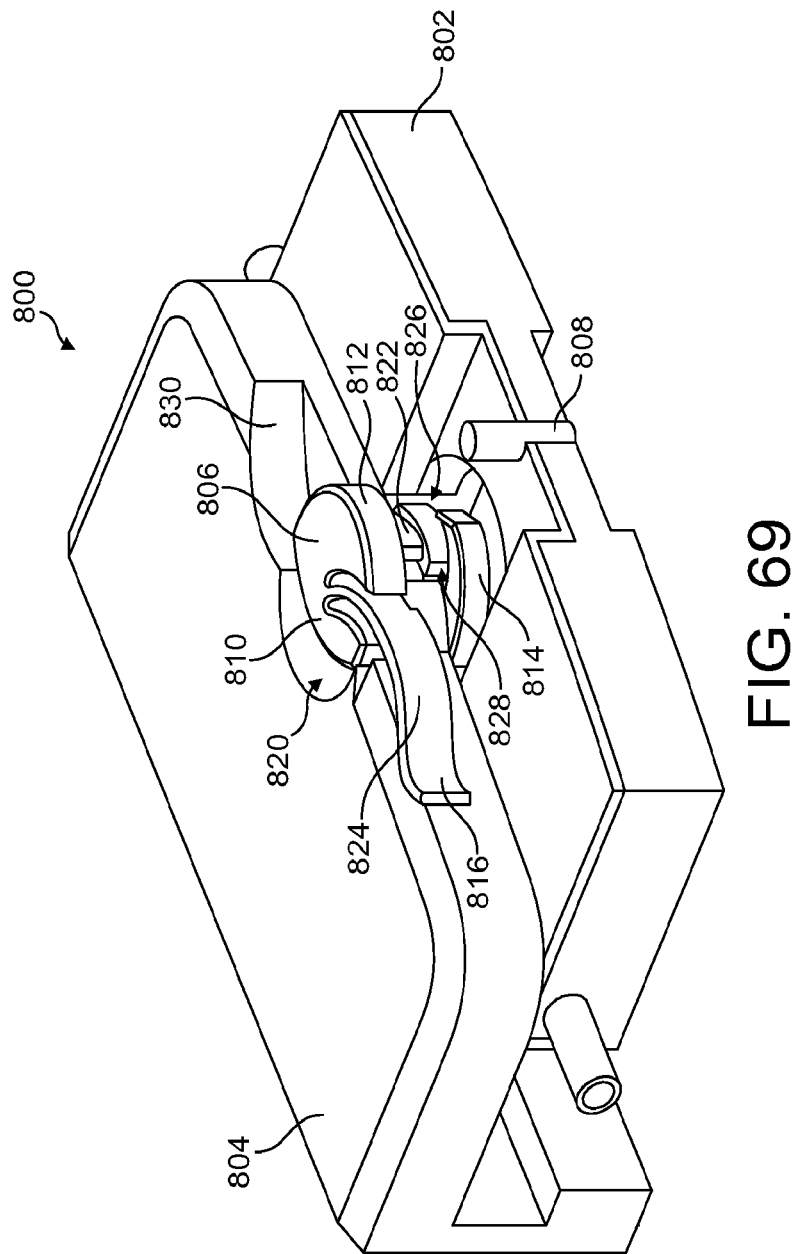
FIG. 69 shows a pumping device and cassette including a latch mechanism according to an embodiment of the present disclosure.

In an embodiment, a fluid delivery system 800 is provided that includes a cassette 802 and a pumping device 804. Fluid delivery system 800 is designed to secure cassette 802 within pumping device 804 through the use of a latch mechanism 806 of pumping device 804 that works in conjunction with a projection 808 of cassette 802, as shown in FIG. 69. Projection 808 may be substantially cylindrically shaped, and may be located on an outer portion of a top surface of cassette 802, as is shown in FIG. 69. In an embodiment, projection 808 is a peg, a pin, etc. However, the skilled artisan will appreciate that projection 808 may have any shape known in the art including, for example, oblong, rectangular, etc. The skilled artisan will also appreciate that projection 808 may be located at any place on cassette 802 so long as latch mechanism 806 and projection 808 are able to communicate to lock cassette 802 into place in pumping device 804.

In an embodiment, latch mechanism 806 includes a body 810 having an upper portion 812, a lower portion 814 and a central portion 816 connecting upper and lower portions 812, 814. Upper portion 812 includes an arm 816 that is formed integrally with upper portion 812. While arm 818 is formed integrally with upper portion 812 of body 810 in the illustrated embodiment, the skilled artisan will appreciate that arm 818 need not be formed integrally with body 810 and may be attached to upper portion 812 by any attachment means known in the art. The skilled artisan will also appreciate that arm 816 may also be located on lower portion 814 of body 810. As is also shown in FIG. 69, pumping device 804 includes a cup-shaped portion 820 having a cylindrically shaped snap-in section 822 that is configured to receive central portion 816 of body 810.

Figure 70:
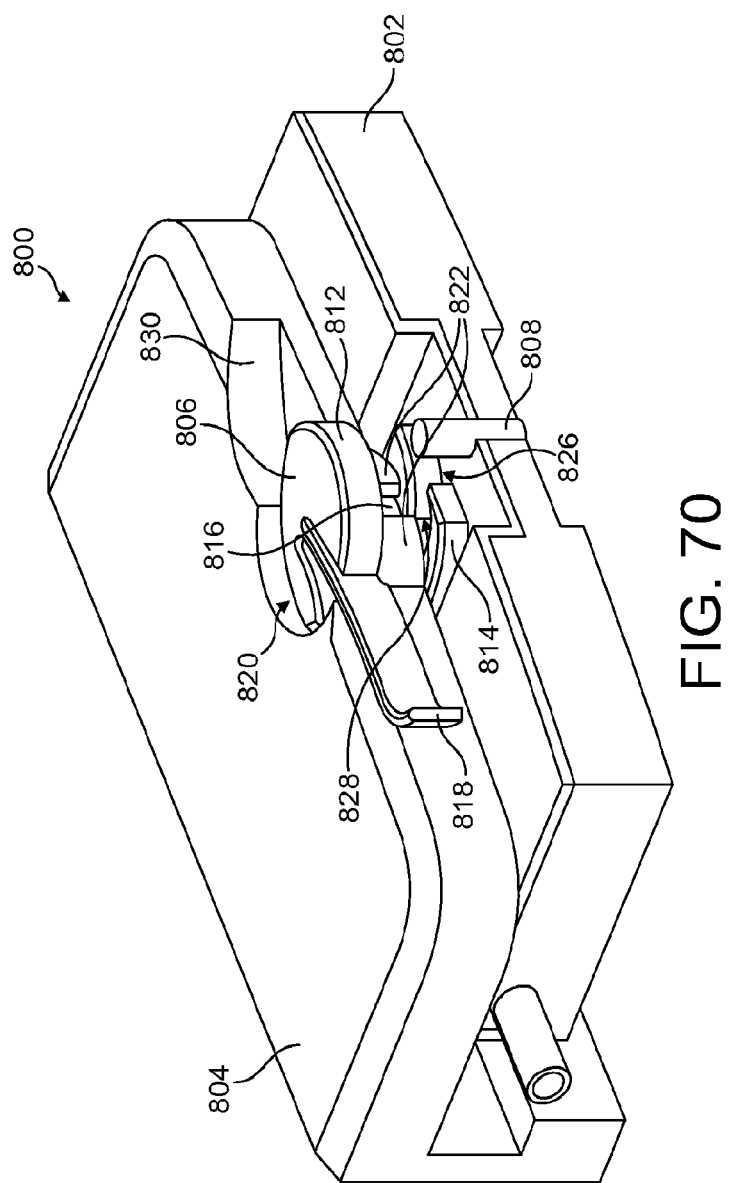
FIG. 70 shows a pumping device and cassette including a latch mechanism according to an embodiment of the present disclosure.

In operation, latch mechanism 806 is snapped into snap-in section 822 and arm 818 is rotated to the left, as is shown in FIG. 69. Cassette 802 is then inserted into pumping device 804. As discussed previously, latching mechanism 806 and projection 808 act together to secure cassette 802 into pumping device 804. Specifically, arm 818 acts as a spring that may be biased to rotate upon release of the bias to lock cassette 802 in place. As is shown in FIG. 70, arm 818 includes a curved portion 824 that may be pressed flat against pumping device 804 so as to bias the arm 818 to push against pumping device 804. Pressing curved portion 824 flat against pumping device 804 rotates latching mechanism 806 slightly in a clockwise direction. Rotating latching mechanism 806 aligns projection 808 with an opening 826 in lower portion 814. Opening 826 is located contiguous to a curved, cut-away portion 828 of lower portion 814, which will be traversed by projection 808 as latching mechanism 806 locks cassette 802 into place, as will be discussed further below. As cassette 802 continues to be inserted into pumping device 804, projection 808 will enter opening 826.

Figure 71:
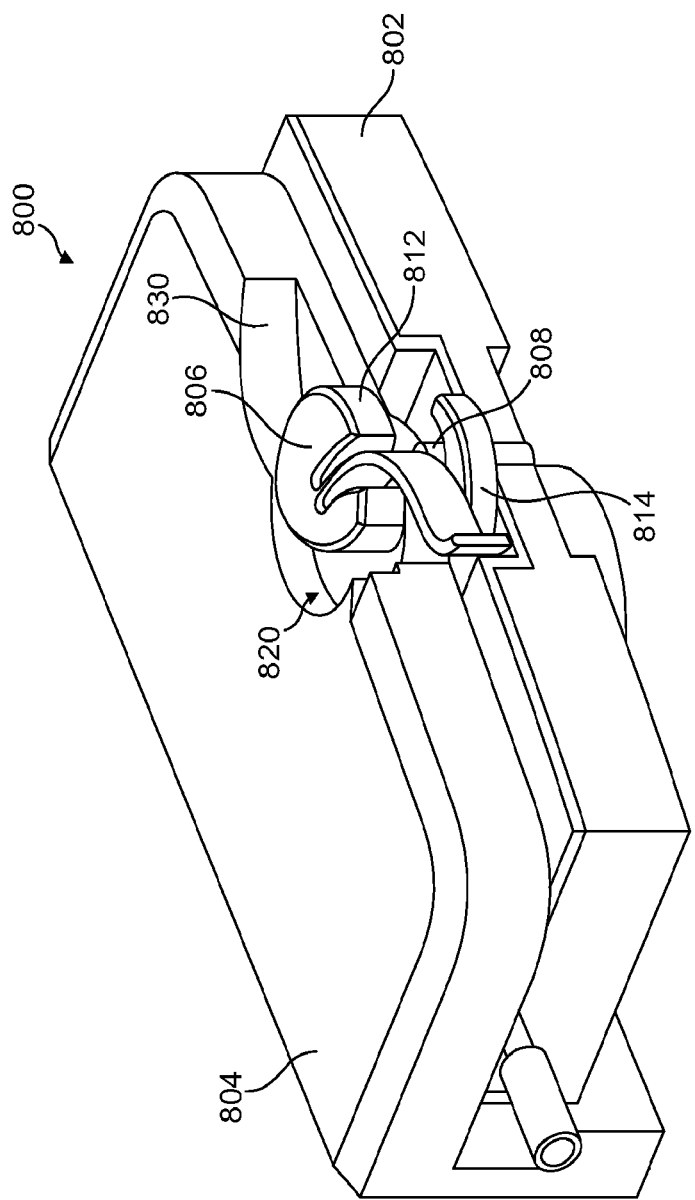
FIG. 71 shows a pumping device and cassette including a latch mechanism according to an embodiment of the present disclosure.

When curved portion 824 is released and pushes against pumping device 804 in reaction to the bias of curved portion 824, latching mechanism 806 will rotate counter-clockwise in cup portion 820 to move arm 818 from a left side of pumping device 804 to a right side. As latching mechanism 806 rotates counter-clockwise, projection 808 traverses cut-away portion 828. The rotation of latching mechanism 806 and traversing of cut-away portion 828 by projection 808 pulls cassette 802 into proper alignment in pumping device 804, as is shown in FIG. 71.

Figure 72:
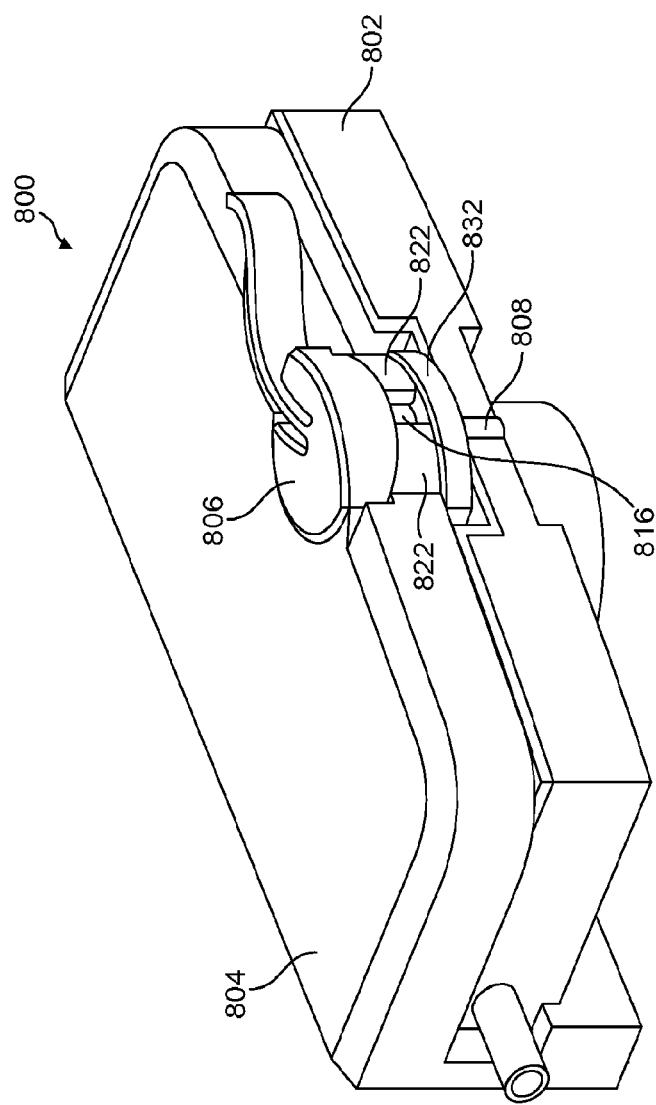
FIG. 72 shows a pumping device and cassette including a latch mechanism according to an embodiment of the present disclosure.

FIG. 72 shows cassette 802 fully inserted into pumping device 804 and latching mechanism 806 fully rotated such that arm 818 is located on a right side of pumping device 804. The right side of pumping device 804 includes a curved portion 830 that is so constructed and arranged to receive curved portion 824 of arm 818. Curved portion 830 of pumping device 804 allows latching mechanism 806 to fully rotate such that a substantially flat portion 832 of lower portion 814 faces outward from pumping device 804.

The use of a latching mechanism of the type described above provides a simple design that does not require a spring to provide snap action for insertion of a cassette into a pumping device. Rather, the latching mechanism includes a handle arm that is configured to provide such snap action.

Figure 73:
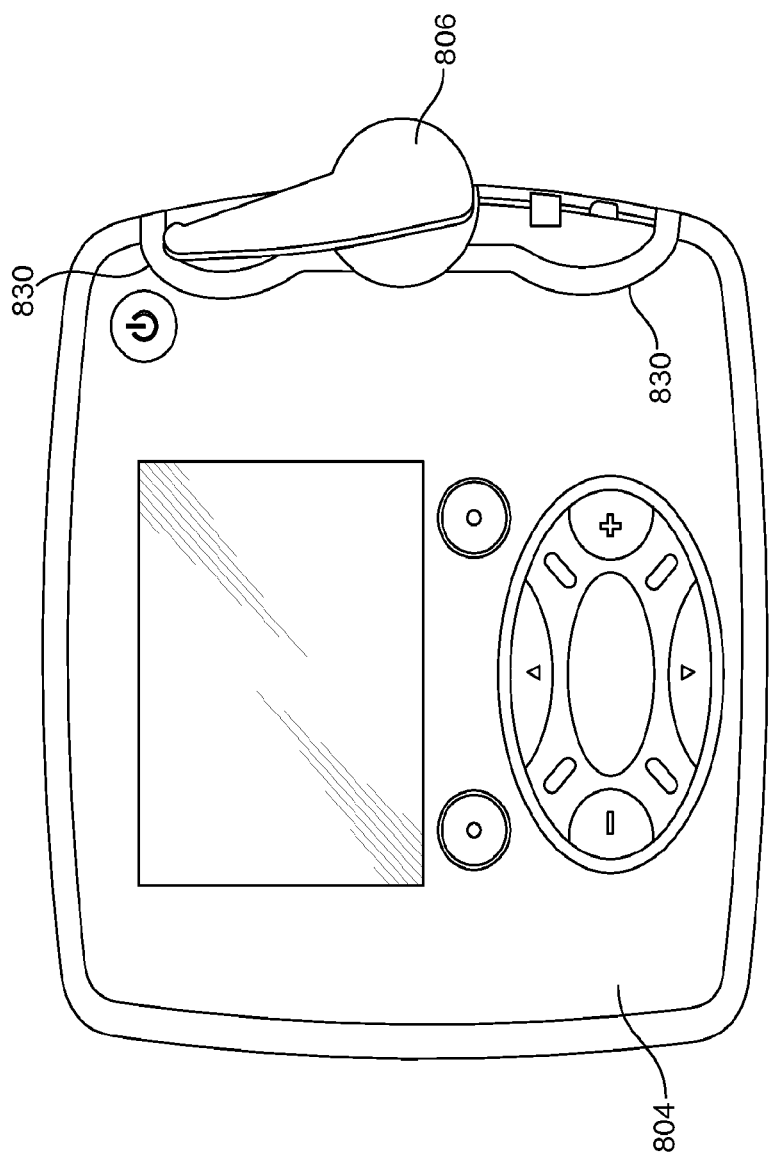
FIG. 73 shows a pumping device including a latch mechanism according to an embodiment of the present disclosure.

In another embodiment, as shown in FIG. 73, pumping device 804 may include more than one curved portion 830 to allow latching mechanism 806 to fully rotate from an open to a closed position. In the embodiment illustrated in FIG. 73, arm 818 of latching mechanism 806 does not included curved portion 824. Accordingly, the skilled artisan will appreciate that latching mechanism 806 need not operate solely via the spring action of the curved portion 824, and may include internal components that provide snap action for latching mechanism 806.

In another embodiment, and similar to the air-in-line sensor and occlusion sensor devices discussed above, FIG. 74 illustrates a latch sensor device 900 of the present disclosure. Latch sensor device 900 may be used to detect whether a cassette 902 has been inserted into a pumping device 904 and/or whether cassette 802 is properly inserted into pumping device 904. The use of such a latch detection device 900 may serve as a safety feature of pumping device 904 by prohibiting the pumping of a medical fluid through cassette 902 unless the cassette 902 is fully and correctly inserted into pumping device 904.

For example, and similar to the air-in-line and occlusion sensor devices described above, the latch sensor device 900 may include an infra-red sensor 906 that has an infra-red emitter 908 and an infra-red phototransistor receiver or photo-diode 910 in a portion of pumping device 904. The infra-red emitter 908 may be capable of emitting an infra-red signal that is reflected by an infra-red reflective surface 912 of a latch arm 914 and received by the infra-red phototransistor 910 of pumping device 904. Infra-red emitter 908 may project from any location on pumping device 904. Depending on the location of infra-red emitter 908 on pumping device 904, the latch arm 914 may have an infra-red reflecting surface 912 on an outer portion that corresponds to the location of the infra-red emitter 908 and phototransistor 910. Such a configuration may prevent the infra-red phototransistor 910 from receiving the infra-red signal until cassette 902 fully and/or properly inserted into pumping device 904 and the latch arm 914 is fully closed.

Figure 74:
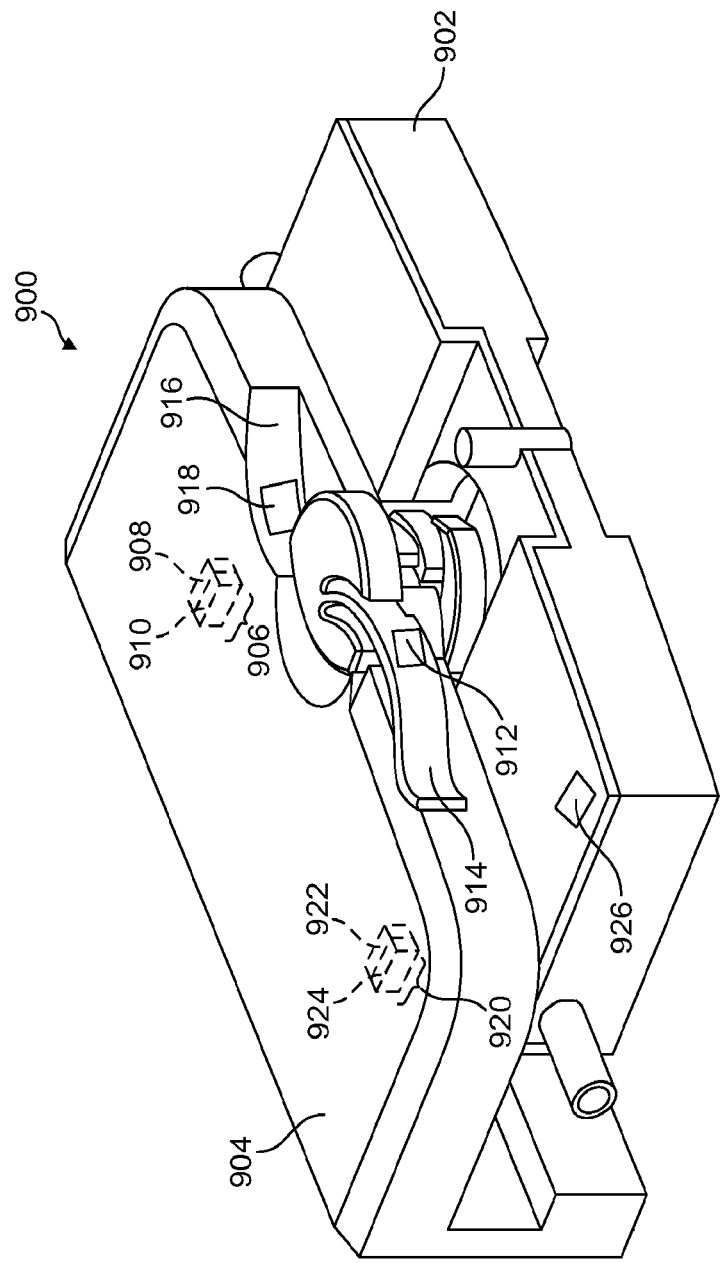
FIG. 74 shows a pumping device and cassette according to an embodiment of the present disclosure.

For example, pumping device 904 of FIG. 74 may include an infra-red sensor 906 including an infra-red emitter 908 and receiver 910 near the curved portion 916 of pumping device 904. Latch arm 914 may have an infra-red reflective surface 912 at a corresponding location thereon. In such an embodiment, when arm 914 has fully rotated to lock in cassette 902 and lies flush with curved portion 916 of pumping device 904, an infra-red signal emitted by an infra-red emitter 908 is reflected off the infra-red reflective surface 912 and received by the infra-red phototransistor 910, which indicates that cassette 902 is fully and properly inserted in to pumping device 904.

In another embodiment, pumping device 904 of FIG. 74 may include an infra-red sensor 920 including an infra-red emitter 922 and receiver 924 near on a left side of pumping device 904. Cassette 902 may have an infra-red reflective surface 926 at a corresponding location thereon. In such an embodiment, when cassette 902 has been fully inserted into pumping device 904, an infra-red signal emitted by an infra-red emitter 922 is reflected off the infra-red reflective surface 926 and received by the infra-red phototransistor 924, which indicates that cassette 902 is fully and properly inserted in to pumping device 904.

In an alternative embodiment, and as discussed previously with respect to the air-in-line sensor device and the occlusion sensor device, the present disclosure also provides a cassette 902 having a component 918 that provides a false reading to the latch sensor 906. In other words, cassettes of the present disclosure may include a component that provides a consistent positive reading to infra-red sensors of the latch sensor device 900 such that infra-red sensors will not detect any changes to the strength of an emitted infra-red signal.

For example, a cassette 902 may be manufactured for use with a component 918 to provide a false reading to latch sensor 906. Such a component may include any component known in the art that will reflect a sufficient and consistent amount of an emitted infra-red signal back to the infra-red sensor system such that infra-red sensor system detects no change in the strength of the infra-red signal. The component may include, for example, an infra-red reflective surface such as white paper or a metallic surface, as discussed previously, or infra-red reflective plastics, glass, paint, tape, etc. Although component 918 is illustrated in FIG. 74 as a flat material such as, for example, tape or paint, the skilled artisan will understand that the previously mentioned infra-red reflective materials, or any additional infra-red reflective materials known in the art, may be used.

False reading component 918 may be located on cassette 902, pumping device 904 or a latch arm 914 intermediate latch sensor 906 and infra-red reflective surface 912. For example, in an embodiment, component 918 is an infra-red reflective piece of tape located intermediate latch sensor 906 and infra-red reflective surface 912. Such a configuration will allow latch sensor 906 to emit an infra-red signal using an infra-red reflective light emitting diode 908, which may be reflected using a false reading component 918, and which will be received by infra-red sensor system using infra-red phototransistor receiver 910. According to such a configuration, latch sensor device 906 will continuously receive a positive and continuous infra-red signal regardless of whether latch 914 is fully and properly closed to secure cassette 902 in pumping device 904.

Cassettes of the present disclosure provide several different advantages to aid in delivering medical fluids to a patient. For example, cassettes of the present disclosure may include infra-red reflective components that interact with sensor devices of a pumping device with which cassettes operate. Additionally, cassettes may also include, for example, cut-away portions of a cassette housing that allow tubing of the cassette to be stretched over edges of the cassette housing without kinking when a pump of the pumping device is received within a recessed area of the cassette. Accordingly, because the cassettes of the present disclosure provide different embodiments that require components of the cassette to interact with components of the pumping device, it is important that the cassettes are properly inserted into pumping devices.

Figure 75:
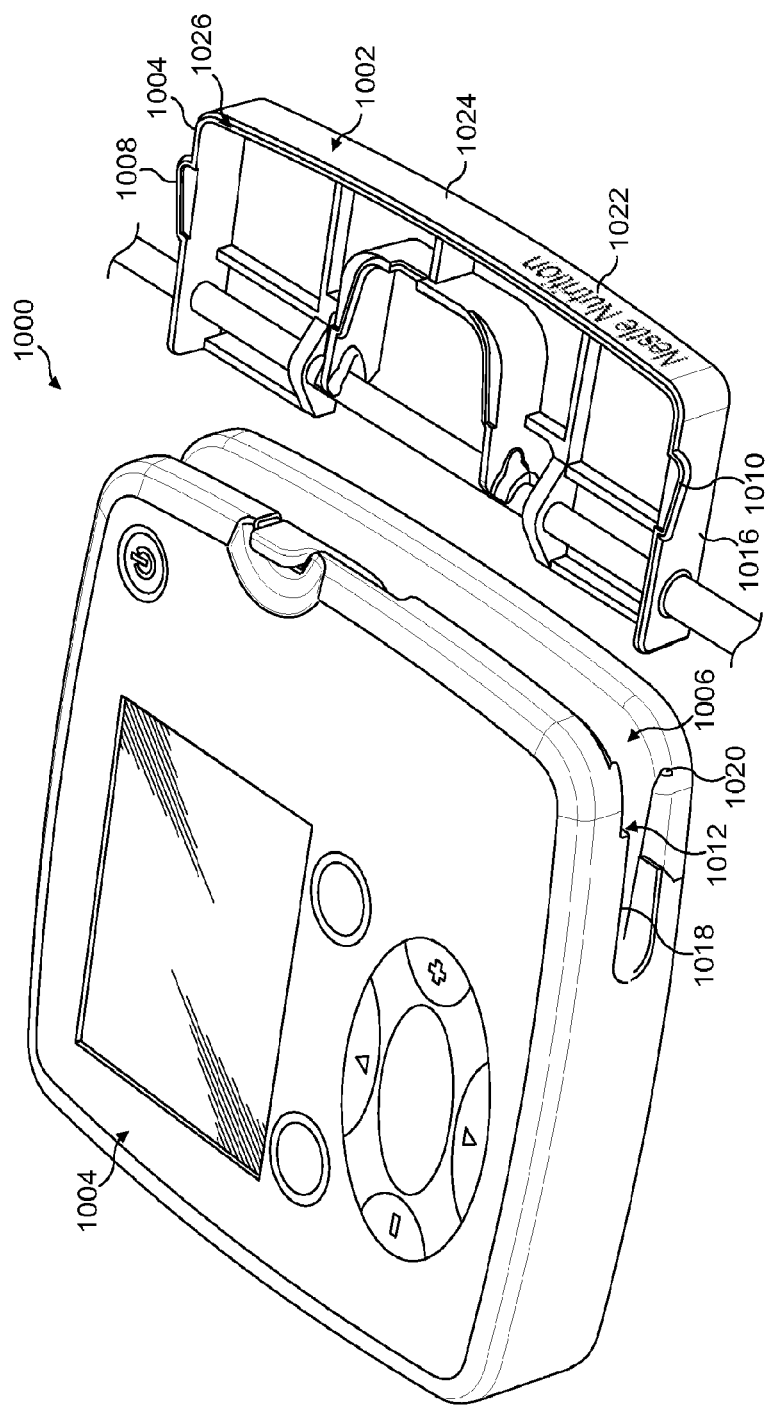
FIG. 75 shows a pumping device and cassette according to an embodiment of the present disclosure.

In an embodiment, the present disclosure relates to cassettes having different components for guiding a cassette into proper alignment within a pumping device. For example, as shown in FIG. 75, a medical fluid delivery system 1000 is provided. The medical fluid delivery system 1000 includes a cassette 1002 and a pumping device 1004 having an opening 1006 so constructed and arranged to receive cassette 1002. When inserted into opening 1006, cassette 1002 should have a small amount of space between all sides of cassette 1002 and the interior of opening 1006. However, cassette 1002 should generally be stationary when inserted into opening 1006.

Figure 76:
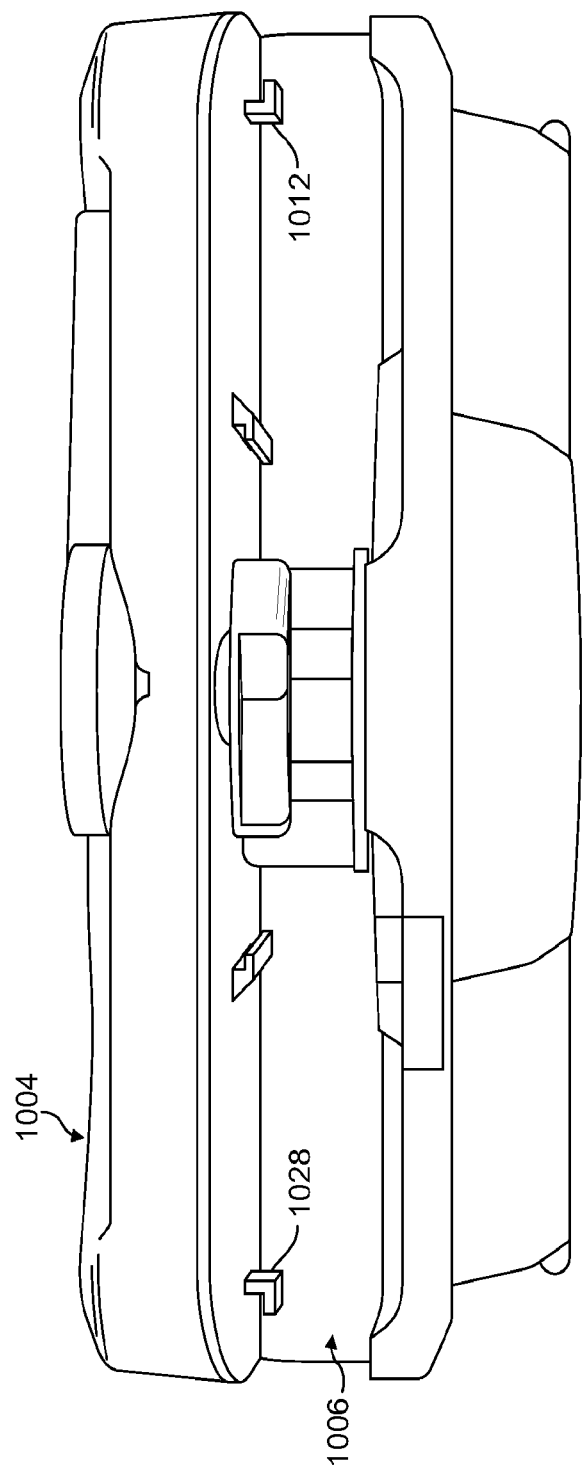
FIG. 76 shows a pumping device according to an embodiment of the present disclosure.

Further, cassette 1002 should only be inserted into opening 1006 in one orientation to avoid damaging or breaking cassette 1002. In an embodiment, and to ensure that cassette 1002 is properly inserted into opening 1006, cassette 1002 is provided with tab members 1008, 1010 that work in conjunction with ledges 1012 of pumping device 1004. The skilled artisan will appreciate that, although only one ledge 1012 is illustrated in FIG. 75, pumping device 1004 may also have an opposite yet identical ledge (now shown) on the opposite side of pumping device 1004. For example, FIG. 76 shows two ledges 1012, 1028, one on either side of pumping device 1004.

Tab members 1008, 1010 may be projections that extend outward from the first and second side walls 1014, 1016 of cassette 1002, as shown in FIG. 75 and are used to guide cassette 1002 into pumping device 1004 when tab members 1008, 1010 contact ledges 1012, 1028. In an embodiment, tab members 1008, 1010 may be wing-shaped projections, as is shown in FIG. 75. As used herein, "wing-shaped" means a substantially rounded rectangular shape the tapers in width from one end to the opposite end along one side of the rounded rectangular shape. An exemplary "wing-shaped" projection 1008, 1010 is illustrated in FIG. 75. The skilled artisan will appreciate, however, that tab members 1008, 1010 may have any shape known in the art including, for example, semi-circular, square, rectangular, oblong, triangular, etc.

Figure 77:
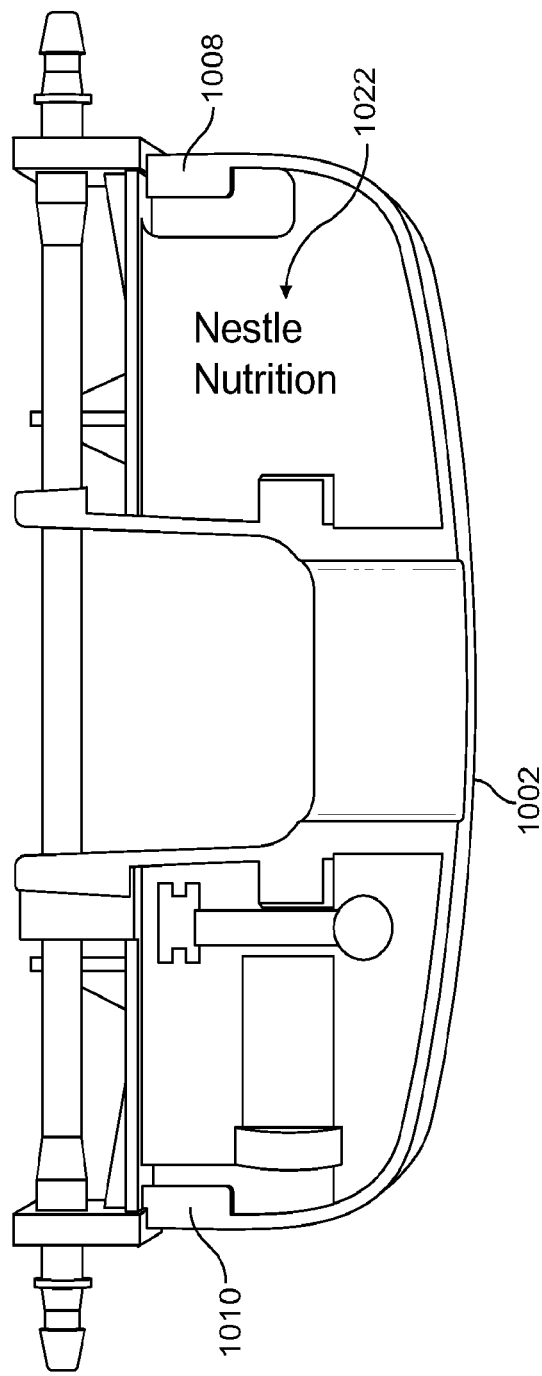
FIG. 77 shows a cassette according to an embodiment of the present disclosure.

For example, FIG. 77 illustrates another embodiment of cassette 1002 having inward extending tab members 1008, 1010 that are also used to guide cassette 1002 into pumping device 1004 when tab members 1008, 1010 contact ledges 1012, 1028. In this embodiment, tab members 1008, 1010 are substantially rectangular in shape. Tab members 1008, 1010 may be formed integral with cassette 1002. In another embodiment, however, tab members 1008, 1010 may be adhered to cassette 1002.

Cassette 1002 may include any number of tab members 1008, 1010. In an embodiment, cassette 1002 includes one tab member 1008, 1010 on each side wall 1014, 1016. However, the skilled artisan will appreciate that cassette 1002 may include more than two tab members 1008, 1010. In an embodiment, cassette 1002 includes a number of tab members 1008, 1010 selected from the group consisting of one, two, three, four, five, six or combinations thereof.

As shown in FIG. 75, in an embodiment, tab members 1008, 1010 may be located on an upper portion of first and second side walls 1014, 1016 of cassette 1002. Accordingly, ledges 1012 must also be located on an upper portion 1018 of side walls of opening 1006. The skilled artisan will understand that, although only one upper portion 1018 of a side wall of opening 1006 is illustrated in FIG. 75, an upper portion of an opposite side wall (not shown) is present on an opposing side of pumping device 1004. The skilled artisan will also appreciate that tab members 1008, 1010 need not be located on an upper portion of side walls 1014, 1016, but may be located at any portion of side walls 1014, 1016.

Pumping device 1004 may include a portion 1020 that is designed to prevent cassette 1002 from being inserted incorrectly. For example, if it is attempted to load cassette 1002 into opening 1006 upside-down, tab members 1008, 1010 would contact portion 1020, which would prevent cassette 1002 from being inserted in such orientation. The skilled artisan will appreciate that portion 1020 need not have any specific shape so long as portion 1020 prevents cassette 1002 from being inserted into opening 1006 in an incorrect orientation when portion 1020 contacts tab members 1008, 1010.

In operation, as cassette 1002 is being inserted into opening 1006 of pumping device 1004, tab members 1008, 1010 must be aligned with ledges 1012, which will aid in guiding cassette 1002 into proper placement within pumping device 1004. Accordingly, tab members 1008, 1010 and ledges 1012 ensure that cassette 1002 is properly centered within pumping device 1004 and not inserted too far or not far enough into opening 1006.

In another embodiment, cassette 1002 may be provided with a logo or other directional indicator 1022 to ensure that cassette 1002 is properly inserted into pumping device 1004. For example, cassette 1002 may have directional indicator 1022 such as, for example, the logo Nestlé Nutrition, placed upright on a third side 1024 of cassette 1002, as shown in FIG. 75, or on top surface 1026 of cassette 1002, as shown in FIG. 77. Directional indicator 1022 is oriented upright or on a top surface so as to be properly read by a patient or healthcare provider inserting cassette 1002 into pumping device 1004. Such orientation will urge the patient or healthcare provider to insert cassette 1002 into pumping device in a correct orientation. If, on the other hand, a patient or healthcare provider attempts to insert cassette 1002 into pumping device 1004 in an upside-down orientation, the patient will realize that directional indicator 1022 is upside-down or not present, which will alert patient that cassette 1002 is being inserted incorrectly.

Although directional indicator 1022 is illustrated in FIG. 75 as a written logo, the skilled artisan will understand that directional indicator 1022 may be any letter, words, symbols or numbers to indicate a proper orientation of cassette 1002 for insertion into pumping device 1004. For example, directional indicator 1022 may also be an arrow pointing upward to indicate a top of cassette 1002. Directional indicator 1022 may also be a different written indicator such as the phrase "this end up." The skilled artisan will appreciate that the directional indicator 1022 is not limited to the logo as illustrated in FIG. 75. Additionally, the skilled artisan will appreciate that cassette 1002 may include more than one directional indicator 1022 and in any combination of directional indicators 1002. For example, in an embodiment, cassette 1002 includes the written indicator "this end up" and also includes an arrow point toward a top side 1026 of cassette 1002.

Similarly, the directional indicator 1022 may be applied to or associated with cassette 1002 by any means known in the art. For example, directional indicator 1022 may be on a sticker and adhered to first, second or third walls 1014, 1016, 1024, respectively, during manufacturing of cassette 1002. Alternatively, directional indicator 1022 may be etched, lasered, molded or formed into a wall of cassette 1002. The physical make-up of directional indicator 1022 is not, however, limited to the examples provided in the present disclosure so long as directional indicator 1022 is able to convey to a patient or healthcare provider the proper orientation of cassette 1002 for insertion into pumping device 1004.

Figure 78:
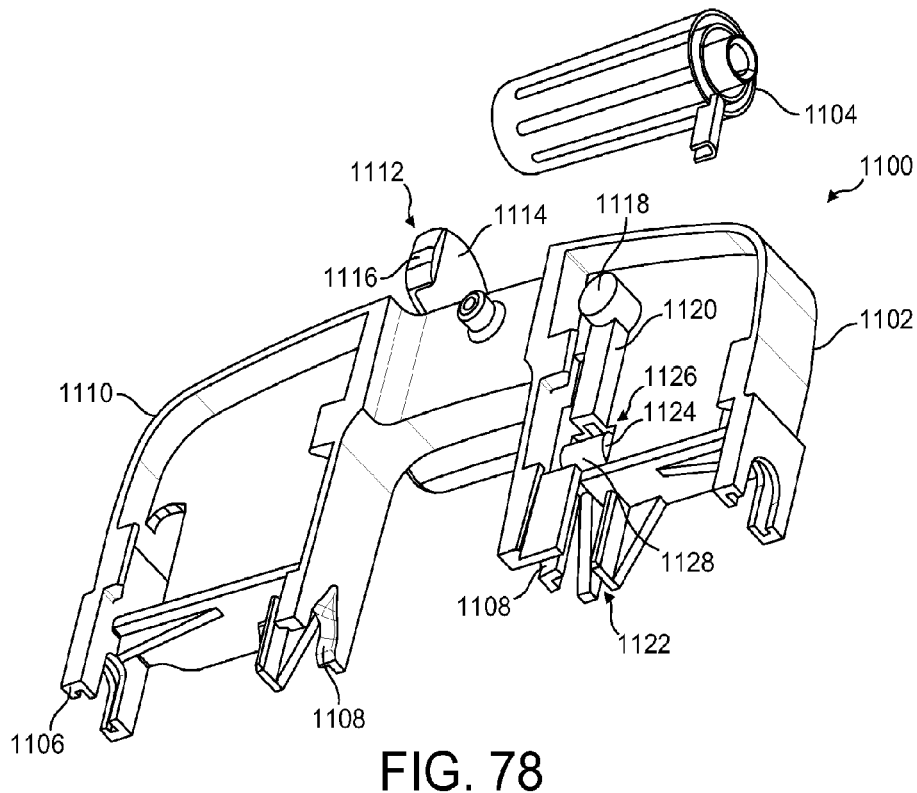
FIG. 78 shows a bottom perspective view of a cassette having an anti-free flow mechanism according to an embodiment of the present disclosure.

In yet another embodiment, an anti-free flow valve assembly is provided to restrict free-flow of fluid through the tubing associated with a cassette prior to insertion of the cassette into a pumping device and/or connection to a patient. As illustrated in FIG. 78, in an embodiment, an anti-free flow valve mechanism 1100 includes a cassette 1102 and a cap 1104 configured for removable insertion into an opening 1136 of cassette 1102. Cassette 1102 includes a tubing side 1106 having notches 1108 for accepting tubing, and a distal side 1110 for engagement with cap 1104.

Cassette 1102 includes a stopper 1112 for stabilization and prevention of movement of cap 1104 when cap 1104 is removably inserted into cassette 1102, as will be discussed further below. Stopper 1112 may be any structure or mechanism that is so constructed and arranged to prevent front-to-back or side-to-side motion of cap 1104 when cap 1104 is inserted into cassette 1102. In an embodiment, and as illustrated in FIG. 78, stopper 1112 is a substantially circular shaped disk 1114 having a projection 1116 that extends from the disk 1114, on an outer edge of disk 1114, in a substantially perpendicular manner. In this embodiment, circular shaped disk 1114 prevents back-and-forth movement of cap 1104, while projection 1116 prevents side-to-side movement of cap 1104. The skilled artisan will appreciate, however, that stopper 1112 may have any size or shape known in the art including, for example, rectangular, triangular, circular, or combinations thereof, so long as stopper 1112 prevents, or limits, front-to-back or side-to-side motion of cap 1104 when cap 1104 is inserted into cassette 1102.

Figure 86:
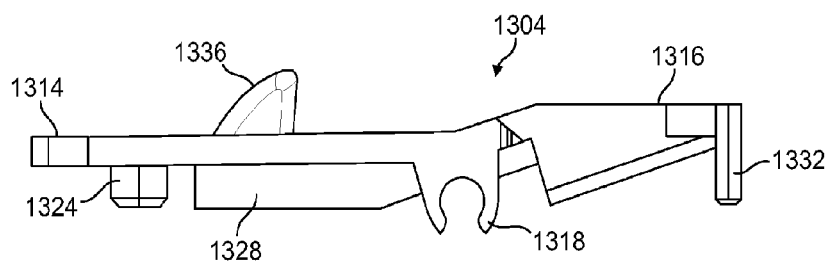
FIG. 86 shows a clamping element of a cassette having an anti-free flow mechanism according to an embodiment of the present disclosure.

Cassette 1102 also includes a circular recession 1118 and a substantially rectangular recession 1120 that are intended to receive similarly shaped projections on a valve arm 1122, which is illustrated in FIG. 86 and will be discussed further below. Cassette 1102 also includes a connecting element 1124 that sits within a recess 1126 of cassette 1102 and joins two opposing sides of recess 1126. In an embodiment, connecting element 1124 is substantially cylindrical in shape such that a substantially "C"-shaped connecting portion 1128 of valve arm 1122 may be snap-fit thereon, and rotate partially around, connecting element 1124 as valve arm 1122 rocks between a blocking position and a free-flow position, as will be discussed below. The skilled artisan will appreciate that connecting portion 1128 of valve arm 1122 need not be "C"-shaped and may be, for example, substantially "C"-shaped, circular, rectangular, hemi-spherical, or combinations thereof.

Figure 79:
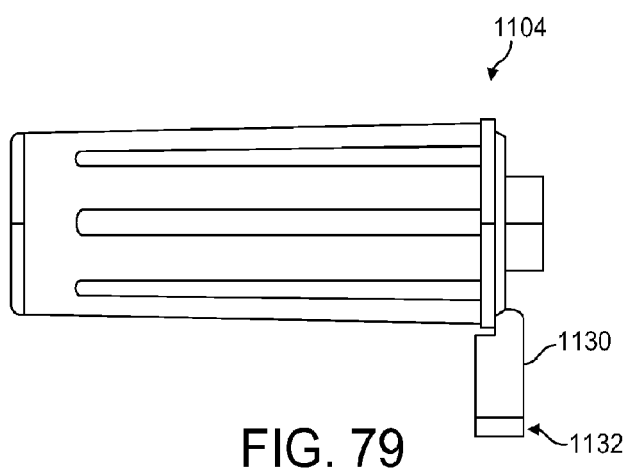
FIG. 79 shows a cap for use with a cassette having an anti-free flow mechanism accordingly to an embodiment of the present disclosure.

As shown in FIG. 79, cap 1104 is substantially cylindrical in shape and includes an actuating projection 1130 that is so constructed and arranged to engage a back end 1134 of valve arm 1122 when actuating projection 1130 of cap 1104 is inserted into opening 1136 of cassette 1102, as shown in greater detail in FIG. 80. In an embodiment, actuating projection 1130 has notched portion 1132 that mates with a corresponding notched portion 1135 of back end 1134 of valve arm 1122. Accordingly, when actuating projection 1130 is inserted into opening 1136, notched portion 1132 engages the notched portion 1134a of valve arm 1122 to press downward on back end 1134, thereby rotating valve arm 1122 about its fulcrum (e.g., "C"-shaped connecting portion 1128) and lifting a tube blocking portion 1138 of valve arm 1122, which allows for free-flow through tubing (not shown).

Although cap 1104 is illustrated as substantially cylindrical in shape, the skilled artisan will appreciate that cap 1104 may have any shape known in the art such as, for example, cylindrical, rectangular, spherical, or combinations thereof. Similarly, although actuating projection 1130 is illustrated as being substantially rectangular in shape, the skilled artisan will appreciate that actuating projection 1130 may have a shape that is, for example, substantially cylindrical, rectangular, triangular, spherical, or combinations thereof.

Cap 1104 is so constructed and arranged to receive a portion of a tubing, a tubing end or a tubing luer therein. It is important to ensure that the tubing (not shown) packaged with cassette 1102 does not become contaminated during packaging or shipment prior to use for therapy. By packaging an end of tubing in cap 1104 during packaging and shipment, the cap 1104 prevents any contaminants from entering the tubing prior to therapy. To administer therapy, cap 1104 may be removed by the patient or a care-giver and the tubing portion connected to a patient line, as will be discussed below.

The embodiment illustrated in FIG. 80 is useful for packaging and shipping of cassette 1102 in combination with tubing (not shown). Shipping cassette 1102 in a free-flow position prevents extended periods of time during which a tube blocking portion 1138 of valve arm 1122 applies stress to the tubing. This reduction in stress may lead to less damage of the tubing prior to use by a patient, which may result in less reported instances of treatment malfunctions.

When a patient is ready to begin treatment using a pumping device (not shown) and cassette 1102, patient simply removes cap 1104 from cassette 1102, which disengages notched portion 1132 of cap 1104 from back end 1134 of valve arm 1122, which allows valve arm 1122 to rotate about its fulcrum (e.g., "C"-shaped engagement portion 1128) and return tube blocking portion 1138 of valve arm 1122 to its biased position, which prevents free-flow through tubing (not shown). When cap 1104 is removed from cassette 1102, cap 1104 is removed from a tubing end (not shown) housed therein and tubing end may be connected to a patient line for receipt of therapy. When cassette 1102 is inserted into a pumping device for use, the pumping device will have an internal tab member for applying pressure to back end 1134 of valve arm 1122 to return valve arm 1122 to its free-flow position by unblocking the tubing. In the free-flow position, solution is allowed to flow freely through the tubing to provide therapy to a patient.

Figure 81B:
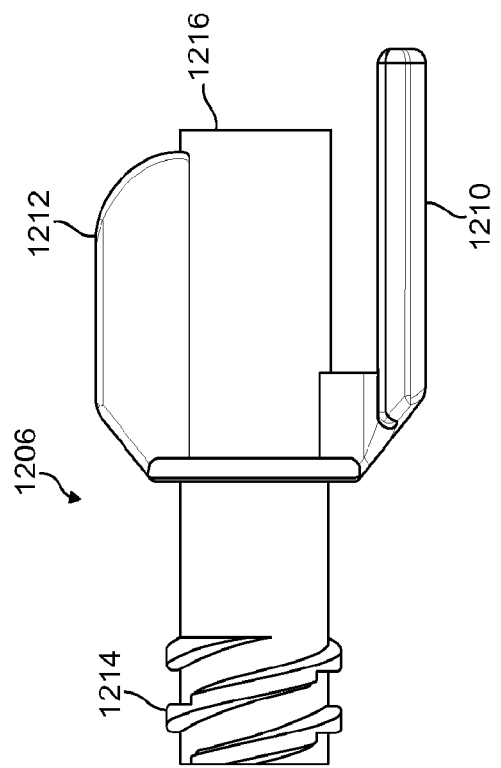
FIG. 81b shows a luer hook for use with a cassette having an anti-free flow mechanism accordingly to an embodiment of the present disclosure.
Figure 81A:
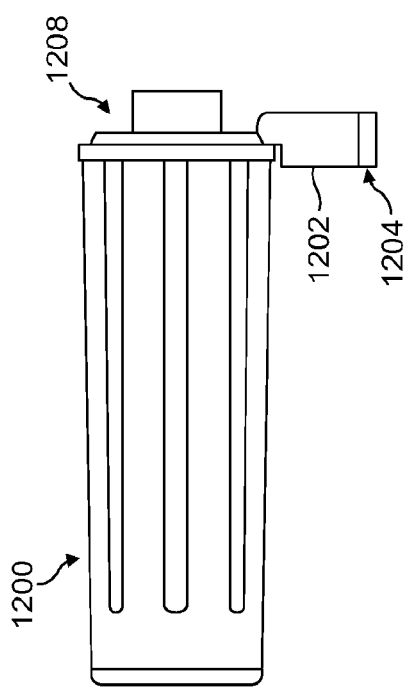
FIG. 81a shows a cap for use with a cassette having an anti-free flow mechanism accordingly to an embodiment of the present disclosure.

In another embodiment, a cap may be used in combination with a luer to prevent free-flow through the tubing of a cassette of the present disclosure. For example, FIG. 81a shows a cap 1200 that is similar to cap 1104 described above. In this regard, cap 1200 also includes an actuating projection 1202 that extends from cap 1200, as well as a notched portion 1204 that is configured to engage a notched portion of a valve arm (not shown) similar to valve arm 1122 described above. In this embodiment, cap 1200 is so constructed and arranged to receive a luer 1206, as illustrated in FIG. 81b, within an open end 1208, as is shown in FIG. 82.

Luer 1206 includes a hook portion 1210, a fin portion 1212, a threaded end 1214, and a tubing end 1216. Prior to the use of a pumping device and cassette 1218 for therapy, threaded end 1214 of luer 1206 resides within cap 1200, which aids in maintaining the sterility of threaded end 1214 before threaded end 1214 is connected to a patient line for therapy. Tubing end 1216 of luer 1206 may be connected to the tubing associated with cassette 1218 by any means known in the art. For example, tubing of cassette 1218 may be molded into tubing end 1216 of luer 1206 on an outflow side of the cassette 1218. Accordingly, in order for the patient to receive therapy from the pumping device, luer 1206 must be pulled out of cap 1200 and connected to a patient line using threaded end 1214. Fin portion 1212 of luer 1206 aids in gripping and rotating luer 1206 to attach luer 1206 to a patient line.

Similar to a previous embodiment, actuating projection 1202 of cap 1200 may be so constructed and arranged so as to engage a valve arm (not shown) to either restrict or allow free-flow of fluids through the tubing of a cassette. In this regard, actuating projection 1202 of cap 1200 is inserted into a first opening 1220 on a distal side of cassette 1218 where a notched portion 1204 of actuating projection 1202 engages a corresponding back notched portion of a valve arm as described above. In this embodiment, however, a different stopper for preventing movement or dislodging of luer 1212 and cap 1200 is provided.

Figure 82:
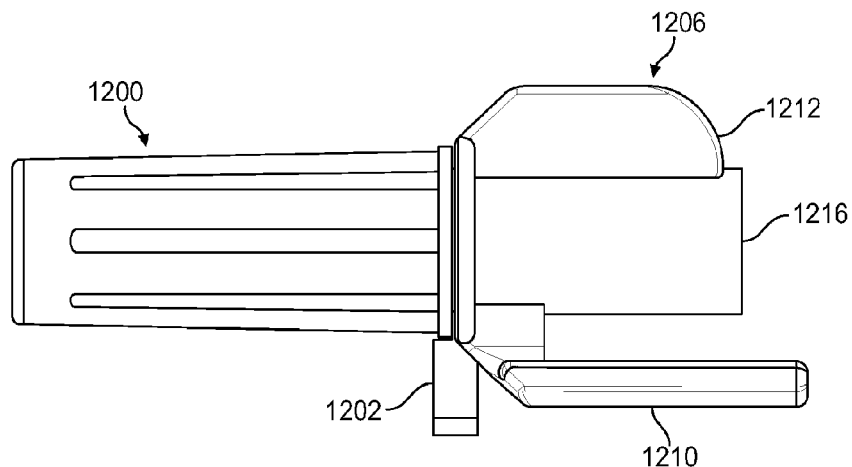
FIG. 82 shows a cap and a luer hook for use with a cassette having an anti-free flow mechanism accordingly to an embodiment of the present disclosure.
Figure 83:
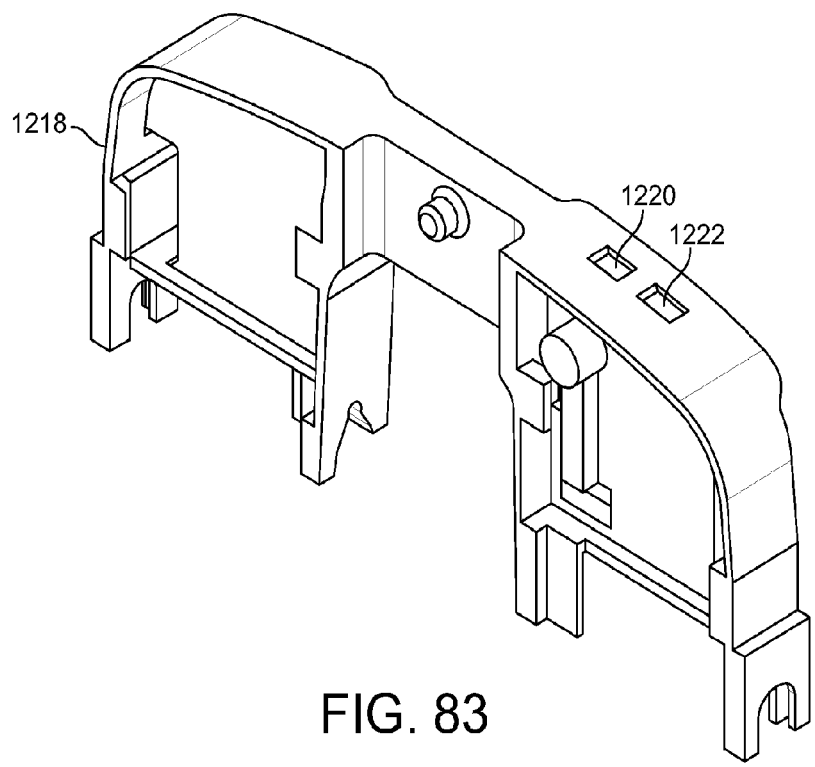
FIG. 83 shows a cassette accordingly to an embodiment of the present disclosure.

For example, after combination of cap 1200 and luer 1206 (as illustrated in FIG. 82), hook portion 1210 of luer 1206 may be inserted into a second opening 1222 of cassette 1218 that is adjacent first opening 1220, as is illustrated in FIG. 83. Hook portion 1210 should be inserted at an angle into second opening 1222 prior to insertion of actuating projection 1202 of cap 1200 into first opening 1220. When a substantial amount of hook portion 1210 is inserted into second opening 1222, force may be applied to cap 1200 to insert actuating projection 1202 into first opening 1220. In this configuration, hook portion 1210 and inserted actuating projection 1202 maintain the position of the cap 1200/luer 1206 combination in a distal end of cassette 1218 such that the cap 1200/luer 1206 combination will not disengage during packaging and shipping, thereby allowing a tube blocking portion of a valve arm to block fluid free flow through the tubing.

Similar to the above described process, when a patient is ready to begin treatment using a pumping device and cassette 1218, patient simply pulls upward on cap 1200 to dislodge actuating projection 1202 from first opening 1220 to disengage notched portion 1204 of cap 1200 from a back, notched end of a valve arm, which allows the valve arm to rotate slightly about its fulcrum and return to its biased position, which prevents free-flow through tubing (not shown). The patient may then slide hook portion 1210 out of second opening 1222, remove threaded end 1214 from cap 1200 and screw threaded end 1214 into a patient line for therapy. When inserted into a pumping device for use, the pumping device will have an internal tab member for applying pressure to a back end of a valve arm to return the valve arm to its free-flow position by unblocking the tubing.

Figure 84:
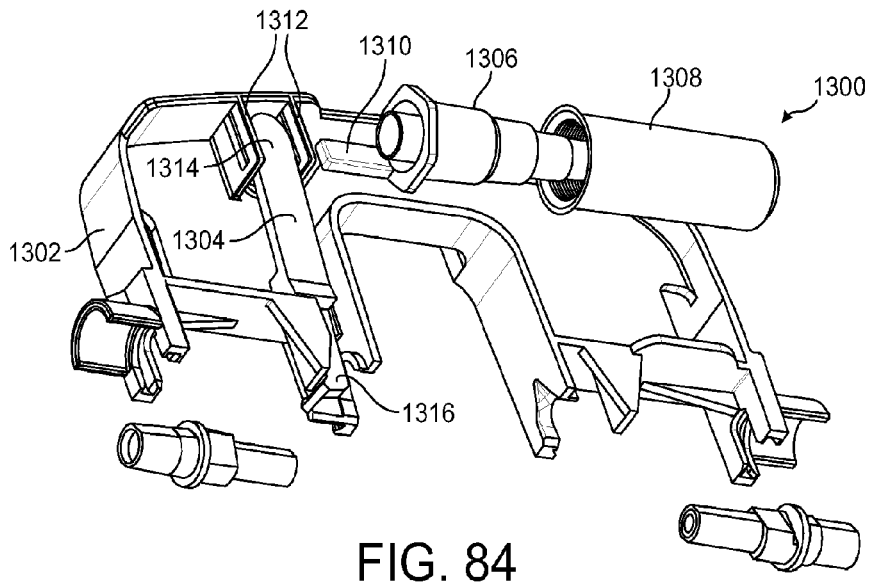
FIG. 84 shows an exploded perspective view of a cassette having an anti-free flow mechanism according to an embodiment of the present disclosure.
Figure 85:
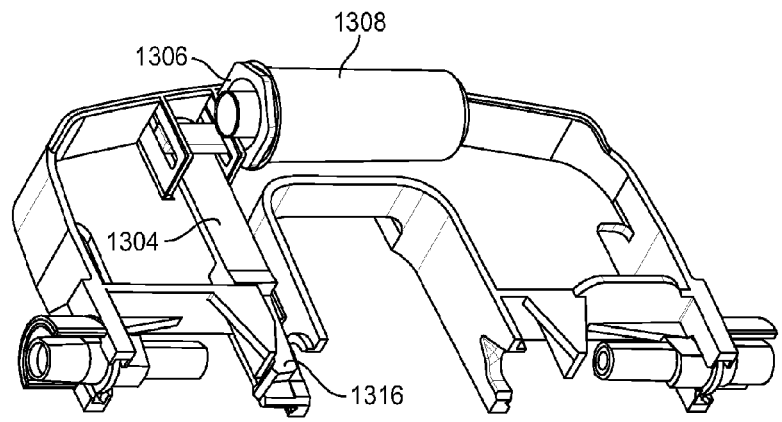
FIG. 85 shows a perspective view of a cassette having an anti-free flow mechanism according to an embodiment of the present disclosure.

FIGS. 84-86 illustrate yet another embodiment of an anti-free flow assembly 1300 that may be used with cassettes for infusion therapy. As shown in FIG. 84, anti-free flow mechanism 1300 includes cassette 1302 having a valve arm 1304, a luer 1306 and a cap 1308. In this embodiment, luer 1306 and cap 1308 are not located on an outside distal end of cassette 1302, but rather are located on an upper interior portion of cassette 1302. Similar to previous embodiments, luer 1306 and cap 1308 are oriented parallel to a length of cassette 1302. However, in this embodiment, cap 1308 does not activate valve arm 1304 via a projection extending substantially perpendicular to a length of cap 1308. Instead, luer 1306 includes an actuating projection 1310 that is oriented substantially parallel to a length of luer 1306.

To orient valve arm 1304 in a free-flow position, actuating projection 1310 is inserted into the slots of two bracket-like structures 1312 on cassette 1302, thereby pushing a back end 1314 of valve arm 1304 down, allowing a front end 1316 of valve arm 1304 to raise up, which allows fluid to flow through the tubing of cassette 1302. The fully inserted position of actuating projection 1310 is illustrated in FIG. 85.

Figure 87:
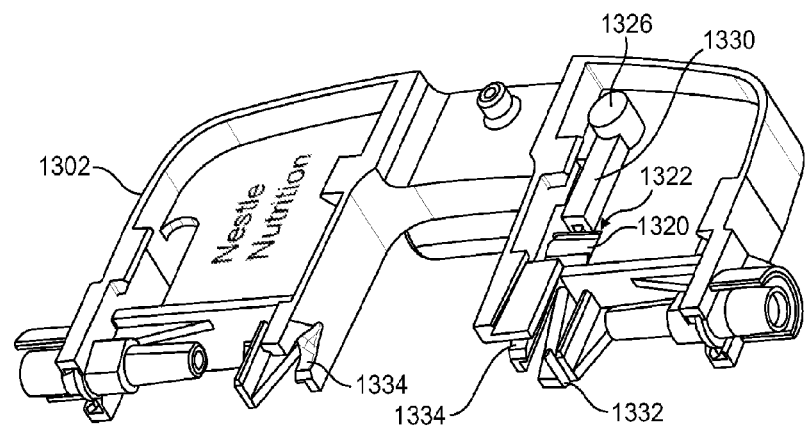
FIG. 87 shows a perspective view of a cassette having an anti-free flow mechanism according to an embodiment of the present disclosure.

As discussed briefly above, valve arm 1304 of FIG. 86 includes a substantially "C"-shaped connecting portion 1318 that engages with a connecting element 1320 of cassette 1302, as shown in FIG. 87. Connecting element 1320 sits within a recess 1322 of cassette 1302 and joins two opposing sides of recess 1322. In an embodiment, connecting element 1320 is substantially cylindrical in shape such that "C"-shaped connecting portion 1318 of valve arm 1304 may be snap-fit onto, and rotate partially around, connecting element 1320 as valve arm 1304 rocks between a fluid blocking position and a free-flow position.

FIG. 86 also illustrates that valve arm 1304 further includes a substantially cylindrical shaped protrusion 1324 that mates with circular recession 1326 to stabilize the movement of valve arm 1304 as it rocks between a fluid blocking position and a free-flow position. Valve arm 1304 also includes a substantially rectangular shaped protrusion 1328 that mates with rectangular recession 1330 of cassette 1302 for similar purposes.

As shown in FIG. 86, valve arm 1304 may also include a tube retaining portion 1332 that is so constructed and arranged to maintain a position of the cassette tubing that is located in notches 1334 of cassette 1302. Although tube retaining portion 1332 is not illustrated in every embodiment of the present disclosure, the skilled artisan would appreciate that such a structure may be used in any embodiment disclosed in the present disclosure. Additionally, although tube retaining portion 1332 is illustrated as substantially cylindrical in shape, the skilled artisan will appreciate that tube retaining portion 1332 is not restricted to such shape and may have any shape known in the art and useful as a retaining structure.

As is also shown in FIG. 86, valve arm 1304 may optionally include a stopper 1336 on an upper side of valve arm 1304, as will be discussed in detail below. Generally speaking, stopper 1336 is configured to interact with an internal tab member of a pumping device (not shown) that is designed to assert pressure on valve arm 1304 in order to rock valve arm 1304 from its biased anti-free flow position to its free-flow position in which front portion 1316 of valve arm 1304 is raised such that blocking portion 1332 of valve arm 1304 no longer blocks the flow of fluid through the cassette tubing.

Figure 88:
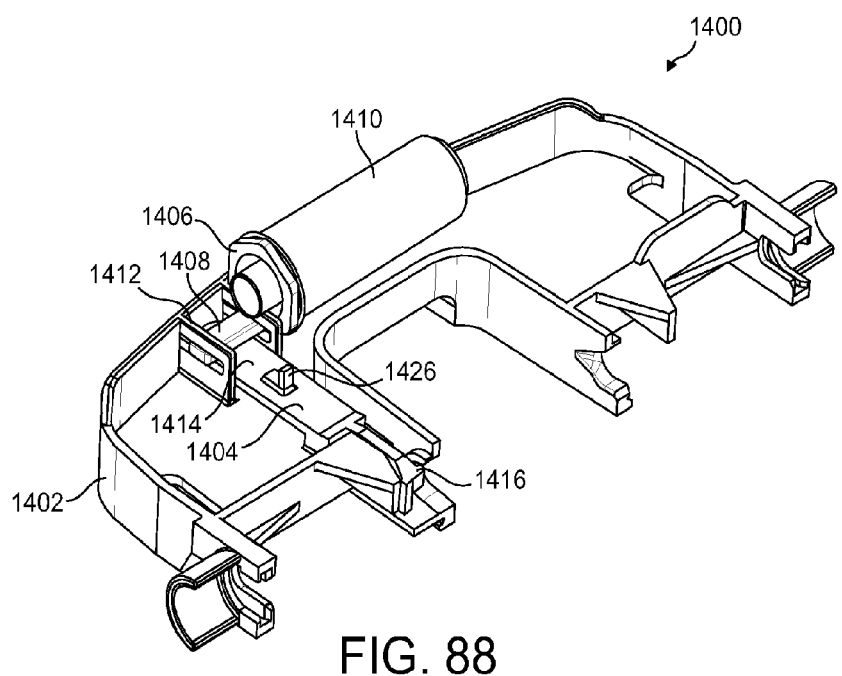
FIG. 88 shows a perspective view of a cassette having an anti-free flow mechanism according to an embodiment of the present disclosure.
Figure 89:
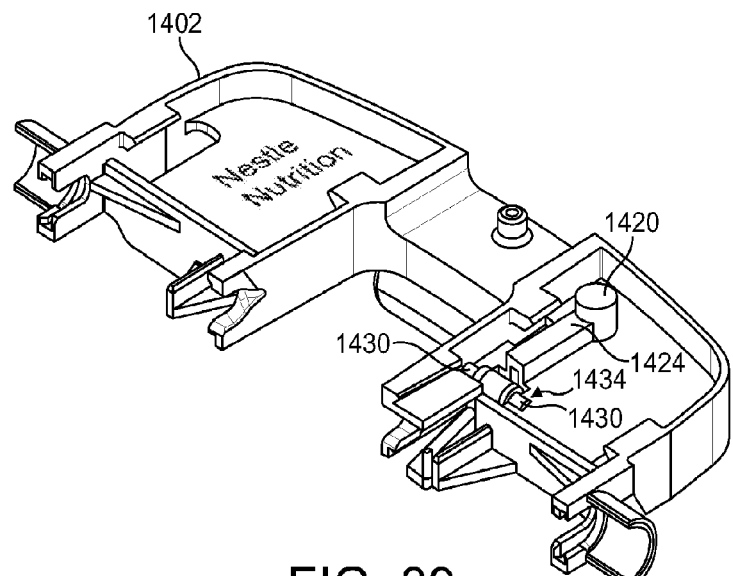
FIG. 89 shows a perspective view of a cassette having an anti-free flow mechanism according to an embodiment of the present disclosure.
Figure 90:
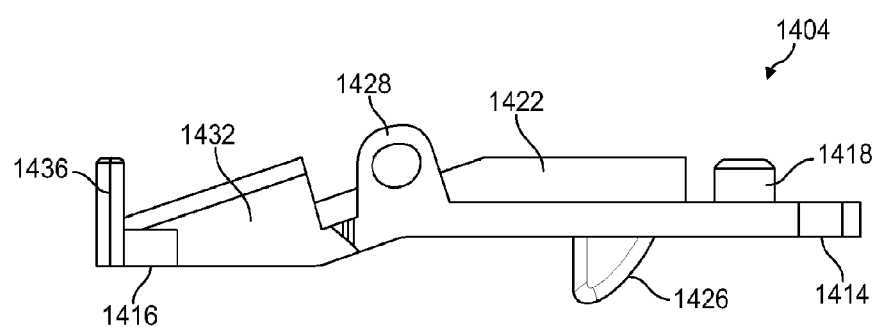
FIG. 90 shows a clamping element of a cassette having an anti-free flow mechanism according to an embodiment of the present disclosure.

FIGS. 88-90 illustrate yet another embodiment of an anti-free flow assembly 1400, which includes cassette 1402, valve arm 1404, luer 1406 having an actuating projection 1408, and cap 1410. Similar to FIGS. 84-85, actuating projection 1408 is oriented substantially parallel to a length of luer 1406 and is inserted into slots of two bracket-like structures 1412 on cassette 1402, thereby pushing a back end 1414 of valve arm 1404 down, allowing a front end 1416 of valve arm 1404 to raise up to permit fluid to flow through the tubing of cassette 1402. The fully inserted position of actuating projection 1408 is illustrated in FIG. 88.

In the embodiment illustrated in FIGS. 88-90, however, valve arm 1404 is slightly different than valve arm 1304 of FIG. 86. For example, in addition to substantially cylindrical shaped protrusion 1418, and substantially rectangular shaped protrusion 1422, valve arm 1404 of FIGS. 88-90 also includes a stopper 1426 on an upper side of valve arm 1404 and substantially "O"-shaped connecting portions 1428 that cooperate with corresponding connection elements 1430 of cassette 1402. In an embodiment, valve arm 1304 has two "O"-shaped connecting portions 1428 that are coaxial and separated by a width of valve arm 1304.

Stopper 1426 is configured to interact with an internal tab member of a pumping device (not shown) that is designed to assert pressure on valve arm 1404 in order to rock valve arm 1404 from its biased anti-free flow position to its free-flow position in which front portion 1416 of valve arm 1404 is raised such that blocking portion 1432 of valve arm 1404 no longer blocks the flow of fluid through the cassette tubing. When the tab member of the pumping device abuts against stopper 1426, cassette 1402 is fully inserted and front portion 1416 of valve arm 1404 is fully raised.

Placement of stopper 1426 at a location on valve arm 1404 that is closer to a middle section of valve arm 1404 allows the tab member of the pumping device to be located farther inward toward the center of the pumping device, as opposed to being located toward an outer portion of the pump. Locating the tab member of the pumping device toward the center of the pumping device prevents inadvertent damage and/or accidental breakage of the tab member.

In an embodiment, valve arm 1404 includes substantially "O"-shaped connecting portions 1428 that cooperate with corresponding connection elements 1430 of cassette 1402. In this embodiment, connection elements 1430 do not comprise one integral structure that connects two sides of a recess 1434 in cassette 1402. Instead, connection elements 1430 are two separate structures that are connected to, or formed integrally with, two opposing sides of recess 1434 of cassette 1402. In this regard, there exists a space between connection elements 1430 in recess 1434.

"O"-shaped connecting portions 1428 are so constructed and arranged to mate with connection elements 1430 during the manufacturing process for manufacturing cassette 1402 having valve arm 1404. As discussed above, in an embodiment, valve arm 1404 may have two "O"-shaped connecting portions 1428. During manufacturing, the "O"-shaped connecting portions 1428 are pressed slightly toward each other such that each portion extends inwardly past 90°. "O"-shaped connecting portions 1428 are then aligned with connection elements 1430 and allowed to snap back to their original biased position, which is substantially perpendicular to a length of valve arm 1404. After mating "O"-shaped connecting portions 1428 and connection elements 1430, valve arm 1404 operates in a similar manner to valve arms previously discussed to rock between a blocked fluid flow position and a free-flow position.

As shown in FIG. 90, valve arm 1404 may also optionally include a tube retaining portion 1436 that is so constructed and arranged to maintain a position of the cassette tubing that is located in notches of cassette 1402. Although tube retaining portion 1436 is not illustrated in every embodiment of the present disclosure, the skilled artisan would appreciate that such a structure may be used in any embodiment disclosed in the present disclosure. Additionally, although tube retaining portion 1436 is illustrated as substantially cylindrical in shape, the skilled artisan will appreciate that tube retaining portion 1436 is not restricted to such shape and may have any shape known in the art and useful as a retaining structure.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A system for administering a medical fluid to an individual comprising:
   a flexible tube;
   a pumping device;
   at least two cassettes each comprising a housing, wherein the cassettes are designed to be inserted into the pumping device, respectively;
   a source of medical fluid, wherein the source of medical fluid is fluidly coupled to the cassette; and
   an occlusion sensor device having infra-red sensors, wherein the first cassette comprises the tube comprising a material selected from the group consisting of opaque, infra-red reflective, and combinations thereof, and a bias bump located adjacent to a portion of the tube to prevent a sidewall of the tube located on the same side as the bias bump from expanding past the bias bump so that a sidewall of the tube opposite the bias bump can expand further toward the infra-red sensor than would be possible without the bias bump to increase the sensitivity of the occlusion detection when the first cassette is inserted in the pumping device;
   wherein the second cassette includes a false reading component for the occlusion sensor device to reflect a sufficient and consistent amount of an emitted signal back to the occlusion sensor device such that the occlusion sensor device detects no change in the intensity of the reflected infra-red signal when the second cassette is inserted in the pumping device.

2. The system of claim 1, wherein the housing comprises a recessed area that is so constructed and arranged to receive a portion of the pumping device.

3. The system of claim 1, wherein the housing comprises first and second ends for holding the flexible tube.

4. The system of claim 1, further comprising an air-in-line sensor device having infrared-sensors, wherein the first cassette includes a detection chamber of the air-in-line sensor device so constructed and arranged for receiving a portion of the flexible tube,
   wherein the second cassette includes a false reading component for the air-in-line sensor device to reflect a sufficient and consistent amount of an emitted signal back to the air-in-line sensor device such that the air-in-line sensor device detects no change in the strength of the reflected infra-red signal when the second cassette is inserted in the pumping device.

5. The system of claim 4, wherein the detection chamber comprises a window for allowing infra-red light transmission.

6. The system of claim 1, wherein the detection chamber comprises an infra-red blocking material.

7. The system of claim 1, wherein the tube expands or contracts in response to a fluid pressure therein.

8. The system of claim 1, wherein at least a portion of the housing of the tube comprises an infra-red absorbing material.

9. The system of claim 1, further comprising a latch mechanism for securing the respective cassette within the pumping device, wherein the first cassette includes a latch sensor device having infra-red sensors, and the second cassette includes a false reading component for a latch sensor device to reflect a sufficient and consistent amount of an emitted signal back to the latch sensor device such that the latch sensor device detects no change in the intensity of the reflected infra-red signal when the second cassette is inserted in the pumping device.

10. The system of claim 1, wherein the cassette includes an anti-flow valve member, wherein the anti-flow valve member comprises:
    an anti-flow valve mechanism that is biased against the flexible tube in a fluid non-delivery position to prevent flow therethough; and
    a member operatively associated with the anti-flow valve mechanism to overcome the force-applying member bias to allow flow of fluid through the tube when the housing is engaged with the pump device;
    wherein the housing is configured and dimensioned for engagement with an infusion pump as the pumping device, during or after engagement the member assumes a fluid delivery position to allow flow of the fluid through the tube, while before or as the cassette is removed from the pumping device, the member assumes the fluid non-delivery position to prevent flow of fluid through the tubing.

11. The system of claim 1, wherein the cassette includes an anti-flow valve member, wherein the anti-flow valve member comprises:
- a base comprising a holding member for holding the tube in operative engagement with the base, a first clamping surface and supporting member for supporting a connector,
- a clamping element having a second clamping surface engageable with the tube and moveable between an open position allowing flow of fluid through the tube and a closed position wherein the tube is occluded by the clamping element,
- a connector for connecting the tube with a-port on a patient, the connector being removable from the pinch clamp assembly, and
- a spring,
- the connector is adapted to engage with the clamping element so as to hold the clamping element in the open position,
- the clamping element is forced from the open to the closed position by the force of the spring as soon as the connector is removed from the assembly, and
- the clamping element is adapted to be moved from the closed to the open position when the pinch clamp assembly is mounted to the enteral feeding or infusion pump as the pumping device and the connector is removed.

12. The system of claim 11, wherein the connector is selected from the group consisting of an enteral spike, an IV spike, an enteral feeding adapter, an IV luer lock adapter, another enteral or IV component, and combinations thereof.

13. The system of claim 1, wherein the cassette includes a notch on at least one edge of the housing, the notch has a shape selected from the group consisting of semi-circular, "V"-shaped, oblong, square, rectangular, and combinations thereof.

14. The system of claim 13, wherein the notch is so constructed and arranged to partially receive the tube when the cassette is inserted into the pumping device.

15. The system of claim 1, wherein the cassette comprises at least one tab member on a side wall of the housing of the cassette, the tab members are so constructed and arranged to work with ledges on an interior wall of the pumping device to guide the cassette during insertion into the pumping device.

16. The system of claim 1, wherein the cassette includes at least one directional indicator, the directional indicator is an indicator selected from the group consisting of letters, written indicators, logos, symbols, numbers, and combinations thereof, and wherein the directional indicator is applied to a wall of the housing of the cassette using a technique selected from the group consisting of etching, lasering, molding, forming, or a sticker or stickers that is adhered to a wall of the cassette housing, and combinations thereof, the directional indicator is indicative of a proper orientation of the cassette when the cassette is inserted into the pumping device.

17. The system of claim 1, wherein at least one of the cassettes is made of a material that comprises at least one dark pigment.

18. The system of claim 1, wherein at least one of the cassettes is made of a material that comprises at least one carbon black pigment.

19. The system of claim 1, wherein the false reading component is made from a material selected from the group consisting of white paper, a metallic surface, infra-red reflective plastic, infra-red reflective glass, infra-red reflective paint, infra-red reflective tape, and combinations thereof.

20. A system for administering a medical fluid to an individual comprising:
- a flexible tube;
- a pumping device;
- at least two cassettes each comprising a housing, wherein the cassettes are designed to be inserted into the pumping device, respectively;
- a source of medical fluid, wherein the source of medical fluid is fluidly coupled to the cassette; and
- an air-in-line sensor device having infrared-sensors,
- wherein the first cassette includes a detection chamber of the air-in-line sensor device so constructed and arranged for receiving a portion of the flexible tube; and
- wherein the second cassette includes a false reading component for the air-in-line sensor device to reflect a sufficient and consistent amount of an emitted signal back to the air-in-line sensor device such that the air-in-line sensor device detects no change in the strength of the reflected infra-red signal when the second cassette is inserted in the pumping device.

21. The system of claim 20, further comprising an occlusion sensor device having infra-red sensors, wherein the first cassette comprises the tube comprising a material selected from the group consisting of opaque, infra-red reflective, and combinations thereof, and a bias bump located adjacent to a portion of the tube to prevent a sidewall of the tube located on the same side as the bias bump from expanding past the bias bump so that a sidewall of the tube opposite the bias bump can expand further toward the infra-red sensor than would be possible without the bias bump to increase the sensitivity of the occlusion detection when the first cassette is inserted in the pumping device; and
- wherein the second cassette includes a false reading component for the occlusion sensor device to reflect a sufficient and consistent amount of an emitted signal back to the occlusion sensor device such that the occlusion sensor device detects no change in the intensity of the reflected infra-red signal when the second cassette is inserted in the pumping device.

* * * * *